US007271209B2

(12) United States Patent
Li et al.

(10) Patent No.: US 7,271,209 B2
(45) Date of Patent: *Sep. 18, 2007

(54) FIBERS AND NONWOVENS FROM PLASTICIZED POLYOLEFIN COMPOSITIONS

(75) Inventors: Wen Li, Houston, TX (US); Chon-Yie Lin, Houston, TX (US); Bryan R. Chapman, Bridgewater, NJ (US); Michael B. Kelly, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 140 days.

This patent is subject to a terminal disclaimer.

(21) Appl. No.: 10/782,306

(22) Filed: Feb. 19, 2004

(65) Prior Publication Data

US 2004/0186214 A1 Sep. 23, 2004

Related U.S. Application Data

(63) Continuation-in-part of application No. 10/640,435, filed on Aug. 12, 2003, which is a continuation-in-part of application No. 10/634,351, filed on Aug. 4, 2003.

(60) Provisional application No. 60/402,665, filed on Aug. 12, 2002.

(51) Int. Cl.
*C08K 5/01* (2006.01)
*C08L 91/06* (2006.01)
*C08G 18/65* (2006.01)

(52) U.S. Cl. .............. 524/284; 524/487; 524/490; 524/491

(58) Field of Classification Search ............. 524/284, 524/487, 490, 491
See application file for complete search history.

(56) References Cited

U.S. PATENT DOCUMENTS

| | | | |
|---|---|---|---|
| 2,567,016 A | 9/1951 | Gessler et al. | |
| 3,149,178 A | 9/1964 | Hamilton et al. | |
| 3,201,364 A | 8/1965 | Salyer | |
| 3,228,896 A | 1/1966 | Canterino | |
| 3,235,529 A | 2/1966 | Nagle | |
| 3,239,478 A | 3/1966 | Harlan, Jr. | |
| 3,281,390 A | 10/1966 | O'Leary, Jr. | |
| 3,299,568 A | 1/1967 | Tobolsky | |
| 3,308,086 A | 3/1967 | Wartman | |
| 3,318,835 A | 5/1967 | Hagemeyer, Jr. et al. | |
| 3,338,778 A | 8/1967 | Hutchins et al. | |
| 3,361,702 A | 1/1968 | Wartman et al. | |
| 3,415,925 A | 12/1968 | Marans | |
| 3,437,627 A | 4/1969 | Gude et al. | |
| 3,439,088 A * | 4/1969 | Edman | 424/63 |
| 3,464,949 A | 9/1969 | Wartman et al. | |
| 3,475,368 A | 10/1969 | Metz | |
| 3,536,796 A | 10/1970 | Rock | |
| 3,541,039 A | 11/1970 | Whiton | |
| 3,563,934 A | 2/1971 | Burnett | |
| 3,752,779 A | 8/1973 | Maciejewski | |
| 3,818,105 A | 6/1974 | Coopersmith et al. | |
| 3,821,148 A | 6/1974 | Makowski et al. | |
| 3,828,105 A * | 8/1974 | Saurano | 424/70.1 |
| 3,839,261 A | 10/1974 | Aronoff et al. | |
| 3,860,543 A | 1/1975 | Masuda et al. | |
| 3,925,504 A | 12/1975 | Koleske et al. | |
| 3,925,947 A | 12/1975 | Meyers et al. | |
| 3,945,975 A | 3/1976 | Strack | |
| 3,957,898 A * | 5/1976 | Girotti et al. | 585/16 |
| 3,988,276 A | 10/1976 | Kutch et al. | |
| 4,006,115 A | 2/1977 | Elbert | |
| 4,010,127 A | 3/1977 | Taka et al. | |
| 4,041,002 A * | 8/1977 | Aboshi et al. | 524/296 |
| 4,061,805 A | 12/1977 | Thompson et al. | |
| 4,063,002 A | 12/1977 | Wilson, Jr. | |
| 4,073,782 A | 2/1978 | Kishi et al. | |
| 4,092,282 A | 5/1978 | Callan | |
| 4,094,850 A | 6/1978 | Morgan et al. | |
| 4,097,543 A | 6/1978 | Haag et al. | |
| 4,104,216 A | 8/1978 | Clampitt | |
| 4,110,185 A | 8/1978 | Williams et al. | |
| 4,118,359 A | 10/1978 | Brenner | |
| 4,118,362 A | 10/1978 | Makowski et al. | |
| 4,131,587 A | 12/1978 | Brenner | |
| 4,132,698 A | 1/1979 | Gessler et al. | |
| 4,136,072 A | 1/1979 | Ladish et al. | |
| 4,138,378 A | 2/1979 | Doss | |
| 4,147,831 A | 4/1979 | Balinth | |

(Continued)

FOREIGN PATENT DOCUMENTS

CS 215313 8/1982

(Continued)

OTHER PUBLICATIONS

Chemical Additives for Plastics Industry, 1987, pp. 99-116, Radian Corporation, NJ.

(Continued)

*Primary Examiner*—Nathan M. Nutter
(74) *Attorney, Agent, or Firm*—Michael Kerns; Catherine L. Bell

(57) ABSTRACT

The present invention relates to fibers and nonwovens made from plasticized polyolefin compositions comprising a polyolefin and a non-functionalized hydrocarbon plasticizer.

68 Claims, 8 Drawing Sheets

U.S. PATENT DOCUMENTS

| | | | |
|---|---|---|---|
| 4,153,582 A | 5/1979 | Puffr et al. | |
| 4,153,588 A | 5/1979 | Makowski et al. | |
| 4,153,594 A | 5/1979 | Wilson, Jr. | |
| 4,154,244 A | 5/1979 | Becker et al. | |
| 4,154,712 A | 5/1979 | Lee, Jr. | |
| 4,157,992 A | 6/1979 | Lundberg et al. | |
| 4,166,057 A | 8/1979 | Takemori | |
| 4,169,822 A | 10/1979 | Kutch et al. | |
| 4,170,586 A | 10/1979 | Clampitt et al. | |
| 4,175,069 A | 11/1979 | Brenner | |
| 4,189,411 A | 2/1980 | Haaf | |
| 4,210,570 A | 7/1980 | Trotter et al. | |
| 4,221,887 A | 9/1980 | Brenner et al. | |
| 4,229,337 A | 10/1980 | Brenner | |
| 4,237,083 A | 12/1980 | Young et al. | |
| 4,274,932 A | 6/1981 | Williams et al. | |
| 4,288,358 A | 9/1981 | Trotter et al. | |
| 4,288,480 A | 9/1981 | Grzywinski et al. | |
| 4,289,668 A | 9/1981 | Li | |
| 4,311,628 A | 1/1982 | Abdou-Sabet et al. | |
| 4,322,336 A | 3/1982 | Machurat et al. | |
| 4,325,850 A | 4/1982 | Mueller | |
| 4,327,007 A | 4/1982 | Vanderkooi, Jr. et al. | |
| 4,335,026 A | 6/1982 | Balinth | |
| 4,335,034 A | 6/1982 | Zuckerman et al. | |
| 4,340,513 A | 7/1982 | Moteki et al. | |
| 4,347,332 A | 8/1982 | Odorzynski et al. | |
| 4,352,823 A | 10/1982 | Cherukuri et al. | |
| 4,369,284 A | 1/1983 | Chen | |
| 4,379,169 A | 4/1983 | Reggio et al. | |
| 4,387,108 A | 6/1983 | Koch et al. | |
| 4,399,248 A | 8/1983 | Singh et al. | |
| 4,399,251 A | 8/1983 | Lee | |
| 4,403,005 A | 9/1983 | Nevins et al. | |
| 4,403,007 A | 9/1983 | Coughlin | |
| 4,409,345 A | 10/1983 | Moteki et al. | |
| 4,434,258 A | 2/1984 | Schumacher et al. | |
| 4,438,228 A | 3/1984 | Schenck | |
| 4,438,229 A | 3/1984 | Fujimori et al. | |
| 4,440,829 A | 4/1984 | Gerace et al. | |
| 4,450,250 A | 5/1984 | McConnell et al. | |
| 4,452,820 A | 6/1984 | D'Amelia et al. | |
| 4,459,311 A | 7/1984 | DeTora et al. | |
| 4,460,729 A | 7/1984 | Books | |
| 4,467,065 A | 8/1984 | Williams et al. | |
| 4,469,770 A | 9/1984 | Nelson | |
| 4,497,926 A | 2/1985 | Toy | |
| 4,504,604 A | 3/1985 | Pilkington et al. | |
| 4,518,615 A | 5/1985 | Cherukuri et al. | |
| 4,529,666 A | 7/1985 | Salzburg et al. | |
| 4,532,305 A | 7/1985 | Dickinson | |
| 4,536,537 A | 8/1985 | Klingensmith et al. | |
| 4,542,053 A | 9/1985 | Nevins et al. | |
| 4,551,507 A | 11/1985 | Haylock et al. | |
| 4,552,801 A | 11/1985 | Odorzynski et al. | |
| 4,579,901 A | 4/1986 | Allen et al. | |
| 4,584,215 A | 4/1986 | Bré et al. | |
| 4,616,052 A | 10/1986 | Habibullah | |
| 4,645,791 A | 2/1987 | Theodore et al. | |
| 4,659,757 A | 4/1987 | Okamoto et al. | |
| 4,663,220 A * | 5/1987 | Wisneski et al. | 428/221 |
| 4,666,959 A | 5/1987 | Weissberger et al. | |
| 4,666,968 A | 5/1987 | Downey et al. | |
| 4,670,341 A | 6/1987 | Lundsager | |
| 4,684,682 A | 8/1987 | Lee, Jr. | |
| 4,693,838 A | 9/1987 | Varma et al. | |
| 4,703,078 A * | 10/1987 | Maehara et al. | 524/476 |
| 4,726,989 A | 2/1988 | Mrozinski | |
| 4,745,143 A | 5/1988 | Mason et al. | |
| 4,746,388 A | 5/1988 | Inaba et al. | |
| 4,749,734 A | 6/1988 | Williams et al. | |
| 4,764,535 A | 8/1988 | Leicht | |
| 4,772,657 A | 9/1988 | Akiyama et al. | |
| 4,774,277 A | 9/1988 | Janac et al. | |
| 4,814,375 A | 3/1989 | Esposito | |
| 4,824,718 A | 4/1989 | Hwang | |
| 4,824,891 A | 4/1989 | Laurent et al. | |
| 4,833,172 A | 5/1989 | Schwarz et al. | |
| 4,833,195 A | 5/1989 | Adur et al. | |
| 4,840,988 A | 6/1989 | Nakayama et al. | |
| 4,845,137 A | 7/1989 | Williams et al. | |
| 4,853,428 A | 8/1989 | Theodore et al. | |
| 4,912,148 A * | 3/1990 | Kim et al. | 524/487 |
| 4,914,145 A | 4/1990 | Tohdoh et al. | |
| 4,919,992 A | 4/1990 | Blundell et al. | |
| 4,939,040 A | 7/1990 | Oreglia et al. | |
| 4,948,840 A | 8/1990 | Berta | |
| 4,952,457 A | 8/1990 | Cartier et al. | |
| 4,957,958 A | 9/1990 | Schleifstein | |
| 4,959,285 A | 9/1990 | Hoffmann | |
| 4,959,396 A | 9/1990 | Yankov et al. | |
| 4,959,402 A | 9/1990 | Williams et al. | |
| 4,960,820 A | 10/1990 | Hwo | |
| 4,995,884 A | 2/1991 | Ross et al. | |
| 4,996,094 A | 2/1991 | Dutt | |
| 5,026,756 A | 6/1991 | Arendt | |
| 5,028,647 A | 7/1991 | Haylock et al. | |
| 5,076,988 A | 12/1991 | Rifi | |
| 5,079,287 A | 1/1992 | Takeshi et al. | |
| 5,080,942 A | 1/1992 | Yau | |
| 5,091,454 A | 2/1992 | Arendt | |
| 5,093,197 A | 3/1992 | Howard et al. | |
| 5,105,038 A | 4/1992 | Chen et al. | |
| 5,106,899 A | 4/1992 | Maresca | |
| 5,116,626 A | 5/1992 | Synosky et al. | |
| 5,124,384 A | 6/1992 | Goldstein | |
| 5,149,736 A | 9/1992 | Gamarra | |
| 5,162,436 A | 11/1992 | Davis et al. | |
| 5,171,908 A | 12/1992 | Rudnick | |
| 5,173,317 A | 12/1992 | Hartman et al. | |
| 5,180,865 A | 1/1993 | Heilman et al. | |
| 5,206,276 A | 4/1993 | Lee, Jr. | |
| 5,230,843 A * | 7/1993 | Howard et al. | 264/41 |
| 5,231,128 A | 7/1993 | Nakata et al. | |
| 5,238,735 A | 8/1993 | Nagou et al. | |
| 5,240,966 A | 8/1993 | Iwasaki et al. | |
| 5,250,628 A | 10/1993 | Seguela et al. | |
| 5,256,717 A | 10/1993 | Stauffer et al. | |
| 5,258,419 A | 11/1993 | Rolando et al. | |
| 5,264,474 A | 11/1993 | Schleifstein et al. | |
| 5,278,220 A | 1/1994 | Vermeire et al. | |
| 5,286,500 A | 2/1994 | Synosky et al. | |
| 5,290,886 A | 3/1994 | Ellul | |
| 5,308,904 A | 5/1994 | Fujii et al. | |
| 5,312,856 A | 5/1994 | Hert et al. | |
| 5,324,580 A | 6/1994 | Allan et al. | |
| 5,340,848 A | 8/1994 | Asanuma et al. | |
| 5,356,709 A | 10/1994 | Woo et al. | |
| 5,356,948 A | 10/1994 | Payne, Jr. et al. | |
| 5,356,986 A | 10/1994 | Stewart et al. | |
| 5,376,716 A | 12/1994 | Nayak et al. | |
| 5,389,711 A | 2/1995 | Westbrook et al. | |
| 5,397,832 A | 3/1995 | Elul | |
| 5,409,041 A | 4/1995 | Yoshida et al. | |
| 5,424,080 A | 6/1995 | Synosky et al. | |
| 5,437,877 A | 8/1995 | Synosky et al. | |
| 5,442,004 A | 8/1995 | Sutherland et al. | |
| 5,459,193 A | 10/1995 | Anderson et al. | |
| 5,462,754 A | 10/1995 | Synosky et al. | |
| 5,462,981 A | 10/1995 | Bastioli et al. | |
| 5,489,646 A | 2/1996 | Tatman et al. | |
| 5,492,943 A | 2/1996 | Stempel | |
| 5,512,625 A | 4/1996 | Butterbach et al. | |
| 5,563,222 A | 10/1996 | Fukuda et al. | |

| | | | | | | |
|---|---|---|---|---|---|---|
| 5,569,693 | A | 10/1996 | Doshi et al. | 6,706,828 B2 | 3/2004 | DiMaio |
| 5,601,858 | A | 2/1997 | Mansukhani et al. | 6,720,376 B2 | 4/2004 | Itoh et al. |
| 5,624,986 | A | 4/1997 | Bunnelle et al. | 6,730,739 B2 | 5/2004 | Gipson |
| 5,663,230 | A | 9/1997 | Haman | 6,867,253 B1 | 3/2005 | Chen |
| 5,683,634 | A | 11/1997 | Fujii et al. | 6,905,760 B1 | 6/2005 | Mukohara et al. |
| 5,683,815 | A | 11/1997 | Leiss | 2001/0051265 A1 | 12/2001 | Williams et al. |
| 5,688,850 | A | 11/1997 | Wyffels | 2002/0049276 A1 | 4/2002 | Zwick |
| 5,700,312 | A | 12/1997 | Fausnight et al. | 2002/0077409 A1 | 6/2002 | Sakaki et al. |
| 5,726,239 | A | 3/1998 | Maes et al. | 2002/0147266 A1 | 10/2002 | Rawlinson et al. |
| 5,728,760 | A | 3/1998 | Rose et al. | 2002/0155267 A1 | 10/2002 | Bader |
| 5,736,197 | A | 4/1998 | Gaveske | 2002/0160137 A1 | 10/2002 | Varma |
| 5,739,200 | A | 4/1998 | Cheung et al. | 2002/0168518 A1 | 11/2002 | Bond et al. |
| 5,741,840 | A | 4/1998 | Lindquist et al. | 2002/0183429 A1 * | 12/2002 | Itoh et al. .................... 524/352 |
| 5,747,573 | A | 5/1998 | Ryan | 2003/0004266 A1 | 1/2003 | Kitazaki et al. |
| 5,776,589 | A | 7/1998 | Mace et al. | 2003/0032696 A1 | 2/2003 | Sime et al. |
| 5,786,418 | A | 7/1998 | Strelow et al. | 2003/0035951 A1 | 2/2003 | Magill et al. |
| 5,789,529 | A | 8/1998 | Matsumura et al. | 2003/0036577 A1 | 2/2003 | Hughes et al. |
| 5,804,630 | A | 9/1998 | Heyer et al. | 2003/0091803 A1 | 5/2003 | Bond et al. |
| 5,837,769 | A | 11/1998 | Graafland et al. | 2003/0092826 A1 | 5/2003 | Pearce |
| 5,849,806 | A | 12/1998 | St. Clair et al. | 2003/0134552 A1 | 7/2003 | Mehawej et al. |
| 5,869,555 | A | 2/1999 | Simmons et al. | 2003/0157859 A1 | 8/2003 | Ishikawa |
| 5,869,560 | A | 2/1999 | Kobayashi et al. | 2003/0181575 A1 | 9/2003 | Schmidt et al. |
| 5,869,562 | A | 2/1999 | Lindquist et al. | 2003/0181584 A1 | 9/2003 | Handlin, Jr. et al. |
| 5,872,183 | A | 2/1999 | Bonnet et al. | 2003/0187081 A1 | 10/2003 | Cui |
| 5,908,412 | A | 6/1999 | Beger | 2004/0034148 A1 | 2/2004 | Kelly et al. |
| 5,916,959 | A | 6/1999 | Lindquist et al. | 2004/0054040 A1 | 3/2004 | Lin et al. |
| 5,929,147 | A | 7/1999 | Pierick et al. | 2004/0063806 A1 | 4/2004 | Kaamakari |
| 5,939,483 | A | 8/1999 | Kueppers | 2004/0070653 A1 | 4/2004 | Mashita et al. |
| 5,948,557 | A | 9/1999 | Ondeck et al. | 2004/0106723 A1 * | 6/2004 | Yang et al. .................... 524/570 |
| 6,001,455 | A * | 12/1999 | Nishio et al. ............... 428/156 | 2004/0186214 A1 | 9/2004 | Li et al. |
| 6,017,986 | A | 1/2000 | Burton | 2004/0214498 A1 | 10/2004 | Webb et al. |
| 6,027,674 | A | 2/2000 | Yates | 2004/0260001 A1 | 12/2004 | Lin et al. |
| 6,045,922 | A | 4/2000 | Jannssen et al. | | | |
| 6,060,561 | A | 5/2000 | Wolfschwenger | FOREIGN PATENT DOCUMENTS | | |
| 6,077,899 | A | 6/2000 | Yatsuyanagi et al. | DE | 1 282 942 | 11/1968 |
| 6,084,031 | A | 7/2000 | Medsker et al. | DE | 1 961 981 | 7/1970 |
| 6,086,996 | A | 7/2000 | Rancich et al. | DE | 1 669 261 | 10/1970 |
| 6,127,444 | A | 10/2000 | Kadri | DE | 1 921 649 | 11/1970 |
| 6,143,818 | A | 11/2000 | Huang et al. | DE | 2 019 945 | 11/1971 |
| 6,190,769 | B1 | 2/2001 | Wang | DE | 2 108 293 | 8/1972 |
| 6,191,078 | B1 | 2/2001 | Shlomo et al. | DE | 1769723 | 10/1972 |
| 6,194,498 | B1 | 2/2001 | Anderson et al. | DE | 26 32 957 | 1/1978 |
| 6,197,285 | B1 * | 3/2001 | Kowalik et al. ............... 424/65 | DE | 32 44 499 | 6/1983 |
| 6,231,936 | B1 | 5/2001 | Kozimor et al. | DE | 37 35 502 | 5/1989 |
| 6,231,970 | B1 | 5/2001 | Anderson et al. | DE | 39 11 725 | 10/1990 |
| 6,271,294 | B1 | 8/2001 | Lasson et al. | DE | 44 17 191 | 8/1995 |
| 6,316,068 | B1 | 11/2001 | Masubuchi et al. | DE | 37 35 502 | 5/1998 |
| 6,326,426 | B1 | 12/2001 | Ellul | DE | 198 41 303 | 3/2000 |
| 6,329,468 | B1 | 12/2001 | Wang | DE | 19841303 | 3/2000 |
| 6,337,364 | B1 | 1/2002 | Sakaki et al. | EP | 0 039 126 | 11/1981 |
| 6,342,209 | B1 | 1/2002 | Patil et al. | EP | 0 083 049 | 7/1983 |
| 6,342,320 | B2 | 1/2002 | Liu et al. | EP | 0 087 294 | 8/1983 |
| 6,342,565 | B1 | 1/2002 | Cheng et al. | EP | 0 097 969 | 1/1984 |
| 6,348,563 | B1 | 2/2002 | Fukuda et al. | EP | 0 046 536 | 1/1985 |
| 6,362,252 | B1 | 3/2002 | Prutkin | EP | 0 050 548 | 1/1985 |
| 6,372,379 | B1 | 4/2002 | Samii et al. | EP | 0 058 331 | 6/1985 |
| 6,380,292 | B1 | 4/2002 | Gibes et al. | EP | 0 058 404 | 1/1986 |
| 6,384,115 | B1 | 5/2002 | Van Gysel et al. | EP | 0 210 733 | 2/1987 |
| 6,410,200 | B1 | 6/2002 | Williams et al. | EP | 0 214 112 | 3/1987 |
| 6,413,458 | B1 | 7/2002 | Pearce | EP | 0 217 516 | 4/1987 |
| 6,448,338 | B1 | 9/2002 | Born et al. | EP | 0 073 042 | 10/1987 |
| 6,451,915 | B1 | 9/2002 | Ellul et al. | EP | 0 255 735 | 2/1988 |
| 6,465,109 | B2 | 10/2002 | Ohtsuka | EP | 0 332 802 | 3/1988 |
| 6,482,281 | B1 | 11/2002 | Schmidt | EP | 0 315 363 | 10/1988 |
| 6,498,213 | B2 | 12/2002 | Jeong et al. | EP | 0 299 718 | 1/1989 |
| 6,509,128 | B1 | 1/2003 | Everaerts et al. | EP | 0 300 689 | 1/1989 |
| 6,531,214 | B2 | 3/2003 | Carter et al. | EP | 0300689 | 1/1989 |
| 6,538,066 | B2 | 3/2003 | Watanabe et al. | EP | 0 321 868 | 6/1989 |
| 6,559,232 | B2 | 5/2003 | Inoue et al. | EP | 0 322 169 | 6/1989 |
| 6,583,207 | B2 | 6/2003 | Stanhope et al. | EP | 0 315 481 | 8/1989 |
| 6,610,768 | B1 | 8/2003 | Jelenic et al. | EP | 0 343 943 | 11/1989 |
| 6,623,847 | B2 | 9/2003 | Yates | EP | 0 369 164 | 5/1990 |
| 6,639,020 | B1 | 10/2003 | Brant | | | |

| | | | | | | |
|---|---|---|---|---|---|---|
| EP | 0 389 695 | 10/1990 | | JP | 62223245 | 10/1987 |
| EP | 0 407 098 | 1/1991 | | JP | 88033788 | 2/1988 |
| EP | 0 431 475 | 6/1991 | | JP | 63251436 | 10/1988 |
| EP | 0 448 259 | 9/1991 | | JP | 01016638 | 1/1989 |
| EP | 0 476 401 | 3/1992 | | JP | 89017495 | 1/1989 |
| EP | 0 476 700 | 3/1992 | | JP | 01066253 | 3/1989 |
| EP | 0 513 470 | 11/1992 | | JP | 01/106628 | 4/1989 |
| EP | 0315363 | 1/1994 | | JP | 01282280 | 11/1989 |
| EP | 0 409 155 | 5/1994 | | JP | 02/038114 | 2/1990 |
| EP | 0 614 939 | 9/1994 | | JP | 2067344 | 3/1990 |
| EP | 0 617 077 | 9/1994 | | JP | 03037481 | 2/1991 |
| EP | 0 622 432 | 11/1994 | | JP | 03269036 | 11/1991 |
| EP | 0 428 153 | 3/1995 | | JP | 04 063 851 | 2/1992 |
| EP | 0 664 315 | 7/1995 | | JP | 04063851 | 2/1992 |
| EP | 0 677 548 | 10/1995 | | JP | 04 214709 | 5/1992 |
| EP | 0 682 074 | 11/1995 | | JP | 04257361 | 9/1992 |
| EP | 0 699 519 | 3/1996 | | JP | 05098088 | 4/1993 |
| EP | 0 716 124 | 6/1996 | | JP | 5112842 | 5/1993 |
| EP | 0 742 227 | 11/1996 | | JP | 06345893 | 12/1994 |
| EP | 0 755 970 | 1/1997 | | JP | 95085907 | 3/1995 |
| EP | 0 757 076 | 2/1997 | | JP | 07118492 | 5/1995 |
| EP | 0 801 104 | 10/1997 | | JP | 07214685 | 8/1995 |
| EP | 0 827 526 | 3/1998 | | JP | 07216143 | 8/1995 |
| EP | 0 886 656 | 12/1998 | | JP | 07247387 | 9/1995 |
| EP | 0 902 051 | 3/1999 | | JP | 07292167 | 11/1995 |
| EP | 0 940 433 | 9/1999 | | JP | 7292167 | 11/1995 |
| EP | 1 028 145 | 8/2000 | | JP | 96019286 | 1/1996 |
| EP | 1028145 | 8/2000 | | JP | 96019287 | 2/1996 |
| EP | 1 104 783 | 6/2001 | | JP | 08034862 | 3/1996 |
| EP | 1 138 478 | 10/2001 | | JP | 08246232 | 9/1996 |
| EP | 1 201 391 | 5/2002 | | JP | 08269417 | 10/1996 |
| EP | 1 211 285 | 6/2002 | | JP | 69029554 | 10/1996 |
| EP | 1 214 386 | 6/2002 | | JP | 08333557 | 12/1996 |
| EP | 1 252 231 | 10/2002 | | JP | 09-077901 | 3/1997 |
| EP | 1 331 258 | 7/2003 | | JP | 9087435 | 3/1997 |
| FR | 1 167 244 | 11/1958 | | JP | 09104801 | 4/1997 |
| FR | 1 536 425 | 7/1968 | | JP | 09208761 | 8/1997 |
| FR | 1566388 | 3/1969 | | JP | 9208761 | 8/1997 |
| FR | 1 580 539 | 9/1969 | | JP | 10017693 | 1/1998 |
| FR | 2094870 | 2/1972 | | JP | 10036569 | 2/1998 |
| FR | 2 110 824 | 6/1972 | | JP | 2730079 | 3/1998 |
| FR | 2.212.382 | 7/1974 | | JP | 10158971 | 6/1998 |
| FR | 2 256 207 | 12/1974 | | JP | 10279750 | 10/1998 |
| FR | 2 272 143 | 5/1975 | | JP | 10324783 | 12/1998 |
| FR | 2 590 910 | 6/1987 | | JP | 10325060 | 12/1998 |
| FR | 2 602 515 | 2/1988 | | JP | 11020397 | 1/1999 |
| GB | 964 845 | 7/1964 | | JP | 11 049 903 | 2/1999 |
| GB | 1044028 | 9/1966 | | JP | 11060789 | 3/1999 |
| GB | 1044502 | 10/1966 | | JP | 11080455 | 3/1999 |
| GB | 1044503 | 10/1966 | | JP | 11239587 | 9/1999 |
| GB | 1068783 | 5/1967 | | JP | 11291422 | 10/1999 |
| GB | 1166664 | 10/1969 | | JP | 2000154281 | 6/2000 |
| GB | 1252638 | 11/1971 | | JP | 2001064523 | 3/2001 |
| GB | 1 331988 | 9/1973 | | JP | 2001/106628 | 4/2001 |
| GB | 1329915 | 9/1973 | | JP | 2001131509 | 5/2001 |
| GB | 1452911 | 10/1976 | | JP | 2001233992 | 8/2001 |
| GB | 1458915 | 12/1976 | | JP | 2001279031 | 10/2001 |
| GB | 1559058 | 1/1980 | | JP | 2001342355 | 12/2001 |
| GB | 2 180 790 | 4/1987 | | JP | 2002/038114 | 2/2002 |
| GB | 2 195 642 | 4/1988 | | JP | 3325376 | 9/2002 |
| JP | 68013376 | 6/1943 | | JP | 3325377 | 9/2002 |
| JP | 69029554 | 12/1966 | | JP | 34 74677 | 9/2003 |
| JP | 44029554 | 12/1969 | | JP | 2004345327 | 12/2004 |
| JP | 50123148 | 9/1975 | | WO | WO80/00028 | 1/1980 |
| JP | 50151243 | 12/1975 | | WO | WO89/08681 | 9/1989 |
| JP | 76029170 | 3/1976 | | WO | WO91/18045 | 11/1991 |
| JP | 53023388 | 3/1978 | | WO | WO92/14784 | 9/1992 |
| JP | 53060383 | 5/1978 | | WO | WO92/16583 | 10/1992 |
| JP | 53102381 | 9/1978 | | WO | WO94/15014 | 7/1994 |
| JP | 56045932 | 4/1981 | | WO | WO95/13316 | 5/1995 |
| JP | 56095938 | 8/1981 | | WO | WO96/04419 | 2/1996 |
| JP | 60112439 | 6/1985 | | WO | WO96/11231 | 4/1996 |
| JP | 62132943 | 6/1987 | | WO | WO96/11232 | 4/1996 |

| | | |
|---|---|---|
| WO | WO96/26242 | 8/1996 |
| WO | WO97/10298 | 3/1997 |
| WO | WO97/19582 | 6/1997 |
| WO | WO 97/33921 | 9/1997 |
| WO | WO97/33921 | 9/1997 |
| WO | WO98/36783 | 8/1998 |
| WO | 98/44041 | 10/1998 |
| WO | WO98/44041 | 10/1998 |
| WO | WO98/46694 | 10/1998 |
| WO | WO 98/46694 | 10/1998 |
| WO | WO99/13016 | 3/1999 |
| WO | WO99/62987 | 12/1999 |
| WO | WO 00/66662 | 11/2000 |
| WO | WO 01/02263 | 1/2001 |
| WO | 01/18109 | 3/2001 |
| WO | WO 01/18109 | 3/2001 |
| WO | WO 01/43963 | 6/2001 |
| WO | 92/00354 | 1/2002 |
| WO | WO 02/10310 | 2/2002 |
| WO | 02/17973 | 3/2002 |
| WO | 02/18487 | 3/2002 |
| WO | WO 02/17973 | 3/2002 |
| WO | WO 02/018487 | 3/2002 |
| WO | WO 02/18487 | 3/2002 |
| WO | 02/31044 | 4/2002 |
| WO | WO 02/030194 | 4/2002 |
| WO | WO 02/30194 | 4/2002 |
| WO | WO 02/31044 | 4/2002 |
| WO | WO 02/062891 | 8/2002 |
| WO | WO 02/072689 | 9/2002 |
| WO | WO 02/074873 | 9/2002 |
| WO | WO 02/088238 | 11/2002 |
| WO | WO 02/100153 | 12/2002 |
| WO | WO 03/029379 | 4/2003 |
| WO | 03/48252 | 6/2003 |
| WO | WO 03/048252 | 6/2003 |
| WO | 03/060004 | 7/2003 |
| WO | 04/09699 | 7/2003 |
| WO | 03/066729 | 8/2003 |
| WO | 04/31292 | 9/2003 |
| WO | WO 04/009699 | 1/2004 |
| WO | 04/014997 | 2/2004 |
| WO | 04/20195 | 3/2004 |
| WO | 05/080495 | 9/2005 |

OTHER PUBLICATIONS

Rubber Technology Handbook, 1989, Werner Hoffman, Hanser Publishers, New York, pp. 294-305.
Rudnick and Shubkin (Synthetic Lubricants and High-Performance Functional Fluids, Second edition, Rudnick, Shubkin, eds., Marcel Dekker, Inc. New York, 1999, pp. 1-52, 357-392.
Additives for Plastics, J. Stepek, H. Daoust, 1983, Springer Verlag, New York, pp. 6-69.
Abstract of DE 37 35 502, published on May 3, 1998, entitled "Crosslinkable compsns. resistant to damage in electron beam appts.—contain elastomeric and partly crystalline polymers, fillers, and antioxidant".

Abstract of EP 0 801 104, published on Oct. 15, 1997, entitled, "Use of atactic polypropylene to improve stability against ionising radiation".
Abstract of JP 8253754, published on Oct. 1, 1996, entitled, "Method for Foaming Reactive Hot-Melt Polyurethane Adhesive".
PCT Written Opinion, Jan. 7, 2004, 2002B107B.
"Swelling Interaction, Plasticization, and Antioxidant extraction Between Fiber Optic Cable Gels and Polyolefins" B. G. Risch, Ph.D., SPE-ANTEC, 1999.
"Use of "Clean " Paraffinic Processing Oils to Improve TPE Properties", B. J. Gedeon et al., TPEs, 2000, pp. 157-170.
"Plasticizing of isotactic polypropylene upon addition of hydrocarbon oils", K. Nitta et al., e-Polymers, No. 021, 2004, pp. 1-11.
"The Effect of Oil Type and Content on the Rheological, Mechanical and Thermal Properties of a Polyolefinic Based Thermoplastic Elastomer", McShane,et al. SPE-ANTEC, 2002.
Abstract of "Plasticizing Characteristics of High-Density Polyethylene" Wu et al., Suliao, 1988, 17 (4), 3-8.
Abstract of "Effect of Technological Additives on Properties of Thermoplastic vulcanizates Based on Ethylene Propylene Rubber and Polyolefins" Kanauzov et al., Kauchuk i Rezina, 2000, (4), 12-15.
Abstract of Polybutenes: a versatile modifier for plastics, J. D. Fotheringham, AddCon Asia (RAPRA), International Plastics Additives and Modifiers Conference, Singapore, Oct. 28-29, 1997.
Abstract of "Effect of Petroleum Plasticizers and Synthetic Oils on Rheological and service Properties of Polyolefins", M.D. Nasibova et al., Olefinov s Opyt. Z-dom, 1991 (14), 60-6.
"Rubber Chemicals and Additives", Rubber Technology Handbook, 1989, Werner Hoffman, Hanser Publishers, New York, pp. 294-305.
"Plasticizers", Additives for Plastics, J. Stepek, H. Daoust, 1983, Springer Verlag, New York, pp. 6-69.
"Lubricants and Other Processing Aids", Chemical Additives for the Plastics Industry, Properties, Applications, Toxicologies, Noyes Data Corporation, Park Ridge, NJ, 1987, pp. 107-116.
"Synthetic Lubricants and High-Performance Functional Fluids: Chemistry, Technology, and Commercial Importance", "Polybutenes", Second Edition, Rudnick, Shubkin, eds., Marcel Dekker, Inc. New York, 1999, pp. 1-52, 357-392.
Harper, Charles A., Fundamentals of Plastics and Elastomers, Handbook of Plastics, Elastomers, and Composites, Chapter One, pp. 1.13-1.14, 2nd ed., 1992.
Khungar, S.L.; "Flexible Films of Polypropylene Plasticized with Polybutenes", Amoco Chemicals, pp. 2992-2996, 1996.
Pratt, C. F. et al.; "Control of Phase Separation and Voiding in Oil-Filled Polypropylene", Journal of Applied Polymers Science, Vo. 18, pp. 3621-3631, 1974.
Gedeon, B. et al.; "Use of "Clean " Paraffinic Processing Oils to Improve", Paralux Articles, Presented at TPEs 2000, pp. 1-10, 2000.

* cited by examiner

Fig. 1 E' of Plasticized Propylene Polymers

Fig. 2 Tan δ of Plasticized Propylene Polymers

Tan δ of Plasticized Propylene Copolymers

Tan δ of Plasticized Propylene Impact Copolymers

DSC Melting of Plasticized Metallocene Propylene Polymers

DSC Crystallization of Plasticized Metallocene Propylene Polymers

DSC Melting of Plasticized Propylene Random Copolymers

DSC Crystallization of Plasticized Propylene Random Copolymers

DSC Melting of Plasticized Propylene Impact Copolymers

DSC Crystallization of Plasticized Propylene Impact Copolymers

Shear Viscosity of Plasticized Metallocene Propylene Homopolymers

Shear Viscosity of Plasticized Propylene Random Copolymers

Shear Viscosity of Plasticized Propylene Impact Copolymers

Molecular Weight Distribution of Plasticized Propylene Homopolymers

US 7,271,209 B2

FIBERS AND NONWOVENS FROM PLASTICIZED POLYOLEFIN COMPOSITIONS

PRIORITY CLAIM

This application is a continuation in part of U.S. Ser. No. 10/640,435, filed Aug. 12, 2003 which claims priority from U.S. Ser. No. 60/402,665 filed on Aug. 12, 2002 and this application is a continuation in part of U.S. Ser. No. 10/634, 351 filed Aug. 4, 2003 which claims priority from U.S. Ser. No. 60/402,665 filed on Aug. 12, 2002.

FIELD OF THE INVENTION

The present invention relates fibers and nonwoven articles producd from plasticized polyolefins comprising a polyolefin and a non-functionalized plasticizer.

BACKGROUND OF THE INVENTION

Polyolefins are useful in any number of everyday articles. However, one drawback to many polyolefins, especially propylene homopolymers and some propylene copolymers, is their relatively high glass transition temperature. This characteristic makes these polyolefins brittle, especially at low temperatures. Many applications of polyolefins benefit from having useful properties over a broad range of temperatures; consequently, there is a need to provide polyolefins that can maintain desirable characteristics such as high or low temperature performance, etc., while maintaining or improving upon the impact strength and toughness at lower temperatures. In particular, it would be advantageous to provide a propylene polymer possessing improved toughness and or high use temperature without sacrificing its other desirable properties.

Addition of a plasticizer or other substance to a polyolefin is one way to improve such properties as impact strength and toughness. Some patent disclosures directed to such an end are U.S. Pat. Nos. 4,960,820; 4,132,698; 3,201,364; WO 02/31044; WO 01/18109 A1; and EP 0 300 689 A2. These disclosures are directed to polyolefins and elastomers blended with functionalized plasticizers. The functionalized plasticizers are materials such as mineral oils which contain aromatic groups, and high (greater than –20° C.) pour point compounds. Use of these compounds typically does not preserve the transparency of the polyolefin, and impact strength is often not improved.

WO 98/44041 discloses plastic based sheet like material for a structure, especially a floor covering, which contains in a blend a plastic matrix comprising a chlorine free polyolefin or mixture of polyolefins and a plasticizer characterized in that the plasticizer is an oligomeric polyalphaolefin type substance.

Other background references include EP 0 448 259 A, EP 1 028 145 A, U.S. Pat. Nos. 4,073,782, and 3,415,925.

What is needed is a polyolefin with lower flexural modulus, lower glass transition temperature, and higher impact strength near and below 0° C., while not materially influencing the peak melting temperature of the polyolefin, the polyolefin crystallization rate, or its clarity, and with minimal migration of plasticizer to the surface of fabricated articles. A plasticized polyolefin according to this invention can fulfill these needs. More specifically, there is a need for a plasticized polypropylene that can be used in such applications as food containers and toys.

Likewise, a plasticized polyolefin with improved softness, better flexibility (lower flexural modulus), a depressed glass transition temperature, and or improved impact strength (improved Gardner impact) at low temperatures (below 0° C.), where the melting temperature of the polyolefin, the polyolefin crystallization rate, or its clarity are not influenced and with minimal migration of the plasticizer to the surface of articles made therefrom is desirable.

It would be particularly desirable to plasticize polyolefins by using a simple, non-reactive compound such as a paraffin. However, it has been taught that aliphatic or paraffinic compounds would impair the properties of polyolefins, and was thus not recommended. (See, e.g., CHEMICAL ADDITIVES FOR PLASTICS INDUSTRY 107-116 (Radian Corp., Noyes Data Corporation, NJ 1987); WO 01/18109 A1).

Mineral oils, which have been used as extenders, softeners, and the like in various applications, consist of thousands of different compounds, many of which are undesirable in a lubricating system. Under moderate to high temperatures these compounds can volatilize and oxidize, even with the addition of oxidation inhibitors.

Certain mineral oils, distinguished by their viscosity indices and the amount of saturates and sulfur they contain, have been classified as Hydrocarbon Basestock Group I, II or III by the American Petroleum Institute (API). Group I basestocks are solvent refined mineral oils. They contain the most unsaturates and sulfur and have the lowest viscosity indices. They define the bottom tier of lubricant performance. Group I basestocks are the least expensive to produce, and they currently account for abut 75 percent of all basestocks. These comprise the bulk of the "conventional" basestocks. Groups II and III are the High Viscosity Index and Very High Viscosity Index basestocks. They are hydroprocessed mineral oils. The Group III oils contain less unsaturates and sulfur than the Group I oils and have higher viscosity indices than the Group II oils do. Additional basestocks, named Groups IV and V, are also used in the basestock industry. Rudnick and Shubkin (*Synthetic Lubricants and High-Performance Functional Fluids*, Second edition, Rudnick, Shubkin, eds., Marcel Dekker, Inc. New York, 1999) describe the five basestock Groups as typically being:

Group I—mineral oils refined using solvent extraction of aromatics, solvent dewaxing, hydrofining to reduce sulfur content to produce mineral oils with sulfur levels greater than 0.03 weight %, saturates levels of 60 to 80% and a viscosity index of about 90;

Group II—mildly hydrocracked mineral oils with conventional solvent extraction of aromatics, solvent dewaxing, and more severe hydrofining to reduce sulfur levels to less than or equal to 0.03 weight % as well as removing double bonds from some of the olefinic and aromatic compounds, saturate levels are greater than 95-98% and VI is about 80-120;

Group III—severely hydrotreated mineral oils with saturates levels of some oils virtually 100%, sulfur contents are less than or equal to 0.03 weight % (preferably between 0.001 and 0.01%) and VI is in excess of 120;

Group IV—poly-alpha-olefins-hydrocarbons manufactured by the catalytic oligomerization of linear olefins having 6 or more carbon atoms. In industry however, the Group IV basestocks are referred to as "polyalphaolefins" are generally thought of as a class of synthetic basestock fluids produced by oligomerizing $C_4$ and greater alphaolefins; and Group V—esters, polyethers, polyalkylene glycols, and includes all other basestocks not included in Groups I, II, III and IV.

Other references of interest include: U.S. Pat. Nos. 5,869,555, 4,210,570, 4,110,185, GB 1,329,915, U.S. Pat. Nos. 3,201,364, 4,774,277, JP01282280, FR2094870, JP69029554, *Rubber Technology Handbook*, Werner Hoffman, Hanser Publishers, New York, 1989, pg294-305, *Additives for Plastics*, J. Stepek, H. Daoust, Springer Verlag, New York, 1983, pg-6-69.

U.S. Pat. No. 4,536,537 discloses blends of LLDPE (UC 7047), polypropylene (5520) and Synfluid 2CS, 4CS, or 6CS having a viscosity of 4.0 to 6.5 cSt at 100° F./38° C., however the Synfluid 4CS and 8CS are reported to "not work" (col 3, ln 12).

SUMMARY OF THE INVENTION

This invention relates to fibers and nonwoven articles comprising plasticized polyolefin compositions comprising one or more polyolefins and one or more non-functionalized plasticizers ("NFP").

DEFINITIONS

Figure 1:
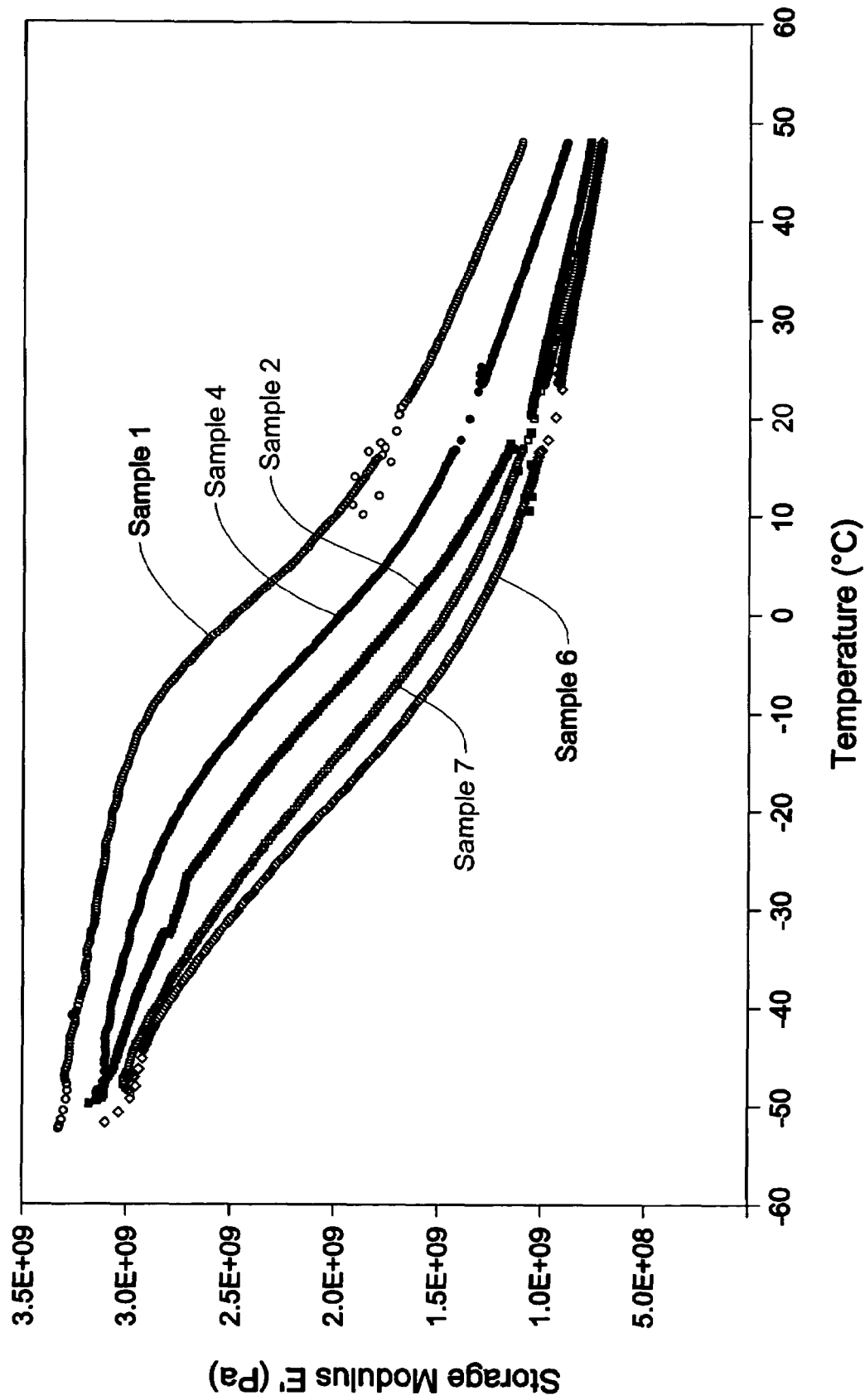
FIG. 1 is a graphical representation of the Storage Modulus (E') as a function of temperature for various plasticized propylene homopolymer examples cited herein.

For purposes of this invention and the claims thereto when a polymer or oligomer is referred to as comprising an olefin, the olefin present in the polymer or oligomer is the polymerized or oligomerized form of the olefin, respectively. Likewise the use of the term polymer is meant to encompass homopolymers and copolymers. In addition the term copolymer includes any polymer having 2 or more monomers. Thus, as used herein, the term "polypropylene" means a polymer made of at least 50% propylene units, preferably at least 70% propylene units, more preferably at least 80% propylene units, even more preferably at least 90% propylene units, even more preferably at least 95% propylene units or 100% propylene units.

For purposes of this invention an oligomer is defined to have an Mn of less than 21,000 g/mol, preferably less than 20,000 g/mol, preferably less than 19,000 g/mol, preferably less than 18,000 g/mol, preferably less than 16,000 g/mol, preferably less than 15,000 g/mol, preferably less than 13,000 g/mol, preferably less than 10,000 g/mol, preferably less than 5000 g/mol, preferably less than 3000 g/mol.

For purposes of this invention and the claims thereto Group I, II, and III basestocks are defined to be mineral oils having the following properties:

|  | Saturates (wt %) | Sulfur (wt %) | Viscosity Index |
|---|---|---|---|
| Group I | <90 &/or | >0.03% & | ≧80 & <120 |
| Group II | ≧90 & | ≦0.03% & | ≧80 & <120 |
| Group III | ≧90 & | ≦0.03% & | ≧120 |

DETAILED DESCRIPTION OF THE INVENTION

This invention relates to articles formed from plasticized polyolefin compositions comprising one or more polyolefins and one or more non-functionalized plasticizers ("NFP").

Typically, the polyolefin(s) are present in the compositions of the present invention at from 40 wt % to 99.9 wt % (based upon the weight of the polyolefin and the NFP) in one embodiment, and from 50 wt % to 99 wt % in another embodiment, and from 60 wt % to 98 wt % in yet another embodiment, and from 70 wt % to 97 wt % in yet another embodiment, and from 80 wt % to 97 wt % in yet another embodiment, and from 90 wt % to 98 wt % in yet another embodiment, wherein a desirable range may be any combination of any upper wt % limit with any lower wt % limit described herein.

In another embodiment the plasticized polyolefin comprises polypropylene present at 40 to 99.99 weight %, alternately 50 to 99 weight %, alternately 60 to 99 weight %, alternately 70 to 98 weight %, alternately 80 to 97 weight %, alternately 90 to 96 weight %, and the NFP is present at 60 to 0.01 weight %, alternately 50 to 1 weight %, alternately 40 to 1 weight %, alternately 30 to 2 weight %, alternately 20 to 3 weight %, alternately 10 to 4 weight %, based upon the weight of the polypropylene and the NFP.

In another embodiment the plasticized polyolefin comprises polybutene present at 50 to 99.99 weight %, alternately 60 to 99 weight %, alternately 70 to 98 weight %, alternately 80 to 97 weight %, alternately 90 to 96 weight %, and the NFP is present at 50 to 0.01 weight %, alternately 40 to 1 weight %, alternately 30 to 2 weight %, alternately 20 to 3 weight %, alternately 10 to 4 weight %, based upon the weight of the polybutene and the NFP.

In another embodiment the polyolefin comprises polypropylene and or polybutene and NFP is present at 0.01 to 50 weight %, more preferably 0.05 to 45 weight %, more preferably 0.5 to 40 weight %, more preferably 1 to 35 weight %, more preferably 2 to 30 weight %, more preferably 3 to 25 weight %, more preferably 4 to 20 weight %, more preferably 5 to 15 weight %, based upon the weight of the polypropylene and the NFP. In another embodiment, the NFP is present at 1 to 15 weight %, preferably 1 to 10 weight %, based upon the weight of the polypropylene and or polybutene and the NFP.

In another embodiment the NFP is present at more than 3 weight %, based upon the weight of the polyolefin and the NFP.

For purposes of this invention and the claims thereto the amount of NFP in a given composition is determined by the Extraction method described below. The CRYSTAF method also described is for comparison purposes.

For purposes of this invention and the claims thereto when melting point is referred to and there is a range of melting temperatures, the melting point is defined to be the peak melting temperature from a differential scanning calorimetry (DSC) trace as described below.

Non-Functionalized Plasticizer

The polyolefin compositions of the present invention include a non-functionalized plasticizer ("NFP"). The NFP of the present invention is a compound comprising carbon and hydrogen, and does not include to an appreciable extent functional groups selected from hydroxide, aryls and substituted aryls, halogens, alkoxys, carboxylates, esters, carbon unsaturation, acrylates, oxygen, nitrogen, and carboxyl. By "appreciable extent", it is meant that these groups and compounds comprising these groups are not deliberately added to the NFP, and if present at all, are present at less than 5 wt % by weight of the NFP in one embodiment, more preferably less than 4 weight %, more preferably less than 3 weight %, more preferably less than 2 weight %, more preferably less than 1 weight %, more preferably less than 0.7 weight %, more preferably less than 0.5 weight %, more preferably less than 0.3 weight %, more preferably less than 0.1 weight %, more preferably less than 0.05 weight %, more preferably less than 0.01 weight %, more preferably less than 0.001 weight %, based upon the weight of the NFP.

In one embodiment, the NFP comprises $C_6$ to $C_{200}$ paraffins, and $C_8$ to $C_{100}$ paraffins in another embodiment. In another embodiment, the NFP consists essentially of $C_6$ to $C_{200}$ paraffins, and consists essentially of $C_8$ to $C_{100}$ paraffins in another embodiment. For purposes of the present invention and description herein, the term "paraffin" includes all isomers such as n-paraffins, branched paraffins, isoparaffins, and may include cyclic aliphatic species, and blends thereof, and may be derived synthetically by means known in the art, or from refined crude oil in such a way as to meet the requirements described for desirable NFPs described herein. It will be realized that the classes of materials described herein that are useful as NFPs can be utilized alone or admixed with other NFPs described herein in order to obtain desired properties.

This invention further relates to plasticized polyolefin compositions comprising one or more polyolefins and one or more non-functionalized plasticizers ("NFP's") where the non-functionalized plasticizer has a kinematic viscosity ("KV") of 2 cSt or less at 100° C., preferably 1.5 cSt or less, preferably 1.0 cSt or less, preferably 0.5 cSt or less (as measured by ASTM D 445). In another embodiment the NFP having a KV of 2 cSt or less at 100° C. also has a glass transition temperature (Tg) that cannot be determined by ASTM E 1356 or if it can be determined then the Tg according to ASTM E 1356 is less than 30° C. preferably less than 20° C., more preferably less than 10° C., more preferably less than 0° C., more preferably less than −5° C., more preferably less than −10° C., more preferably less than −15° C.

In another embodiment the NFP having a KV of 2 cSt or less at 100° C., optionally having a glass transition temperature (Tg) that cannot be determined by ASTM ASTM E 1356 or if it can be determined then the Tg according to ASTM E 1356 is less than 30° C. preferably less than 20° C., more preferably less than 10° C., more preferably less than 0° C., more preferably less than −5° C., has one or more of the following properties:

1. a distillation range as determined by ASTM D 86 having a difference between the upper temperature and the lower temperature of 40° C. or less, preferably 35° C. or less, preferably 30° C. or less, preferably 25° C. or less, preferably 20° C. or less, preferably 15° C. or less, preferably 10° C. or less, preferably between 6 and 40° C., preferably between 6 and 30° C.; and or
2. an initial boiling point as determined by ASTM D 86 greater than 100° C., preferably greater than 110° C., preferably greater than 120° C., preferably greater than 130° C., preferably greater than 140° C., preferably greater than 150° C., preferably greater than 160° C., preferably greater than 170° C., preferably greater than 180° C., preferably greater than 190° C., preferably greater than 200° C., preferably greater than 210° C., preferably greater than 220° C., preferably greater than 230° C., preferably greater than 240° C.; and or
3. a pour point of 10° C. or less (as determined by ASTM D 97), preferably 0° C. or less, preferably −5° C. or less, preferably −15° C. or less, preferably −40° C. or less, preferably −50° C. or less, preferably −60° C. or less; and or
4. a specific gravity (ASTM D 4052, 15.6/15.6° C.) of less than 0.88, preferably less than 0.85, preferably less than 0.80, preferably less than 0.75, preferably less than 0.70, preferably from 0.65 to 0.88, preferably from 0.70 to 0.86, preferably from 0.75 to 0.85, preferably from 0.79 to 0.85, preferably from 0.800 to 0.840; and or
5. a final boiling point as determined by ASTM D 86 of from 115° C. to 500° C., preferably from 200° C. to 450° C., preferably from 250° C. to 400° C.; and or
6. a weight average molecular weight (Mw) between 2,000 and 100 g/mol, preferably between 1500 and 150, more preferably between 1000 and 200; and or
7. a number average molecular weight (Mn) between 2,000 and 100 g/mol, preferably between 1500 and 150, more preferably between 1000 and 200; and or
8. a flash point as measured by ASTM D 56 of −30 to 150° C., and or
9. a dielectric constant at 20° C. of less than 3.0, preferably less than 2.8, preferably less than 2.5, preferably less than 2.3, preferably less than 2.1; and or
10. a density (ASTM 4052, 15.6/15.6° C.) of from 0.70 to 0.83 g/cm$^3$; and or 11. a viscosity (ASTM 445, 25° C.) of from 0.5 to 20 cSt at 25° C.; and or
12. a carbon number of from 6 to 150, preferably from 7 to 100, preferably 10 to 30, preferably 12 to 25.

In certain embodiments of the invention the NFP having a KV of 2 cSt or less at 100° C. preferably comprises at least 50 weight %, preferably at least 60 wt %, preferably at least 70 wt %, preferably at least 80 wt %, preferably at least 90 wt %, preferably at least 95 wt % preferably 100 wt % of $C_6$ to $C_{150}$ isoparaffins, preferably $C_6$ to $C_{100}$ isoparaffins, preferably $C_6$ to $C_{25}$ isoparaffins, more preferably $C_8$ to $C_{20}$ isoparaffins. By isoparaffin is meant that the paraffin chains possess $C_1$ to $C_{10}$ alkyl branching along at least a portion of each paraffin chain. More particularly, the isoparaffins are saturated aliphatic hydrocarbons whose molecules have at least one carbon atom bonded to at least three other carbon atoms or at least one side chain (i.e., a molecule having one or more tertiary or quaternary carbon atoms), and preferably wherein the total number of carbon atoms per molecule is in the range between 6 to 50, and between 10 and 24 in another embodiment, and from 10 to 15 in yet another embodiment. Various isomers of each carbon number will typically be present. The isoparaffins may also include cycloparaffins with branched side chains, generally as a minor component of the isoparaffin. Preferably the density (ASTM 4052, 15.6/15.6° C.) of these isoparaffins ranges from 0.70 to 0.83 g/cm$^3$; the pour point is −40° C. or less, preferably −50° C. or less, the viscosity (ASTM 445, 25° C.) is from 0.5 to 20 cSt at 25° C.; and the average molecular weights in the range of 100 to 300 g/mol. Suitable isoparaffins are commercially available under the tradename ISOPAR (ExxonMobil Chemical Company, Houston Tex.), and are described in, for example, U.S. Pat. Nos. 6,197,285, 3,818,105 and 3,439,088, and sold commercially as ISOPAR series of isoparaffins, some of which are summarized in Table 1.

TABLE 1

ISOPAR Series Isoparaffins

| Name | distillation range (° C.) | pour point (° C.) | Avg. Specific Gravity | Viscosity @ 25° C. (cSt) | saturates and aromatics (wt %) |
|---|---|---|---|---|---|
| ISOPAR E | 117-136 | −63 | 0.72 | 0.85 | <0.01 |
| ISOPAR G | 161-176 | −57 | 0.75 | 1.46 | <0.01 |
| ISOPAR H | 178-188 | −63 | 0.76 | 1.8 | <0.01 |
| ISOPAR K | 179-196 | −60 | 0.76 | 1.85 | <0.01 |
| ISOPAR L | 188-207 | −57 | 0.77 | 1.99 | <0.01 |
| ISOPAR M | 223-254 | −57 | 0.79 | 3.8 | <0.01 |
| ISOPAR V | 272-311 | −63 | 0.82 | 14.8 | <0.01 |

In another embodiment, the isoparaffins are a mixture of branched and normal paraffins having from 6 to 50 carbon atoms, and from 10 to 24 carbon atoms in another embodiment, in the molecule. The isoparaffin composition has a ratio of branch paraffin to n-paraffin ratio (branch paraffin: n-paraffin) ranging from 0.5:1 to 9:1 in one embodiment, and from 1:1 to 4:1 in another embodiment. The isoparaffins of the mixture in this embodiment contain greater than 50 wt % (by total weight of the isoparaffin composition) monomethyl species, for example, 2-methyl, 3-methyl, 4-methyl, 5-methyl or the like, with minimum formation of branches with substituent groups of carbon number greater than 1, such as, for example, ethyl, propyl, butyl or the like, based on the total weight of isoparaffins in the mixture. In one embodiment, the isoparaffins of the mixture contain greater than 70 wt % of the mono-methyl species, based on the total weight of the isoparaffins in the mixture. The isoparaffinic mixture boils within a range of from 100° C. to 350° C. in one embodiment, and within a range of from 110° C. to 320° C. in another embodiment. In preparing the different grades, the paraffinic mixture is generally fractionated into cuts having narrow boiling ranges, for example, 35° C. boiling ranges. These branch paraffin/n-paraffin blends are described in, for example, U.S. Pat. No. 5,906,727.

Other suitable isoparaffins are also commercial available under the trade names SHELLSOL (by Shell), SOLTROL (by Chevron Phillips) and SASOL (by Sasol Limited). SHELLSOL is a product of the Royal Dutch/Shell Group of Companies, for example Shellsol TM (boiling point=215-260° C.). SOLTROL is a product of Chevron Phillips Chemical Co. LP, for example SOLTROL 220 (boiling point=233-280° C.). SASOL is a product of Sasol Limited (Johannesburg, South Africa), for example SASOL LPA-210, SASOL-47 (boiling point=238-274° C.).

In certain embodiments of the invention the NFP having a KV of 2 cSt or less at 100° C. preferably comprises at least 50 weight %, preferably at least 60 wt %, preferably at least 70 wt %, preferably at least 80 wt %, preferably at least 90 wt %, preferably at least 95 wt % preferably 100 wt % of $C_5$ to $C_{25}$ n-paraffins, preferably $C_5$ to $C_{20}$ n-paraffins, preferably $C_5$ to $C_{15}$ n-paraffins having less than 0.1%, preferably less than 0.01% aromatics. In preferred embodiments the n-paraffins have a distillation range of 30° C. or less, preferably 20° C. or less, and or an initial boiling point greater than 150° C., preferably greater than 200° C., and or a specific gravity of from 0.65 to 0.85, preferably from 0.70 to 0.80, preferably from 0.75 to 0.80, and or a flash point greater than 60° C., preferably greater than 90° C., preferably greater than 100° C., preferably greater than 120° C.

Suitable n-paraffins are commercially available under the tradename NORPAR (ExxonMobil Chemical Company, Houston Tex.), and are sold commercially as NORPAR series of n-paraffins, some of which are summarized in Table 1a.

TABLE 1a

NORPAR Series n-paraffins

| Name | distillation range (° C.) | pour point (° C.) | Avg. Specific Gravity) | Viscosity @ 25° C. (cSt) | saturates and aromatics (wt %) |
|---|---|---|---|---|---|
| NORPAR 12 | 189-218 | | 0.75 | 1.6 | <0.01 |
| NORPAR 13 | 222-242 | | 0.76 | 2.4 | <0.01 |
| NORPAR 14 | 241-251 | | 0.77 | 2.8 | <0.01 |
| NORPAR 15 | 249-274 | 7 | 0.77 | 3.3 | <0.01 |

In certain embodiments of the invention the NFP having a KV of 2 cSt or less at 100° C. preferably comprises at least 50 weight %, preferably at least 60 wt %, preferably at least 70 wt %, preferably at least 80 wt %, preferably at least 90 wt %, preferably at least 95 wt % preferably 100 wt % of a dearomaticized aliphatic hydrocarbon comprising a mixture of normal paraffins, isoparaffins and cycloparaffins. Typically they are a mixture of $C_4$ to $C_{25}$ normal paraffins, isoparaffins and cycloparaffins, preferably $C_5$ to $C_{18}$, preferably $C_5$ to $C_{12}$. They contain very low levels of aromatic hydrocarbons, preferably less than 0.1, preferably less than 0.01 aromatics. In preferred embodiments the dearomatized aliphatic hydrocarbons have a distillation range of 30° C. or less, preferably 20° C. or less, and or an initial boiling point greater than 110° C., preferably greater than 200° C., and or a specific gravity (15.6/15.6° C.) of from 0.65 to 0.85, preferably from 0.70 to 0.85, preferably from 0.75 to 0.85, preferably from 0.80 to 0.85 and or a flash point greater than 60° C., preferably greater than 90° C., preferably greater than 100° C., preferably greater than 110° C.

Suitable dearomatized aliphatic hydrocarbons are commercially available under the tradename EXXSOL (ExxonMobil Chemical Company, Houston Tex.), and are sold commercially as EXXSOL series of dearomaticized aliphatic hydrocarbons, some of which are summarized in Table 1b.

TABLE 1b

EXXSOL Series

| Name | distillation range (° C.) | pour point (° C.) | Avg. Specific Gravity | Viscosity @ 25° C. (cSt) | saturates and aromatics (wt %) |
|---|---|---|---|---|---|
| EXXSOL isopentane | | | 0.63 | 0.3 | – |
| EXXSOL methylpentane naphtha | 59-62 | | 0.66 | 0.5 | – |
| EXXSOL hexane fluid | 66-69 | | 0.67 | 0.5 | – |
| EXXSOL DSP 75/100 | 78-99 | | 0.72 | 0.6 | – |
| EXXSOL heptane fluid | 94-99 | | 0.70 | 0.6 | – |
| EXXSOL DSP 90/120 Naphtha | 98-115 | | 0.74 | | |
| EXXSOL DSP 115/145 Naphtha | 116-145 | | 0.75 | 0.8 | – |
| EXXSOL D Naphtha | 158-178 | | 0.77 | 1.2 | – |
| EXXSOL D 40 | 161-202 | | 0.79 | 1.4 | 0.3 |
| EXXSOL D 60 | 188-210 | | 0.80 | | 0.4 |
| EXXSOL D 80 | 208-234 | | 0.80 | 2.2 | 0.4 |
| EXXSOL D 95 | 224-238 | | 0.80 | 2.1 | 0.7 |
| EXXSOL D 110 | 249-268 | | 0.81 | 3.5 | 0.8 |
| EXXSOL D 130 | 282-311 | –45 | 0.83 | 6.9 | 1.5 |

This invention also relates to plasticized polyolefin compositions comprising one or more polyolefins, preferably polypropylene or polybutene, more preferably polypropylene and one or more non-functionalized plasticizers where the non-functionalized plasticizer comprises a polyalphaolefin comprising oligomers of $C_5$ to $C_{14}$ olefins (preferably $C_6$ to $C_{14}$, more preferably $C_8$ to $C_{12}$, more preferably $C_{10}$) having a Kinematic viscosity of 5 cSt or more at 100° C., preferably 10 cSt or more at 100° C. and a viscosity index of 120 or more, preferably 130 or more.

This invention also relates to plasticized polypropylene compositions comprising polypropylene and one or more non-functionalized plasticizers where the non-functionalized plasticizer comprises oligomers of $C_6$ to $C_4$ olefins having viscosity index of 120 or more, provided that when the plasticized composition comprises between 4 and 10 weight % of polyalphaolefin that is a hydrogenated, highly branched dimer of an alpha olefin having 8-12 carbon atoms, the composition does not comprises between 18 and 25 weight percent of a linear low density polyethylene having a density of 0.912 to 0.935 g/cc.

This invention also relates to plasticized polypropylene compositions comprising polypropylene and one or more non-functionalized plasticizers where the non-functionalized plasticizer comprises oligomers of $C_6$ to $C_{14}$ olefins having viscosity index of 120 or more, provided that the polyolefin does not comprises an impact copolymer of polypropylene and 40-50 weight % of an ethylene propylene rubber or provided that the composition does not comprise a random copolymer of propylene and ethylene.

In another embodiment the NFP comprises polyalphaolefins comprising oligomers of linear olefins having 5 to 14 carbon atoms, preferably 6 to 14 carbon atoms, more preferably 8 to 12 carbon atoms, more preferably 10 carbon atoms having a Kinematic viscosity of 5 or more at 100° C., preferably 10 or more at 100° C. (as measured by ASTM D 445); and preferably having a viscosity index ("VI"), as determined by ASTM D-2270 of 100 or more, preferably 110 or more, more preferably 120 or more, more preferably 130 or more, more preferably 140 or more; and/or having a pour point of –5° C. or less (as determined by ASTM D 97), more preferably –10° C. or less, more preferably –20° C. or less.

In another embodiment polyalphaolefin oligomers useful in the present invention comprise $C_{20}$ to $C_{1500}$ paraffins, preferably $C_{40}$ to $C_{1000}$ paraffins, preferably $C_{50}$ to $C_{750}$ paraffins, preferably $C_{50}$ to $C_{500}$ paraffins. The PAO oligomers are dimers, trimers, tetramers, pentamers, etc. of $C_5$ to $C_{14}$ α-olefins in one embodiment, and $C_6$ to $C_{12}$ α-olefins in another embodiment, and $C_8$ to $C_{12}$ α-olefins in another embodiment. Suitable olefins include 1-pentene, 1-hexene, 1-heptene, 1-octene, 1-nonene, 1-decene, 1-undecene and 1-dodecene. In one embodiment, the olefin is 1-decene, and the NFP is a mixture of dimers, trimers, tetramers and pentamers (and higher) of 1-decene. Preferred PAO's are described more particularly in, for example, U.S. Pat. Nos. 5,171,908, and 5,783,531 and in SYNTHETIC LUBRICANTS AND HIGH-PERFORMANCE FUNCTIONAL FLUIDS 1-52 (Leslie R. Rudnick & Ronald L. Shubkin, ed. Marcel Dekker, Inc. 1999).

PAO's useful in the present invention typically possess a number average molecular weight of from 100 to 21,000 in one embodiment, and from 200 to 10,000 in another embodiment, and from 200 to 7,000 in yet another embodiment, and from 200 to 2,000 in yet another embodiment, and from 200 to 500 in yet another embodiment. Preferred PAO's have viscosities in the range of 0.1 to 150 cSt at 100° C., and from 0.1 to 3000 cSt at 100° C. in another embodiment (ASTM 445). PAO's useful in the present invention typically have pour points of less than 0° C. in one embodiment, less than –10° C. in another embodiment, less than –20° C. in yet another embodiment, and less than –40° C. in yet another embodiment. Desirable PAO's are commercially available as SHF and SuperSyn PAO's (ExxonMobil Chemical Company, Houston Tex.), some of which are summarized in the Table 2 below.

TABLE 2

SHF and SuperSyn Series Polyalphaolefins

| PAO | specific gravity (15.6/15.6° C.) | Kinematic viscosity @ 100° C., cSt | VI | Pour Point, ° C. |
|---|---|---|---|---|
| SHF-20 | 0.798 | 1.68 | — | –63 |
| SHF-21 | 0.800 | 1.70 | — | –57 |
| SHF-23 | 0.802 | 1.80 | — | –54 |
| SHF-41 | 0.818 | 4.00 | 123 | –57 |
| SHF-61/63 | 0.826 | 5.80 | 133 | –57 |
| SHF-82/83 | 0.833 | 7.90 | 135 | –54 |
| SHF-101 | 0.835 | 10.0 | 136 | –54 |
| SHF-403 | 0.850 | 40.0 | 152 | –39 |
| SHF-1003 | 0.855 | 107 | 179 | –33 |
| SuperSyn 2150 | 0.850 | 150 | 214 | –42 |
| SuperSyn 2300 | 0.852 | 300 | 235 | –30 |
| SuperSyn 21000 | 0.856 | 1,000 | 305 | –18 |
| SuperSyn 23000 | 0.857 | 3,000 | 388 | –9 |

Other useful PAO's include those sold under the tradenames Synfluid™ available from ChevronPhillips Chemical Co. in Pasedena Tex., Durasyn™ available from BP Amoco Chemicals in London England, Nexbase™ available from Fortum Oil and Gas in Finland, Synton™ available from Crompton Corporation in Middlebury CN, USA, EMERY™ available from Cognis Corporation in Ohio, USA.

In other embodiments the PAO's have a Kinematic viscosity of 10 cSt or more at 100° C., preferably 30 cSt or more, preferably 50 cSt or more, preferably 80 cSt or more, preferably 110 or more, preferably 150 cSt or more, preferably 200 cSt or more, preferably 500 cSt or more, preferably 750 or more, preferably 1000 cSt or more, preferably 1500 cSt or more, preferably 2000 cSt or more, preferably 2500 or more. In another embodiment the PAO's have a kinematic viscosity at 100° C. of between 10 cSt and 3000 cSt, preferably between 10 cSt and 1000 cSt, preferably between 10 cSt and 40 cSt.

In other embodiments the PAO's have a viscosity index of 120 or more, preferably 130 or more, preferably 140 or more, preferably 150 or more, preferably 170 or more, preferably 190 or more, preferably 200 or more, preferably 250 or more, preferably 300 or more.

In a particularly preferred embodiment the PAO has a kinematic viscosity of 10 cSt or more at 100° C. when the polypropylene is RB 501 F, Hifax CA12A, or ADFLEX Q 100F, as these polymers are described in WO 98/44041.

This invention also relates to plasticized polyolefin compositions comprising one or more polyolefins and one or more non-functionalized plasticizers where the non-functionalized plasticizer comprises a high purity hydrocarbon fluid composition comprising a mixture of paraffins having 6 to 1500 carbon atoms, preferably 8 to 1000 carbon atoms, preferably 10 to 500 carbon atoms, preferably 12 to about 200 carbon atoms, preferably 14 to 150 carbon atoms, preferably 16 to 100 carbon atoms in the molecule. The hydrocarbon fluid composition has an isoparaffin:n-paraffin ratio ranging from about 0.5:1 to about 9:1, preferably from about 1:1 to about 4:1. The isoparaffins of the mixture contain greater than fifty percent, 50%, mono-methyl species, e.g., 2-methyl, 3-methyl, 4-methyl, $\geq$5-methyl or the like, with minimum formation of branches with substituent groups of carbon number greater than 1, i.e., ethyl, propyl, butyl or the like, based on the total weight of isoparaffins in the mixture. Preferably, the isoparaffins of the mixture contain greater than 70 percent of the mono-methyl species, based on the total weight of the isoparaffins in the mixture. These hydrocarbon fluids preferably have kinematic viscosities KV at 25° C. ranging from 1 to 100,000 cSt, preferably 10 cSt to 2000 cSt and, optionally low pour points typically below −20° C., more preferably below −30° C., more preferably ranging from about −20° C. to about −70° C. These hydrocarbon fluids preferably have viscosities KV at 40° C. ranging from 1 to 30,000 cSt, preferably 10 cSt to 2000 cSt and, optionally low pour points typically below −20° C., more preferably below −30° C., more preferably ranging from about −20° C. to about −70° C.

This invention also relates to plasticized polyolefin compositions comprising one or more polyolefins and one or more non-functionalized plasticizers where the non-functionalized plasticizer comprises a linear or branched paraffinic hydrocarbon composition having:

1. a number average molecular weight of 500 to 21,000 g/mol;
2. less than 10% sidechains having 4 or more carbons, preferably less than 8 weight %, preferably less than 5 weight %, preferably less than 3 weight %, preferably less than 2 weight %, preferably less than 1 weight %, preferably less than 0.5 weight %, preferably less than 0.1 weight %, preferably at less than 0.1 weight %, preferably at 0.001 weight %;
3. at least 1 or 2 carbon branches present at 15 weight % or more, preferably 20 weight % or more, preferably 25 weight % or more, preferably 30 weight % or more, preferably 35 weight % or more, preferably 40 weight % or more, preferably 45 weight % or more, preferably 50 weight % or more,
4. less than 2.5 weight % cyclic paraffins, preferably less than 2 weight %, preferably less than 1 weight %, preferably less than 0.5 weight %, preferably less than 0.1 weight %, preferably at less than 0.1 weight %, preferably at 0.001 weight %. In additional embodiments these NFP's have a kinematic viscosity 2 cSt or more at 100° C. and or a VI of 120 or more, preferably 130 or more, preferably 140 or more, preferably 150 or more, preferably 170 or more, preferably 190 or more, preferably 200 or more, preferably 250 or more, preferably 300 or more.

In another embodiment the NFP comprises a high purity hydrocarbon fluid composition which comprises a mixture of paraffins of carbon number ranging from about $C_8$ to $C_{20}$, has a molar ratio of isoparaffins: n-paraffins ranging from about 0.5:1 to about 9:1, the isoparaffins of the mixture contain greater than 50 percent of the mono-methyl species, based on the total weight of the isoparaffins of the mixture and wherein the composition has pour points ranging from about −20° F., to about −70° F., and kinematic viscosities at 25° C. ranging from about 1 cSt to about 10 cSt.

In another embodiment, the mixture of paraffins has a carbon number ranging from about $C_{10}$ to about $C_{16}$. In another embodiment, the mixture contains greater than 70 percent of the mono-methyl species. In another embodiment, the mixture boils at a temperature ranging from about 320° F. to about 650° F. In another embodiment, the mixture boils within a range of from about 350° F. to about 550° F. In another embodiment, the mixture comprises a mixture of paraffins of carbon number ranging from about $C_{10}$ to about $C_{16}$. In another embodiment, the mixture is of carbon numbers ranging from about $C_{10}$-$C_{16}$, the mixture contains greater than 70 percent of the mono-methyl species and boils within a range of from about 350° F. to about 550° F. In another embodiment, the mixture has a molar ratio of isoparaffins:n-paraffins ranging from about 1:1 to about 4:1. In another embodiment, the mixture is derived from a Fischer-Tropsch process. Such NFP's may be produced by the methods disclosed in U.S. Pat. No. 5,906,727.

Any of the NFP's may also be described by any number of, or any combination of, parameters described herein. In one embodiment, any of the NFP's of the present invention has a pour point (ASTM D97) of from less than 0° C. in one embodiment, and less than −5° C. in another embodiment, and less than −110° C. in another embodiment, less than −20° C. in yet another embodiment, less than −40° C. in yet another embodiment, less than −50° C. in yet another embodiment, and less than −60° C. in yet another embodiment, and greater than −120° C. in yet another embodiment, and greater than −200° C. in yet another embodiment, wherein a desirable range may include any upper pour point limit with any lower pour point limit described herein. In one embodiment, the NFP is a paraffin or other compound having a pour point of less than −30° C., and between −30° C. and −90° C. in another embodiment, in the viscosity range of from 0.5 to 200 cSt at 40° C. (ASTM D445-97). Most mineral oils, which typically include aromatic moieties and other functional groups, have a pour point of from 10° C. to −20° C. at the same viscosity range.

In another embodiment any NFP described herein may have a Viscosity Index of 90 or more, preferably 95 or more, more preferably 100 or more, more preferably 105 or more, more preferably 110 or more, more preferably 115 or more, more preferably 120 or more, more preferably 125 or more, more preferably 130 or more. In another embodiment the NFP has a VI between 90 and 400, preferably between 120 and 350.

Any NFP described herein may have a dielectric constant at 20° C. of less than 3.0 in one embodiment, and less than 2.8 in another embodiment, less than 2.5 in another embodiment, and less than 2.3 in yet another embodiment, and less than 2.1 in yet another embodiment. Polyethylene and polypropylene each have a dielectric constant (1 kHz, 23° C.) of at least 2.3 (CRC HANDBOOK OF CHEMISTRY AND PHYSICS (David R. Lide, ed. $82^d$ ed. CRC Press 2001).

In some embodiments, the NFP may have a kinematic viscosity (ASTM D445-97) of from 0.1 to 3000 cSt at 100° C., and from 0.5 to 1000 cSt at 100° C. in another embodiment, and from 1 to 250 cSt at 100° C. in another embodiment, and from 1 to 200 cSt at 100° C. in yet another embodiment, and from 10 to 500 cSt at 100° C. in yet another embodiment, wherein a desirable range may comprise any upper viscosity limit with any lower viscosity limit described herein. In other embodiments the NFP has a kinematic viscosity of less than 2 cSt at 100° C.

In some embodiments any NFP described herein may have a specific gravity (ASTM D 4052, 15.6/15.6° C.) of less than 0.920 in one embodiment, and less than 0.910 in another embodiment, and from 0.650 to 0.900 in another embodiment, and from 0.700 to 0.860, and from 0.750 to 0.855 in another embodiment, and from 0.790 to 0.850 in another embodiment, and from 0.800 to 0.840 in yet another embodiment, wherein a desirable range may comprise any upper specific gravity limit with any lower specific gravity limit described herein.

In other embodiments any NFP described herein may have a boiling point of from 100° C. to 500° C. in one embodiment, and from 200° C. to 450° C. in another embodiment, and from 250° C. to 400° C. in yet another embodiment. Further, the NFP preferably has a weight average molecular weight of less than 20,000 g/mol in one embodiment, and less than 10,000 g/mol in yet another embodiment, and less than 5,000 g/mol in yet another embodiment, and less than 4,000 g/mol in yet another embodiment, and less than 2,000 g/mol in yet another embodiment, and less than 500 g/mol in yet another embodiment, and greater than 100 g/mol in yet another embodiment, wherein a desirable molecular weight range can be any combination of any upper molecular weight limit with any lower molecular weight limit described herein.

In another embodiment the NFP comprises a Group III hydrocarbon basestock. Preferably the NFP comprises a mineral oil having a saturates levels of 90% or more, preferably 92% or more, preferably 94% or more, preferably 96% or more, preferably 98% or more, preferably 99% or more, and sulfur contents less than 0.03%, preferably between 0.001 and 0.01% and VI is in excess of 120, preferably 130 or more.

In some embodiments, polybutenes are useful as NFP's of the present invention. In one embodiment of the invention, the polybutene processing oil is a low molecular weight (less than 15,000 number average molecular weight; less than 60,000 weight average molecular weight) homopolymer or copolymer of olefin derived units having from 3 to 8 carbon atoms in one embodiment, preferably from 4 to 6 carbon atoms in another embodiment. In yet another embodiment, the polybutene is a homopolymer or copolymer of a $C_4$ raffinate. An embodiment of such low molecular weight polymers termed "polybutene" polymers is described in, for example, SYNTHETIC LUBRICANTS AND HIGH-PERFORMANCE FUNCTIONAL FLUIDS 357-392 (Leslie R. Rudnick & Ronald L. Shubkin, ed., Marcel Dekker 1999) (hereinafter "polybutene processing oil" or "polybutene"). Another preferred embodiment includes poly(n-butene) hydrocarbons. Preferred poly(n-butenes) have less than 15,000 number average molecular weight and less than 60,000 weight average molecular weight.

In another preferred embodiment, the polybutene is a copolymer of at least isobutylene derived units, 1-butene derived units, and 2-butene derived units. In one embodiment, the polybutene is a homopolymer, copolymer, or terpolymer of the three units, wherein the isobutylene derived units are from 40 to 100 wt % of the copolymer, the 1-butene derived units are from 0 to 40 wt % of the copolymer, and the 2-butene derived units are from 0 to 40 wt % of the copolymer. In another embodiment, the polybutene is a copolymer or terpolymer of the three units, wherein the isobutylene derived units are from 40 to 99 wt % of the copolymer, the 1-butene derived units are from 2 to 40 wt % of the copolymer, and the 2-butene derived units are from 0 to 30 wt % of the copolymer. In yet another embodiment, the polybutene is a terpolymer of the three units, wherein the isobutylene derived units are from 40 to 96 wt % of the copolymer, the 1-butene derived units are from 2 to 40 wt % of the copolymer, and the 2-butene derived units are from 2 to 20 wt % of the copolymer. In yet another embodiment, the polybutene is a homopolymer or copolymer of isobutylene and 1-butene, wherein the isobutylene derived units are from 65 to 100 wt % of the homopolymer or copolymer, and the 1-butene derived units are from 0 to 35 wt % of the copolymer.

Polybutene processing oils useful in the invention typically have a number average molecular weight (Mn) of less than 10,000 g/mol in one embodiment, less than 8000 g/mol in another embodiment, and less than 6000 g/mol in yet another embodiment. In one embodiment, the polybutene oil has a number average molecular weight of greater than 400 g/mol, and greater than 700 g/mol in another embodiment, and greater than 900 g/mol in yet another embodiment. A preferred embodiment can be a combination of any lower molecular weight limit with any upper molecular weight limit described herein. For example, in one embodiment of the polybutene of the invention, the polybutene has a number average molecular weight of from 400 g/mol to 10,000 g/mol, and from 700 g/mol to 8000 g/mol in another embodiment, and from 900 g/mol to 3000 g/mol in yet another embodiment. Useful viscosities of the polybutene processing oil ranges from 10 to 6000 cSt (centiStokes) at 100° C. in one embodiment, and from 35 to 5000 cSt at 100° C. in another embodiment, and is greater than 35 cSt at 100° C. in yet another embodiment, and greater than 100 cSt at 100° C. in yet another embodiment.

Commercial examples of useful polybutenes include the PARAPOL™ Series of processing oils (Infineum, Linden, N.J.), such as PARAPOL™ 450, 700, 950, 1300, 2400 and 2500 and the Infineum "C" series of polybutenes, including C9945, C9900, C9907, C9913, C9922, C9925 as listed below. The commercially available PARAPOL™ and Infineum Series of polybutene processing oils are synthetic liquid polybutenes, each individual formulation having a certain molecular weight, all formulations of which can be used in the composition of the invention. The molecular weights of the PARAPOL™ oils are from 420 Mn (PARAPOL™ 450) to 2700 Mn (PARAPOL™ 2500) as determined by gel permeation chromatography. The MWD of the PARAPOL™ oils range from 1.8 to 3 in one embodiment, and from 2 to 2.8 in another embodiment; the pour points of these polybutenes are less than 25° C. in one embodiment, less than 0° C. in another embodiment, and less than −10° C. in yet another embodiment, and between −80° C. and 25° C. in yet another embodiment; and densities (IP 190/86 at 20° C.) range from 0.79 to 0.92 g/cm³, and from 0.81 to 0.90 g/cm³ in another embodiment.

Below, Tables 3 and 3a shows some of the properties of the PARAPOL™ oils and Infineum oils useful in embodiments of the present invention, wherein the viscosity was determined as per ASTM D445-97, and the number average molecular weight ($M_n$) by gel permeation chromatography.

TABLE 3

PARAPOL ™ Grades of polybutenes

| Grade | $M_n$ | Viscosity @ 100° C., cSt |
|---|---|---|
| 450 | 420 | 10.6 |
| 700 | 700 | 78 |
| 950 | 950 | 230 |
| 1300 | 1300 | 630 |
| 2400 | 2350 | 3200 |
| 2500 | 2700 | 4400 |

TABLE 3a

Infineum Grades of Polybutenes

| Grade | $M_n$ | Viscosity @ 100° C., cSt | Viscosity Index |
|---|---|---|---|
| C9945 | 420 | 10.6 | ~75 |
| C9900 | 540 | 11.7 | ~60 |
| C9907 | 700 | 78 | ~95 |
| C9995 | 950 | 230 | ~130 |
| C9913 | 1300 | 630 | ~175 |
| C9922 | 2225 | 2500 | ~230 |
| C9925 | 2700 | 4400 | ~265 |

Desirable NFPs for use in the present invention may thus be described by any embodiment described herein, or any combination of the embodiments described herein. For example, in one embodiment, the NFP is a $C_6$ to $C_{200}$ paraffin having a pour point of less than −25° C. Described another way, the NFP comprises an aliphatic hydrocarbon having a viscosity of from 0.1 to 1000 cSt at 100° C. Described yet another way, the NFP is selected from n-paraffins, branched isoparaffins, and blends thereof having from 8 to 25 carbon atoms.

Preferred NFP's of this invention are characterized in that, when blended with the polyolefin to form a plasticized composition, the NFP is miscible with the polyolefin as indicated by no change in the number of peaks in the Dynamic Mechanical Thermal Analysis (DMTA) trace as in the unplasticized polyolefin DMTA trace. Lack of miscibility is indicated by an increase in the number of peaks in DMTA trace over those in the unplasticized polyolefin. The trace is the plot of tan-delta versus temperature, as described below.

Preferred compositions of the present invention can be characterized in that the glass transition temperature ($T_g$) of the composition decreases by at least 2° C. for every 4 wt % of NFP present in the composition in one embodiment; and decreases by at least 3° C. for every 4 wt % of NFP present in the composition in another embodiment; and decreases from at least 4 to 10° C. for every 4 wt % of NFP present in the composition in yet another embodiment, while the peak melting and crystallization temperatures of the polyolefin remain constant (within 1 to 2° C.). For purpose of this invention and the claims thereto when glass transition temperature is referred to it is the peak temperature in the DMTA trace.

Preferred compositions of the present invention can be characterized in that the glass transition temperature ($T_g$) of the composition decreases by at least 2° C. for every 1 wt % of NFP present in the composition in one embodiment; preferably by at least 3° C., preferably by at least 4° C., preferably by at least 5° C., preferably by at least 6° C., preferably by at least 7° C., preferably by at least 8° C., preferably by at least 9° C., preferably by at least 10° C., preferably by at least 11° C.; preferably while the peak melting and or crystallization temperatures of the neat polyolefin remain within 1 to 5° C. of the plasticized polyolefin, preferably within 1 to 4° C., preferably within 1 to 3° C., preferably within 1 to 2° C.

Preferred compositions of the present invention can be characterized in that the glass transition temperature ($T_g$) of the plasticized composition is at least 2° C. lower than that of the neat polyolefin, preferably at least 4° C. lower, preferably at least 6° C. lower, preferably at least 8° C. lower, preferably at least 10° C. lower, preferably at least 15° C. lower, preferably at least 20° C. lower, preferably at least 25° C. lower, preferably at least 30° C. lower, preferably at least 35° C. lower, preferably at least 40° C. lower, preferably at least 45° C. lower.

Preferred compositions of the present invention can be characterized in that the plasticized composition decreases less than 3%, preferably less than 2%, preferably less than 1% in weight when stored at 70° C. for 311 hours in a dry oven as determined by ASTM D1203 using a 0.25 mm thick sheet.

Polyolefin

The NFP's described herein are blended with at least one polyolefin to prepare the plasticized compositions of this invention. Preferred polyolefins include propylene polymers and butene polymers.

In one aspect of the invention, the polyolefin is selected from polypropylene homopolymer, polypropylene copolymers, and blends thereof. The homopolymer may be atactic polypropylene, isotactic polypropylene, syndiotactic polypropylene and blends thereof. The copolymer can be a random copolymer, a statistical copolymer, a block copolymer, and blends thereof. In particular, the inventive polymer blends described herein include impact copolymers, elastomers and plastomers, any of which may be physical blends or in situ blends with the polypropylene and or polybutene. The method of making the polypropylene or polybutene is not critical, as it can be made by slurry, solution, gas phase or other suitable processes, and by using catalyst systems appropriate for the polymerization of polyolefins, such as Ziegler-Natta-type catalysts, metallocene-type catalysts, other appropriate catalyst systems or combinations thereof. In a preferred embodiment the propylene polymers and or the butene polymers are made by the catalysts, activators and processes described in U.S. Pat. Nos. 6,342,566, 6,384,142, WO 03/040201, WO 97/19991 and U.S. Pat. No. 5,741,563. Likewise the impact copolymers may be prepared by the process described in U.S. Pat. No. 6,342,566, 6,384,142. Such catalysts are well known in the art, and are described in, for example, ZIEGLER CATALYSTS (Gerhard Fink, Rolf Mülhaupt and Hans H. Brintzinger, eds., Springer-Verlag 1995); Resconi et al., *Selectivity in Propene Polymerization with Metallocene Catalysts*, 100 CHEM. REV. 1253-1345 (2000); and I, II METALLOCENE-BASED POLYOLEFINS (Wiley & Sons 2000).

Preferred propylene homopolymers and copolymers useful in this invention typically have:

1. an Mw of 30,000 to 2,000,000 g/mol preferably 50,000 to 1,000,000, more preferably 90,000 to 500,000, as measured by GPC as described below in the test methods; and/or
2. an Mw/Mn of 1 to 40, preferably 1.6 to 20, more preferably 1.8 to 10, more preferably 1.8 to 3 as measured by GPC as described below in the test methods; and/or
3. a Tm (second melt) of 30 to 200° C., preferably 30 to 185° C., preferably 50 to 175, more preferably 60 to 170 as measured by the DSC method described below in the test methods; and/or
4. a crystallinity of 5 to 80%, preferably 10 to 70, more preferably 20 to 60% as measured by the DSC method described below in the test methods; and/or
5. a glass transition temperature ($T_g$) of −40° C. to 20° C., preferably −20° C. to 10° C., more preferably −10° C. to 5° C. as measured by the DMTA method described below in the test methods; and or
6. a heat of fusion (Hf) of 180 J/g or less, preferably 20 to 150 J/g, more preferably 40 to 120 J/g as measured by the DSC method described below in the test methods; and or
7. a crystallization temperature (Tc) of 15 to 120° C., preferably 20 to 115° C., more preferably 25 to 110° C., preferably 60 to 145° C., as measured by the method described below in the test methods; and or
8. a heat deflection temperature of 45 to 140° C., preferably 60 to 135° C., more preferably 75 to 125° C. as measured by the method described below in the test methods; and or
9. a Rockwell hardness (R scale) of 25 or more, preferably 40 or more, preferably 60 or more, preferably 80 or more, preferably 100 or more, preferably from 25 to 125; and or
10. a percent crystallinity of at least 30%, preferably at least 40%, alternatively at least 50%, as measured by the method described below in the test methods; and or
11. a percent amorphous content of at least 50%, alternatively at least 60%, alternatively at least 70%, even alternatively between 50 and 95%, or 70% or less, preferably 60% or less, preferably 50% or less as determined by subtracting the percent crystallinity from 100, and or
12. a branching index (g') of 0.2 to 2.0, preferably 0.5 to 1.5, preferably 0.7 to 1.1, as measured by the method described below.

The polyolefin may be a propylene homopolymer. In one embodiment the propylene homopolymer has a molecular weight distribution (Mw/Mn) of up to 40, preferably ranging from 1.5 to 10, and from 1.8 to 7 in another embodiment, and from 1.9 to 5 in yet another embodiment, and from 2.0 to 4 in yet another embodiment. In another embodiment the propylene homopolymer has a Gardner impact strength, tested on 0.125 inch disk at 23° C., that may range from 20 in-lb to 1000 in-lb in one embodiment, and from 30 in-lb to 500 in-lb in another embodiment, and from 40 in-lb to 400 in-lb in yet another embodiment. In yet another embodiment, the 1% secant flexural modulus may range from 100 MPa to 2300 MPa, and from 200 MPa to 2100 MPa in another embodiment, and from 300 MPa to 2000 MPa in yet another embodiment, wherein a desirable polyolefin may exhibit any combination of any upper flexural modulus limit with any lower flexural modulus limit. The melt flow rate (MFR) (ASTM D 1238, 230° C., 2.16 kg) of preferred propylene polymers range from 0.1 dg/min to 2500 dg/min in one embodiment, and from 0.3 to 500 dg/min in another embodiment.

The polypropylene homopolymer or propylene copolymer useful in the present invention may have some level of isotacticity. Thus, in one embodiment, a polyolefin comprising isotactic polypropylene is a useful polymer in the invention of this patent, and similarly, highly isotactic polypropylene is useful in another embodiment. As used herein, "isotactic" is defined as having at least 10% isotactic pentads according to analysis by $^{13}$C-NMR as described in the test methods below. As used herein, "highly isotactic" is defined as having at least 60% isotactic pentads according to analysis by $^{13}$C-NMR. In a desirable embodiment, a polypropylene homopolymer having at least 85% isotacticity is the polyolefin, and at least 90% isotacticity in yet another embodiment.

In another desirable embodiment, a polypropylene homopolymer having at least 85% syndiotacticity is the polyolefin, and at least 90% syndiotacticity in yet another embodiment. As used herein, "syndiotactic" is defined as having at least 10% syndiotactic pentads according to analysis by $^{13}$C-NMR as described in the test methods below. As used herein, "highly syndiotactic" is defined as having at least 60% syndiotactic pentads according to analysis by $^{13}$C-NMR.

In another embodiment the propylene homoploymer may be isotactic, highly isotactic, syndiotactic, highly syndiotactic or atactic. Atactic polypropylene is defined to be less than 10% isotactic or syndiotactic pentads. Preferred atactic polypropylenes typically have an Mw of 20,000 up to 1,000,000.

Preferred propylene polymers that are useful in this invention include those sold under the tradenames ACHIEVE™ and ESCORENE™ by ExxonMobil Chemical Company in Houston Tex.

In another embodiment of the invention, the polyolefin is a propylene copolymer, either random, or block, of propylene derived units and units selected from ethylene and $C_4$ to $C_{20}$ α-olefin derived units, typically from ethylene and $C_4$ to $C_{10}$ α-olefin derived units in another embodiment. The ethylene or $C_4$ to $C_{20}$ α-olefin derived units are present from 0.1 wt % to 50 wt % of the copolymer in one embodiment, and from 0.5 to 30 wt % in another embodiment, and from 1 to 15 wt % in yet another embodiment, and from 0.1 to 5 wt % in yet another embodiment, wherein a desirable copolymer comprises ethylene and $C_4$ to $C_{20}$ α-olefin derived units in any combination of any upper wt % limit with any lower wt % limit described herein. The propylene copolymer will have a weight average molecular weight of from greater than 8,000 g/mol in one embodiment, and greater than 10,000 g/mol in another embodiment, and greater than 12,000 g/mol in yet another embodiment, and greater than 20,000 g/mol in yet another embodiment, and less than 1,000,000 g/mol in yet another embodiment, and less than 800,000 in yet another embodiment, wherein a desirable copolymer may comprise any upper molecular weight limit with any lower molecular weight limit described herein.

Particularly desirable propylene copolymers have a molecular weight distribution (Mw/Mn) ranging from 1.5 to 10, and from 1.6 to 7 in another embodiment, and from 1.7 to 5 in yet another embodiment, and from 1.8 to 4 in yet another embodiment. The Gardner impact strength, tested on 0.125 inch disk at 23° C., of the propylene copolymer may range from 20 in-lb to 1000 in-lb in one embodiment, and from 30 in-lb to 500 in-lb in another embodiment, and from 40 in-lb to 400 in-lb in yet another embodiment. In yet another embodiment, the 1% secant flexural modulus of the propylene copolymer ranges from 100 MPa to 2300 MPa, and from 200 MPa to 2100 MPa in another embodiment, and from 300 MPa to 2000 MPa in yet another embodiment, wherein a desirable polyolefin may exhibit any combination of any upper flexural modulus limit with any lower flexural modulus limit. The melt flow rate (MFR) (ASTM D 1238, 230° C., 2.16 kg) of propylene copolymer ranges from 0.1 dg/min to 2500 dg/min in one embodiment, and from 0.3 to 500 dg/min in another embodiment.

In another embodiment the polyolefin may be a propylene copolymer comprising propylene and one or more other monomers selected from the group consisting of ethylene and $C_4$ to $C_{20}$ linear, branched or cyclic monomers, and in some embodiments is a $C_4$ to $C_{12}$ linear or branched alpha-olefin, preferably butene, pentene, hexene, heptene, octene, nonene, decene, dodecene, 4-methyl-pentene-1,3-methyl pentene-1, 3,5,5-trimethyl-hexene-1, and the like. The monomers may be present at up to 50 weight %, preferably from 0 to 40 weight %, more preferably from 0.5 to 30 weight %, more preferably from 2 to 30 weight %, more preferably from 5 to 20 weight %.

In a preferred embodiment the butene homopolymers and copolymers useful in this invention typically have:
1. an Mw of 30,000 to 2,000,000 g/mol preferably 50,000 to 1,000,000, more preferably 90,000 to 500,000, as measured by GPC as described below in the test methods; and/or
2. an Mw/Mn of 1 to 40, preferably 1.6 to 20, more preferably 1.8 to 10, more preferably 1.8 to 3 as measured by GPC as described below in the test methods; and/or
3. a Tm (second melt) of 30 to 150° C., preferably 30 to 145° C., preferably 50 to 135, as measured by the DSC method described below in the test methods; and/or
4. a crystallinity of 5 to 80%, preferably 10 to 70, more preferably 20 to 60% as measured by the DSC method described below in the test methods; and/or
5. a glass transition temperature (Tg) of −50° C. to 0° C. as measured by the DMTA method described below in the test methods; and or
6. a heat of fusion (Hf) of 180 J/g or less, preferably 20 to 150 J/g, more preferably 40 to 120 J/g as measured by the DSC method described below in the test methods; and or
7. a crystallization temperature (Tc) of 10 to 130° C., preferably 20 to 115° C., more preferably 25 to 110° C., preferably 60 to 145° C., as measured by the method described below in the test methods; and or
8. a percent amorphous content of at least 50%, alternatively at least 60%, alternatively at least 70%, even alternatively between 50 and 95%, or 70% or less, preferably 60% or less, preferably 50% or less as determined by subtracting the percent crystallinity from 100, and or
9. A branching index (g') of 0.2 to 2.0, preferably 0.5 to 1.5, preferably 0.7 to 1.1, as measured by the method described below.

Preferred linear alpha-olefins useful as comonomers for the propylene copolymers useful in this invention include $C_3$ to $C_8$ alpha-olefins, more preferably 1-butene, 1-hexene, and 1-octene, even more preferably 1-butene. Preferred linear alpha-olefins useful as comonomers for the butene copolymers useful in this invention include $C_3$ to $C_8$ alpha-olefins, more preferably propylene, 1-hexene, and 1-octene, even more preferably propylene. Preferred branched alpha-olefins include 4-methyl-1-pentene, 3-methyl-1-pentene, and 3,5,5-trimethyl-1-hexene, 5-ethyl-1-nonene. Preferred aromatic-group-containing monomers contain up to 30 carbon atoms.

Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to C1 to C10 alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, paramethyl styrene, 4-phenyl-1-butene and allyl benzene.

Non aromatic cyclic group containing monomers are also preferred. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, C1 to C10 alkyl groups. Preferred non-aromatic cyclic group containing monomers include vinylcyclohexane, vinylcyclohexene, vinylnorbornene, ethylidene norbornene, cyclopentadiene, cyclopentene, cyclohexene, cyclobutene, vinyladamantane and the like.

Preferred diolefin monomers useful in this invention include any hydrocarbon structure, preferably C4 to C30, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

In a preferred embodiment one or more dienes are present in the polymer produced herein at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

In yet another embodiment, the Gardner impact strength, tested on 0.125 inch disk at 23° C., of the butene copolymer ranges from 20 in-lb to 1000 in-lb, and from 30 in-lb to 500 in-lb in another embodiment, and from 40 in-lb to 400 in-lb in yet another embodiment. Further, the butene copolymer may possess a 1% secant flexural modulus ranging from 100 MPa to 2300 MPa, and from 200 MPa to 2100 MPa in another embodiment, and from 300 MPa to 2000 MPa in yet another embodiment, wherein a desirable polyolefin may exhibit any combination of any upper flexural modulus limit with any lower flexural modulus limit. The melt flow rate (MFR) (ASTM D 1238, 230° C.) of desirable copolymers ranges from 0.1 dg/min to 2500 dg/min in one embodiment, and from 0.1 to 500 dg/min in another embodiment.

In another embodiment the propylene copolymer is a random copolymer, also known as an "RCP," comprising propylene and up to 20 mole % of ethylene or a $C_4$ to $C_{20}$ olefin, preferably up to 20 mole % ethylene.

In another embodiment, the polyolefin may be an impact copolymer (ICP) or block copolymer. Propylene impact copolymers are commonly used in a variety of applications where strength and impact resistance are desired such as molded and extruded automobile parts, household appliances, luggage and furniture. Propylene homopolymers alone are often unsuitable for such applications because they are too brittle and have low impact resistance particularly at low temperature, whereas propylene impact copolymers are specifically engineered for applications such as these.

A typical propylene impact copolymer contains at least two phases or components, e.g., a homopolymer component and a copolymer component. The impact copolymer may also comprise three phases such as a PP/EP/PE combination with the PP continuous and a dispersed phase with EP outside and PE inside the dispersed phase particles. These components are usually produced in a sequential polymerization process wherein the homopolymer produced in a first reactor is transferred to a second reactor where copolymer is produced and incorporated within the matrix of the homopolymer component. The copolymer component has rubbery characteristics and provides the desired impact resistance, whereas the homopolymer component provides overall stiffness.

Another important feature of ICP's is the amount of amorphous polypropylene they contain. The ICP's of this invention are characterized as having low amorphous polypropylene, preferably less than 3% by weight, more preferably less than 2% by weight, even more preferably less than 1% by weight and most preferably there is no measurable amorphous polypropylene. Percent amorphous polypropylene is determined by the method described below in the test methods.

Preferred impact copolymers may be a reactor blend (in situ blend) or a post reactor (ex-situ) blend. In one embodiment, a suitable impact copolymer comprises from 40% to 95% by weight Component A and from 5% to 60% by weight Component B based on the total weight of the impact copolymer; wherein Component A comprises propylene homopolymer or copolymer, the copolymer comprising 10% or less by weight ethylene, butene, hexene or octene comonomer; and wherein Component B comprises propylene copolymer, wherein the copolymer comprises from 5% to 70% by weight ethylene, butene, hexene and/or octene comonomer, and from about 95% to about 30% by weight propylene. In one embodiment of the impact copolymer, Component B consists essentially of propylene and from about 30% to about 65% by weight ethylene. In another embodiment, Component B comprises ethylene-propylene copolymers, ethylene-propylene-diene terpolymers, ethylene-acrylate copolymers, ethylene-vinyl acetate, styrene-butadiene copolymers, ethylene-acrylic ester copolymers, polybutadiene, polyisoprene, natural rubber, isobutylene, hydrocarbon resin (the hydrocarbon resin being characterized by a molecular weight less than 5000, a $T_g$ of about 50 to 100° C. and a softening point, Ring and Ball, as measured by ASTM E-28, of less than about 140° C.), rosin ester, and mixtures thereof. In another embodiment, Component B has a molecular weight distribution of less than 3.5. In yet another embodiment, Component B has a weight average molecular weight of at least 20,000. A useful impact copolymer is disclosed in, for example, U.S. Pat. Nos. 6,342,566 and 6,384,142.

Component B is most preferably a copolymer consisting essentially of propylene and ethylene although other propylene copolymers, ethylene copolymers or terpolymers may be suitable depending on the particular product properties desired. For example, propylene/butene, hexene or octene copolymers, and ethylene/butene, hexene or octene copolymers may be used, and propylene/ethylene/hexene-1 terpolymers may be used. In a preferred embodiment though, Component B is a copolymer comprising at least 40% by weight propylene, more preferably from about 80% by weight to about 30% by weight propylene, even more preferably from about 70% by weight to about 35% by weight propylene. The comonomer content of Component B is preferably in the range of from about 20% to about 70% by weight comonomer, more preferably from about 30% to about 65% by weight comonomer, even more preferably from about 35% to about 60% by weight comonomer. Most preferably Component B consists essentially of propylene and from about 20% to about 70% ethylene, more preferably from about 30% to about 65% ethylene, and most preferably from about 35% to about 60% ethylene.

For other Component B copolymers, the comonomer contents will need to be adjusted depending on the specific properties desired. For example, for ethylene/hexene copolymers, Component B should contain at least 17% by weight hexene and at least 83% by weight ethylene.

Component B, preferably has a narrow molecular weight distribution Mw/Mn ("MWD"), i.e., lower than 5.0, preferably lower than 4.0, more preferably lower than 3.5, even more preferably lower than 3.0 and most preferably 2.5 or lower. These molecular weight distributions should be obtained in the absence of visbreaking or peroxide or other post reactor treatment molecular weight tailoring. Component B preferably has a weight average molecular weight (Mw as determined by GPC) of at least 100,000, preferably at least 150,000, and most preferably at least 200,000.

Component B preferably has an intrinsic viscosity greater than 1.00 dl/g, more preferably greater than 1.50 dl/g and most preferably greater than 2.00 dl/g. The term "intrinsic viscosity" or "IV" is used conventionally herein to mean the viscosity of a solution of polymer such as Component B in a given solvent at a given temperature, when the polymer composition is at infinite dilution. According to the ASTM standard test method D 1601-78, IV measurement involves a standard capillary viscosity measuring device, in which the viscosity of a series of concentrations of the polymer in the solvent at the given temperature are determined. For Component B, decalin is a suitable solvent and a typical temperature is 135° C. From the values of the viscosity of solutions of varying concentrations, the "value" at infinite dilution can be determined by extrapolation.

Component B preferably has a composition distribution breadth index (CDBI) of greater than 60%, more preferably greater than 65%, even more preferably greater than 70%, even more preferably greater than 75%, still more preferably greater than 80%, and most preferably greater than 85%. CDBI defines the compositional variation among polymer chains in terms of ethylene (or other comonomer) content of the copolymer as a whole. A measure of composition distribution is the "Composition Distribution Breadth Index" ("CDBI") as defined in U.S. Pat. No. 5,382,630 which is hereby incorporate by reference. CDBI is defined as the weight percent of the copolymer molecules having a comonomer content within 50% of the median total molar comonomer content. The CDBI of a copolymer is readily determined utilizing well known techniques for isolating individual fractions of a sample of the copolymer. One such technique is Temperature Rising Elution Fraction (TREF), as described in Wild, et al., *J. Poly. Sci., Poly. Phys. Ed.*, vol. 20, p. 441 (1982) and U.S. Pat. No. 5,008,204, which are incorporated herein by reference.

Component B of the ICP's preferably has low crystallinity, preferably less than 10% by weight of a crystalline portion, more preferably less than 5% by weight of a crystalline portion. Where there is a crystalline portion of Component B, its composition is preferably the same as or at least similar to (within 15% by weight) the remainder of Component B in terms of overall comonomer weight percent.

The preferred melt flow rate ("MFR") of these ICP's depends on the desired end use but is typically in the range of from about 0.2 dg/min to about 200 dg/min, more preferably from about 5 dg/min to about 100 dg/min. Significantly, high MFRs, i.e., higher than 50 dg/min are obtainable. The ICP preferably has a melting point (Tm) of at least 145° C., preferably at least 150° C., more preferably at least 152° C., and most preferably at least 155° C.

The ICP's comprise from about 40% to about 95% by weight Component A and from about 5% to about 60% by weight Component B, preferably from about 50% to about 95% by weight Component A and from about 5% to about 50% Component B, even more preferably from about 60% to about 90% by weight Component A and from about 10% to about 40% by weight Component B. In the most preferred embodiment, the ICP consists essentially of Components A and B. The overall comonomer (preferably ethylene) content of the total ICP is preferably in the range of from about 2% to about 30% by weight, preferably from about 5% to about 25% by weight, even more preferably from about 5% to about 20% by weight, still more preferably from about 5% to about 15% by weight comonomer.

In another embodiment a preferred impact copolymer composition is prepared by selecting Component A and Component B such that their refractive indices (as measured by ASTM D 542-00) are within 20% of each other, preferably within 15%, preferably 10, even more preferably within 5% of each other. This selection produces impact copolymers with outstanding clarity. In another embodiment a preferred impact copolymer composition is prepared by selecting a blend of Component A and an NFP and a blend of Component B and an NFP such that refractive indices of the blends (as measured by ASTM D 542-00) are within 20% of each other, preferably within 15%, preferably 10, even more preferably within 5% of each other.

In yet another embodiment, the Gardner impact strength, tested on 0.125 inch disk at −29° C., of the propylene impact copolymer ranges from 20 in-lb to 1000 in-lb, and from 30 in-lb to 500 in-lb in another embodiment, and from 40 in-lb to 400 in-lb in yet another embodiment. Further, the 1% secant flexural modulus of the propylene impact copolymer may range from 100 MPa to 2300 MPa in one embodiment, and from 200 MPa to 2100 MPa in another embodiment, and from 300 MPa to 2000 MPa in yet another embodiment, wherein a desirable polyolefin may exhibit any combination of any upper flexural modulus limit with any lower flexural modulus limit. The melt flow rate (MFR) (ASTM D 1238, 230° C., 2.16 kg) of desirable homopolymers ranges from 0.1 dg/min to 2500 dg/min in one embodiment, and from 0.3 to 500 dg/min in another embodiment.

Another suitable polyolefin comprises a blend of a polypropylene homopolymer or propylene copolymer with a plastomer. The plastomers that are useful in the present invention may be described as polyolefin copolymers having a density of from 0.85 to 0.915 g/cm$^3$ ASTM D 4703 Method B and ASTM D 1505—the first of these is compression molding at a cooling rate of 15° C./min and the second is the Gradient Density Column method for density determination and a melt index (MI) between 0.10 and 30 dg/min (ASTM D 1238; 190° C., 2.1 kg). In one embodiment, the useful plastomer is a copolymer of ethylene derived units and at least one of $C_3$ to $C_{10}$ α-olefin derived units, the copolymer having a density less than 0.915 g/cm$^3$. The amount of comonomer ($C_3$ to $C_{10}$ α-olefin derived units) present in the plastomer ranges from 2 wt % to 35 wt % in one embodiment, and from 5 wt % to 30 wt % in another embodiment, and from 15 wt % to 25 wt % in yet another embodiment, and from 20 wt % to 30 wt % in yet another embodiment.

The plastomer useful in the invention has a melt index (MI) of between 0.10 and 20 dg/min in one embodiment, and from 0.2 to 10 dg/min in another embodiment, and from 0.3 to 8 dg/min in yet another embodiment. The average molecular weight of useful plastomers ranges from 10,000 to 800,000 in one embodiment, and from 20,000 to 700,000 in another embodiment. The 1% secant flexural modulus (ASTM D 790) of useful plastomers ranges from 10 MPa to 150 MPa in one embodiment, and from 20 MPa to 100 MPa in another embodiment. Further, the plastomer that is useful in compositions of the present invention has a melting temperature ($T_m$) of from 30 to 80° C. (first melt peak) and from 50 to 125° C. (second melt peak) in one embodiment, and from 40 to 70° C. (first melt peak) and from 50 to 100° C. (second melt peak) in another embodiment.

Plastomers useful in the present invention are metallocene catalyzed copolymers of ethylene derived units and higher α-olefin derived units such as propylene, 1-butene, 1-hexene and 1-octene, and which contain enough of one or more of these comonomer units to yield a density between 0.860 and 0.900 g/cm$^3$ in one embodiment. The molecular weight distribution (Mw/Mn) of desirable plastomers ranges from 1.5 to 5 in one embodiment, and from 2.0 to 4 in another embodiment. Examples of a commercially available plastomers are EXACT 4150, a copolymer of ethylene and 1-hexene, the 1-hexene derived units making up from 18 to 22 wt % of the plastomer and having a density of 0.895 g/cm$^3$ and MI of 3.5 dg/min (ExxonMobil Chemical Company, Houston, Tex.); and EXACT 8201, a copolymer of ethylene and 1-octene, the 1-octene derived units making up from 26 to 30 wt % of the plastomer, and having a density of 0.882 g/cm$^3$ and MI of 1.0 dg/min (ExxonMobil Chemical Company, Houston, Tex.).

In another embodiment polymers that are useful in this invention include homopolymers and random copolymers of propylene having a heat of fusion as determined by Differential Scanning Calorimetry (DSC) of less than 50 J/g, a melt index (MI) of less than 20 dg/min and or an MFR of 20 dg/min or less, and contains stereoregular propylene crystallinity preferably isotactic stereoregular propylene crystallinity. In another embodiment the polymer is a random copolymer of propylene and at least one comonomer selected from ethylene, $C_4$-$C_{12}$ a-olefins, and combinations thereof. Preferably the random copolymers of propylene comprises from 2 wt % to 25 wt % polymerized ethylene units, based on the total weight of the polymer; has a narrow composition distribution; has a melting point (Tm) of from 25° C. to 120° C., or from 35° C. to 80° C.; has a heat of fusion within the range having an upper limit of 50 J/g or 25 J/g and a lower limit of 1 J/g or 3 J/g; has a molecular weight distribution Mw/Mn of from 1.8 to 4.5; and has a melt index (MI) of less than 20 dg/min, or less than 15 dg/min. The intermolecular composition distribution of the copolymer is determined by thermal fractionation in a solvent. A typical solvent is a saturated hydrocarbon such as hexane or heptane. The thermal fractionation procedure is described below. Typically, approximately 75% by weight, preferably 85% by weight, of the copolymer is isolated as one or two adjacent, soluble fractions with the balance of the copolymer in immediately preceding or succeeding fractions. Each of these fractions has a composition (wt % comonomer such as ethylene or other α-olefin) with a difference of no greater than 20% (relative), preferably 10% (relative), of the average weight % comonomer of the copolymer. The copolymer has a narrow composition distribution if it meets the fractionation test described above.

A particularly preferred polymer useful in the present invention is an elastic polymer with a moderate level of crystallinity due to stereoregular propylene sequences. The polymer can be: (A) a propylene homopolymer in which the stereoregularity is disrupted in some manner such as by regio-inversions; (B) a random propylene copolymer in which the propylene stereoregularity is disrupted at least in part by comonomers; or (C) a combination of (A) and (B).

In one embodiment, the polymer further includes a non-conjugated diene monomer to aid in vulcanization and other chemical modification of the blend composition. The amount of diene present in the polymer is preferably less than 10% by weight, and more preferably less than 5% by weight. The diene may be any non-conjugated diene which is commonly used for the vulcanization of ethylene propylene rubbers including, but not limited to, ethylidene norbornene, vinyl norbornene, and dicyclopentadiene.

In one embodiment, the polymer is a random copolymer of propylene and at least one comonomer selected from ethylene, $C_4$-$C_{12}$ a-olefins, and combinations thereof. In a particular aspect of this embodiment, the copolymer includes ethylene-derived units in an amount ranging from a lower limit of 2%, 5%, 6%, 8%, or 10% by weight to an upper limit of 20%, 25%, or 28% by weight. This embodiment will also include propylene-derived units present in the copolymer in an amount ranging from a lower limit of 72%, 75%, or 80% by weight to an upper limit of 98%, 95%, 94%, 92%, or 90% by weight. These percentages by weight are based on the total weight of the propylene and ethylene-derived units; i.e., based on the sum of weight percent propylene-derived units and weight percent ethylene-derived units being 100%. The ethylene composition of a polymer can be measured as follows. A thin homogeneous film is pressed at a temperature of about 150° C. or greater, then mounted on a Perkin Elmer PE 1760 infrared spectrophotometer. A full spectrum of the sample from 600 $cm^{-1}$ to 4000 $cm^{-1}$ is recorded and the monomer weight percent of ethylene can be calculated according to the following equation: Ethylene wt %=$82.585-111.987X+30.045X^2$, wherein X is the ratio of the peak height at 1155 $cm^{-1}$ and peak height at either 722 $cm^{-1}$ or 732 $cm^{-1}$, whichever is higher. The concentrations of other monomers in the polymer can also be measured using this method.

Comonomer content of discrete molecular weight ranges can be measured by Fourier Transform Infrared Spectroscopy (FTIR) in conjunction with samples collected by GPC. One such method is described in Wheeler and Willis, Applied Spectroscopy, 1993, vol. 47, pp. 1128-1130. Different but similar methods are equally functional for this purpose and well known to those skilled in the art.

Comonomer content and sequence distribution of the polymers can be measured by $^{13}C$ nuclear magnetic resonance ($^{13}C$ NMR), and such method is well known to those skilled in the art.

In one embodiment, the polymer is a random propylene copolymer having a narrow composition distribution. In another embodiment, the polymer is a random propylene copolymer having a narrow composition distribution and a melting point of from 25° C. to 110° C. The copolymer is described as random because for a polymer comprising propylene, comonomer, and optionally diene, the number and distribution of comonomer residues is consistent with the random statistical polymerization of the monomers. In stereoblock structures, the number of block monomer residues of any one kind adjacent to one another is greater than predicted from a statistical distribution in random copolymers with a similar composition. Historical ethylene-propylene copolymers with stereoblock structure have a distribution of ethylene residues consistent with these blocky structures rather than a random statistical distribution of the monomer residues in the polymer. The intramolecular composition distribution (i.e., randomness) of the copolymer may be determined by $^{13}C$ NMR, which locates the comonomer residues in relation to the neighbouring propylene residues. The intermolecular composition distribution of the copolymer is determined by thermal fractionation in a solvent. A typical solvent is a saturated hydrocarbon such as hexane or heptane. Typically, approximately 75% by weight, preferably 85% by weight, of the copolymer is isolated as one or two adjacent, soluble fractions with the balance of the copolymer in immediately preceding or succeeding fractions. Each of these fractions has a composition (wt % comonomer such as ethylene or other α-olefin) with a difference of no greater than 20% (relative), preferably 10% (relative), of the average weight % comonomer of the copolymer. The copolymer has a narrow composition distribution if it meets the fractionation test described above. To produce a copolymer having the desired randomness and narrow composition, it is beneficial if (1) a single sited metallocene catalyst is used which allows only a single statistical mode of addition of the first and second monomer sequences and (2) the copolymer is well-mixed in a continuous flow stirred tank polymerization reactor which allows only a single polymerization environment for substantially all of the polymer chains of the copolymer.

The crystallinity of the polymers may be expressed in terms of heat of fusion. Embodiments of the present invention include polymers having a heat of fusion, as determined by DSC, ranging from a lower limit of 1.0 J/g, or 3.0 J/g, to an upper limit of 50 J/g, or 10 J/g. Without wishing to be bound by theory, it is believed that the polymers of embodiments of the present invention have generally isotactic crystallizable propylene sequences, and the above heats of fusion are believed to be due to the melting of these crystalline segments.

The crystallinity of the polymer may also be expressed in terms of crystallinity percent. The thermal energy for the highest order of polypropylene is estimated at 207 J/g. That is, 100% crystallinity is equal to 207 J/g. Preferably, the polymer has a polypropylene crystallinity within the range having an upper limit of 65%, 40%, 30%, 25%, or 20%, and a lower limit of 1%, 3%, 5%, 7%, or 8%.

The level of crystallinity is also reflected in the melting point. The term "melting point," as used herein, is the highest peak highest meaning the largest amount of polymer being reflected as opposed to the peak occurring at the highest temperature among principal and secondary melting peaks as determined by DSC, discussed above. In one embodiment of the present invention, the polymer has a single melting point. Typically, a sample of propylene copolymer will show secondary melting peaks adjacent to the principal peak, which are considered together as a single melting point. The highest of these peaks is considered the melting point. The polymer preferably has a melting point by DSC ranging from an upper limit of 110° C., 105° C., 90° C., 80° C., or 70° C., to a lower limit of 0° C., 20° C., 25° C., 30° C., 35° C., 40° C., or 45° C.

Such polymers used in the invention have a weight average molecular weight (Mw) within the range having an upper limit of 5,000,000 g/mol, 1,000,000 g/mol, or 500,000 g/mol, and a lower limit of 10,000 g/mol, 20,000 g/mol, or 80,000 g/mol, and a molecular weight distribution Mw/Mn (MWD), sometimes referred to as a "polydispersity index" (PDI), ranging from a lower limit of 1.5, 1.8, or 2.0 to an upper limit of 40, 20, 10, 5, or 4.5. In one embodiment, the polymer has a Mooney viscosity, ML(1+4) @ 125° C., of 100 or less, 75 or less, 60 or less, or 30 or less. Mooney viscosity, as used herein, can be measured as ML(1+4) @ 125° C. according to ASTM D1646, unless otherwise specified.

The polymers used in embodiments of the present invention can have a tacticity index (m/r) ranging from a lower limit of 4 or 6 to an upper limit of 8, 10, or 12. The tacticity index, expressed herein as "m/r", is determined by $^{13}$C nuclear magnetic resonance (NMR). The tacticity index m/r is calculated as defined in H. N. Cheng, *Macromolecules*, 17, 1950 (1984). The designation "m" or "r" describes the stereochemistry of pairs of contiguous propylene groups, "m" referring to meso and "r" to racemic. An m/r ratio of 0 to less than 1.0 generally describes a syndiotactic polymer, and an m/r ratio of 1.0 an atactic material, and an m/r ratio of greater than 1.0 an isotactic material. An isotactic material theoretically may have a ratio approaching infinity, and many by-product atactic polymers have sufficient isotactic content to result in ratios of greater than 50.

In one embodiment, the polymer has isotactic stereoregular propylene crystallinity. The term "stereoregular" as used herein means that the predominant number, i.e. greater than 80%, of the propylene residues in the polypropylene or in the polypropylene continuous phase of a blend, such as impact copolymer exclusive of any other monomer such as ethylene, has the same 1,2 insertion and the stereochemical orientation of the pendant methyl groups is the same, either meso or racemic.

An ancillary procedure for the description of the tacticity of the propylene units of embodiments of the current invention is the use of triad tacticity. The triad tacticity of a polymer is the relative tacticity of a sequence of three adjacent propylene units, a chain consisting of head to tail bonds, expressed as a binary combination of m and r sequences. It is usually expressed for copolymers of the present invention as the ratio of the number of units of the specified tacticity to all of the propylene triads in the copolymer.

The triad tacticity (mm fraction) of a propylene copolymer can be determined from a $^{13}$C NMR spectrum of the propylene copolymer and the following formula:

$$mm \text{ Fraction} = \frac{PPP(mm)}{PPP(mm) + PPP(mr) + PPP(rr)}$$

where PPP(mm), PPP(mr) and PPP(rr) denote peak areas derived from the methyl groups of the second units in the following three propylene unit chains consisting of head-to-tail bonds:

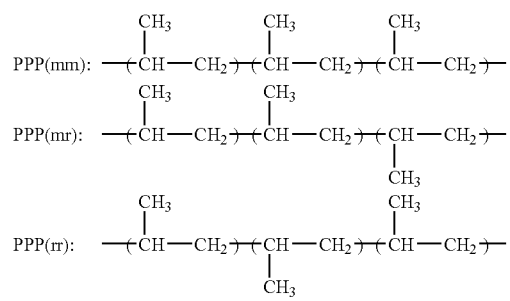

The $^{13}$C NMR spectrum of the propylene copolymer is measured as described in U.S. Pat. No. 5,504,172. The spectrum relating to the methyl carbon region (19-23 parts per million (ppm)) can be divided into a first region (21.2-21.9 ppm), a second region (20.3-21.0 ppm) and a third region (19.5-20.3 ppm). Each peak in the spectrum was assigned with reference to an article in the journal Polymer, Volume 30 (1989), page 1350. In the first region, the methyl group of the second unit in the three propylene unit chain represented by PPP (mm) resonates. In the second region, the methyl group of the second unit in the three propylene unit chain represented by PPP (mr) resonates, and the methyl group (PPE-methyl group) of a propylene unit whose adjacent units are a propylene unit and an ethylene unit resonates (in the vicinity of 20.7 ppm). In the third region, the methyl group of the second unit in the three propylene unit chain represented by PPP (rr) resonates, and the methyl group (EPE-methyl group) of a propylene unit whose adjacent units are ethylene units resonates (in the vicinity of 19.8 ppm).

The calculation of the triad tacticity is outlined in the techniques shown in U.S. Pat. No. 5,504,172. Subtraction of the peak areas for the error in propylene insertions (both 2,1 and 1,3) from peak areas from the total peak areas of the second region and the third region, the peak areas based on the 3 propylene units-chains (PPP(mr) and PPP(rr)) consisting of head-to-tail bonds can be obtained. Thus, the peak areas of PPP(mm), PPP(mr) and PPP(rr) can be evaluated, and hence the triad tacticity of the propylene unit chain consisting of head-to-tail bonds can be determined.

The polymers of embodiments of the present invention have a triad tacticity of three propylene units, as measured by $^{13}$C NMR, of 75% or greater, 80% or greater, 82% or greater, 85% or greater, or 90% or greater.

In embodiments of the present invention, the polymer has a melt index (MI) of 20 dg/min or less, 7 dg/min or less, 5 dg/min or less, or 2 dg/min or less, or less than 2 dg/min. The determination of the MI of the polymer is according to ASTM D1238 (190° C., 2.16 kg). In this version of the method a portion of the sample extruded during the test was collected and weighed. This is commonly referred to as the modification 1 of the experimental procedure. The sample analysis is conducted at 190° C. with a 1 minute preheat on the sample to provide a steady temperature for the duration of the experiment.

In one embodiment, the polymer used in the present invention is described in detail as the "Second Polymer Component (SPC)" in WO 00/69963, WO 00/01766, WO 99/07788, WO 02/083753, and described in further detail as the "Propylene Olefin Copolymer" in WO 00/01745, all of which are fully incorporated by reference herein for purposes of U.S. patent practice.

The polyolefin suitable for use in the present invention can be in any physical form when used to blend with the NFP of the invention. In one embodiment, reactor granules, defined as the granules of polymer that are isolated from the polymerization reactor prior to any processing procedures, are used to blend with the NFP of the invention. The reactor granules have an average diameter of from 50 µm to 10 mm in one embodiment, and from 10 µm to 5 mm in another embodiment. In another embodiment, the polyolefin is in the form of pellets, such as, for example, having an average diameter of from 1 mm to 10 mm that are formed from melt extrusion of the reactor granules.

In one embodiment of the invention, the polyolefin suitable for the composition excludes physical blends of polypropylene with other polyolefins, and in particular, excludes physical blends of polypropylene with low molecular weight (500 to 10,000 g/mol) polyethylene or polyethylene copolymers, meaning that, low molecular weight polyethylene or polyethylene copolymers are not purposefully added in any amount to the polyolefin (e.g., polypropylene homopolymer or copolymer) compositions of the invention, such as is the case in, for example, WO 01/18109 A1.

In a preferred embodiment, the NFP is an isoparaffin comprising $C_6$ to $C_{25}$ isoparaffins. In another embodiment the non-functionalized plasticizer is a polyalphaolefin comprising $C_{10}$ to $C_{100}$ n-paraffins. The polyolefin may be a polypropylene homopolymer, copolymer, impact copolymer, or blends thereof, and may include a plastomer. Non-limiting examples of desirable articles of manufacture made from compositions of the invention include films, sheets, fibers, woven and nonwoven fabrics, tubes, pipes, automotive components, furniture, sporting equipment, food storage containers, transparent and semi-transparent articles, toys, tubing and pipes, and medical devices. The compositions of the invention may be characterized by having an improved (decreased) $T_g$ relative to the starting polyolefin, while maintaining other desirable properties.

The polyolefin and NFP can be blended by any suitable means, and are typically blended to obtain a homogeneous, single phase mixture. For example, they may be blended in a tumbler, static mixer, batch mixer, extruder, or a combination thereof. The mixing step may take place as part of a processing method used to fabricate articles, such as in the extruder on an injection molding maching or fiber line.

The enhanced properties of the plasticized polyolefin compositions described herein are useful in a wide variety of applications, including transparent articles such as cook and storage ware, and in other articles such as furniture, automotive components, toys, sportswear, medical devices, sterilizable medical devices and sterilization containers, nonwoven fibers and fabrics and articles therefrom such as drapes, gowns, filters, hygiene products, diapers, and films, oriented films, sheets, tubes, pipes and other items where softness, high impact strength, and impact strength below freezing is important. Fabrication of the plasticized polyolefins of the invention to form these articles may be accomplished by injection molding, extrusion, thermoforming, blow molding, rotomolding, spunbonding, meltblowing, fiber spinning, blown film, stretching for oriented films, and other common processing methods.

In one embodiment of compositions of the present invention, conventional plasticizers such as is commonly used for poly(vinyl chloride) are substantially absent. In particular, plasticizers such as phthalates, adipates, trimellitate esters, polyesters, and other functionalized plasticizers as disclosed in, for example, U.S. Pat. No. 3,318,835; 4,409,345; WO 02/31044 A1; and PLASTICS ADDITIVES 499-504 (Geoffrey Pritchard, ed., Chapman & Hall 1998) are substantially absent. By "substantially absent", it is meant that these compounds are not added deliberately to the compositions and if present at all, are present at less than 0.5 weight %.

Oils such as naphthenic and other aromatic containing oils are present to less than 0.5 wt % of the compositions of the invention in a further embodiment. Also, aromatic moieties and carbon-carbon unsaturation are substantially absent from the non-functionalized plasticizers used in the present invention in yet another embodiment. Aromatic moieties include a compound whose molecules have the ring structure characteristic of benzene, naphthalene, phenanthrene, anthracene, etc. By "substantially absent", it is meant that these aromatic compounds or moieties are not added deliberately to the compositions, and if present, are present to less than 0.5 wt % of the composition.

In another embodiment of compositions of the present invention, conventional plasticizers, elastomers, or "compatibilizers" such as low molecular weight polyethylene are substantially absent. In particular, ethylene homopolymers and copolymers having a weight average molecular weight of from 500 to 10,000 are substantially absent. Such polyethylene compatibilizers are disclosed in, for example, WO 01/18109 A1. By "substantially absent", it is meant that these compounds are not added deliberately to the compositions and, if present, are present at less than 5 weight %, more preferably less than 4 weight %, more preferably less than 3 weight %, more preferably less than 2 weight %, more preferably less than 1 weight %, more preferably less than 0.5 weight %, based upon the weight of the polyolefin, the ethylene polymer or copolymer, and the NFP.

Preparing the Polyolefin/NFP Blend

The polyolefin suitable for use in the present invention can be in any physical form when used to blend with the NFP of the invention. In one embodiment, reactor granules, defined as the granules of polymer that are isolated from the polymerization reactor prior to any processing procedures, are used to blend with the NFP of the invention. The reactor granules have an average diameter of from 50 µm to 10 mm in one embodiment, and from 10 µm to 5 mm in another embodiment. In another embodiment, the polyolefin is in the form of pellets, such as, for example, having an average diameter of from 1 mm to 10 mm that are formed from melt extrusion of the reactor granules.

In one embodiment of the invention, the polyolefin suitable for the composition excludes physical blends of polypropylene with other polyolefins, and in particular, excludes physical blends of polypropylene with low molecular weight (500 to 10,000 g/mol) polyethylene or polyethylene copolymers, meaning that, low molecular weight polyethylene or polyethylene copolymers are not purposefully added in any amount to the polyolefin (e.g., polypropylene homopolymer or copolymer) compositions of the invention, such as is the case in, for example, WO 01/18109 A1.

The polyolefin and NFP can be blended by any suitable means, and are typically blended to obtain a homogeneous, single phase mixture. For example, they may be blended in a tumbler, static mixer, batch mixer, extruder, or a combination thereof. The mixing step may take place as part of a processing method used to fabricate articles, such as in the extruder on an injection molding machine or fiber line.

In one embodiment of compositions of the present invention, conventional plasticizers such as is commonly used for poly(vinyl chloride) are substantially absent. In particular, plasticizers such as phthalates, adipates, trimellitate esters, polyesters, and other functionalized plasticizers as disclosed in, for example, U.S. Pat. No. 3,318,835; 4,409,345; WO 02/31044 A1; and PLASTICS ADDITIVES 499-504 (Geoffrey Pritchard, ed., Chapman & Hall 1998) are substantially absent. By "substantially absent", it is meant that these compounds are not added deliberately to the compositions and if present at all, are present at less than 0.5 weight %.

Oils such as naphthenic and other aromatic containing oils are preferably present to less than 0.5 wt % of the compositions of the invention in a further embodiment. Also, aromatic moieties and carbon-carbon unsaturation are substantially absent from the non-functionalized plasticizers used in the present invention in yet another embodiment. Aromatic moieties include a compound whose molecules have the ring structure characteristic of benzene, naphthalene, phenanthrene, anthracene, etc. By "substantially absent", it is meant that these aromatic compounds or moieties are not added deliberately to the compositions, and if present, are present to less than 0.5 wt % of the composition.

In another embodiment of compositions of the present invention, conventional plasticizers, elastomers, or "compatibilizers" such as low molecular weight polyethylene are substantially absent. In particular, ethylene homopolymers and copolymers having a weight average molecular weight of from 500 to 10,000 are substantially absent. Such polyethylene compatibilizers are disclosed in, for example, WO 01/18109 A1. By "substantially absent", it is meant that these compounds are not added deliberately to the compositions and, if present, are present at less than 5 weight %, more preferably less than 4 weight %, more preferably less than 3 weight %, more preferably less than 2 weight %, more preferably less than 1 weight %, more preferably less than 0.5 weight %, based upon the weight of the polyolefin, the ethylene polymer or copolymer, and the NFP.

The polyolefin compositions of the present invention may also contain other additives. Those additives include adjuvants, oils, plasticizers, block, antiblock, color masterbatches, processing aids, neutralizers, lubricants, waxes, antioxidants, nucleating agents, acid scavengers, stabilizers, surfactants, anticorrosion agents, cavitating agents, blowing agents, other UV absorbers such as chain-breaking antioxidants, etc., quenchers, antistatic agents, slip agents, pigments, dyes, fillers and cure agents such as peroxide. The additives may be present in the typically effective amounts well known in the art, such as 0.001 weight % to 10 weight %. Preferably, dyes and other colorants common in the industry may be present from 0.01 to 10 wt % in one embodiment, and from 0.1 to 6 wt % in another embodiment. Suitable nucleating agents are disclosed by, for example, H. N. Beck in *Heterogeneous Nucleating Agents for Polypropylene Crystallization*, 11J. APPLIED POLY. SCI. 673-685 (1967) and in *Heterogeneous Nucleation Studies on Polypropylene*, 21 J. POLY. SCI.: POLY. LETTERS 347-351 (1983). Examples of suitable nucleating agents are sodium benzoate, sodium 2,2'-methylenebis(4,6-di-tert-butylphenyl) phosphate, aluminum 2,2'-methylenebis (4,6-di-tert-butylphenyl) phosphate, dibenzylidene sorbitol, di(p-tolylidene) sorbitol, di(p-ethylbenzylidene) sorbitol, bis (3,4-dimethylbenzylidene) sorbitol, and N',N'-dicyclohexyl-2,6-naphthalenedicarboxamide, and salts of disproportionated rosin esters. The foregoing list is intended to be illustrative of suitable choices of nucleating agents for inclusion in the instant formulations.

In particular, antioxidants and stabilizers such as organic phosphites, hindered amines, and phenolic antioxidants may be present in the polyolefin compositions of the invention from 0.001 to 2 wt % in one embodiment, and from 0.01 to 0.8 wt % in another embodiment, and from 0.02 to 0.5 wt % in yet another embodiment. Non-limiting examples of organic phosphites that are suitable are tris(2,4-di-tert-butylphenyl)phosphite (IRGAFOS 168) and di(2,4-di-tert-butylphenyl)pentaerithritol diphosphite (ULTRANOX 626). Non-limiting examples of hindered amines include poly[2-N,N'-di(2,2,6,6-tetramethyl-4-piperidinyl)-hexanediamine-4-(1-amino-1,1,3,3-tetramethylbutane)sym-triazine] (CHIMASORB 944); bis(1,2,2,6,6-pentamethyl-4-piperidyl) sebacate (TINUVIN 770). Non-limiting examples of phenolic antioxidants include pentaerythrityl tetrakis(3,5-di-tert-butyl-4-hydroxyphenyl) propionate (IRGANOX 1010); and 1,3,5-Tri(3,5-di-tert-butyl-4-hydroxybenzyl-isocyanurate (IRGANOX 3114). Preferred antioxidants include phenolic antioxidants, such as Irganox 1010, Irganox, 1076 both available from Ciba-Geigy.

Preferred oils include paraffinic or napthenic oils such as Primol 352, or Primol 876 available from ExxonMobil Chemical France, S. A. in Paris, France. More preferred oils include aliphatic napthenic oils, white oils or the like.

Fillers may be present from 0.1 to 50 wt % in one embodiment, and from 0.1 to 25 wt % of the composition in another embodiment, and from 0.2 to 10 wt % in yet another embodiment. Desirable fillers include but not limited to titanium dioxide, silicon carbide, silica (and other oxides of silica, precipitated or not), antimony oxide, lead carbonate, zinc white, lithopone, zircon, corundum, spinel, apatite, Barytes powder, barium sulfate, magnesiter, carbon black, dolomite, calcium carbonate, talc and hydrotalcite compounds of the ions Mg, Ca, or Zn with Al, Cr or Fe and $CO_3$ and/or $HPO_4$, hydrated or not; quartz powder, hydrochloric magnesium carbonate, glass fibers, clays, alumina, and other metal oxides and carbonates, metal hydroxides, chrome, phosphorous and brominated flame retardants, antimony trioxide, silica, silicone, and blends thereof. These fillers may particularly include any other fillers and porous fillers and supports known in the art, and may have the NFP of the invention pre-contacted, or pre-absorbed into the filler prior to addition to the polyolefin in one embodiment.

Preferred fillers, cavitating agents and/or nucleating agents include titanium dioxide, calcium carbonate, barium sulfate, silica, silicon dioxide, carbon black, sand, glass beads, mineral aggregates, talc, clay and the like.

More particularly, in one embodiment of the present invention, the NFP, or some portion of the NFP, may be blended with a filler, desirably a porous filler. The NFP and filler may be blended by, for example, a tumbler or other wet blending apparatus. The NFP and filler in this embodiment are blended for a time suitable to form a homogenous composition of NFP and filler, desirably from 1 minute to 5 hours in one embodiment. This NFP/filler blend may then be blended with the polyolefin useful in the invention in order to effectuate plastication of the polyolefin. In another embodiment, a porous filler may be contacted with the NFP, or some portion thereof, prior to contacting the filler with the polyolefin. In another embodiment, the porous filler, polyolefin and NFP are contacted simultaneously (or in the same blending apparatus). In any case, the NFP may be present from 0.1 to 60 wt % of the composition, and from 0.2 to 40 wt % in another embodiment, and from 0.3 to 20 wt % in yet another embodiment.

Fatty acid salts may also be present in the polyolefin compositions of the present invention. Such salts may be present from 0.001 to 1 wt % of the composition in one embodiment, and from 0.01 to 0.8 wt % in another embodiment. Examples of fatty acid metal salts include lauric acid, stearic acid, succinic acid, stearyl lactic acid, lactic acid, phthalic acid, benzoic acid, hydroxystearic acid, ricinoleic acid, naphthenic acid, oleic acid, palmitic acid, and erucic acid, suitable metals including Li, Na, Mg, Ca, Sr, Ba, Zn, Cd, Al, Sn, Pb and so forth. Preferable fatty acid salts are selected from magnesium stearate, calcium stearate, sodium stearate, zinc stearate, calcium oleate, zinc oleate, and magnesium oleate.

In some embodiments the plasticized polyolefins produced by this invention may be blended with one or more other polymers, including but not limited to, thermoplastic polymer(s) and/or elastomer(s).

By "thermoplastic polymer(s)" is meant a polymer that can be melted by heat and then cooled with out appreciable change in properties. Thermoplastic polymers typically include, but are not limited to, polyolefins, polyamides, polyesters, polycarbonates, polysulfones, polyacetals, polylactones, acrylonitrile-butadiene-styrene resins, polyphenylene oxide, polyphenylene sulfide, styrene-acrylonitrile resins, styrene maleic anhydride, polyimides, aromatic polyketones, or mixtures of two or more of the above. Preferred polyolefins include, but are not limited to, polymers comprising one or more linear, branched or cyclic $C_2$ to $C_{40}$ olefins, preferably polymers comprising propylene copolymerized with one or more $C_3$ to $C_{40}$ olefins, preferably a $C_3$ to $C_{20}$ alpha olefin, more preferably $C_3$ to $C_{10}$ alpha-olefins. More preferred polyolefins include, but are not limited to, polymers comprising ethylene including but not limited to ethylene copolymerized with a $C_3$ to $C_{40}$ olefin, preferably a $C_3$ to $C_{20}$ alpha olefin, more preferably propylene and or butene.

By elastomers is meant all natural and synthetic rubbers, including those defined in ASTM D1566. Examples of preferred elastomers include, but are not limited to, ethylene propylene rubber, ethylene propylene diene monomer rubber, styrenic block copolymer rubbers (including SI, SIS, SB, SBS, SIBS and the like, where S=styrene, I=isobutylene, and B=butadiene), butyl rubber, halobutyl rubber, copolymers of isobutylene and para-alkylstyrene, halogenated copolymers of isobutylene and para-alkylstyrene, natural rubber, polyisoprene, copolymers of butadiene with acrylonitrile, polychloroprene, alkyl acrylate rubber, chlorinated isoprene rubber, acrylonitrile chlorinated isoprene rubber, polybutadiene rubber (both cis and trans).

In another embodiment, the blend comprising the NFP may further be combined with one or more of polybutene, ethylene vinyl acetate, low density polyethylene (density 0.915 to less than 0.935 g/cm$^3$) linear low density polyethylene, ultra low density polyethylene (density 0.86 to less than 0.90 g/cm$^3$), very low density polyethylene (density 0.90 to less than 0.915 g/cm$^3$), medium density polyethylene (density 0.935 to less than 0.945 g/cm$^3$), high density polyethylene (density 0.945 to 0.98 g/cm$^3$), ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, crosslinked polyethylene, copolymers of ethylene and vinyl alcohol (EVOH), polymers of aromatic monomers such as polystyrene, poly-1 esters, polyacetal, polyvinylidine fluoride, polyethylene glycols and/or polyisobutylene. Preferred polymers include those available from Exxon Chemical Company in Baytown, Tex. under the tradenames EXCEED™ and EXACT™.

In another embodiment, tackifiers may be blended with the plasticized polyolefins of this invention. Examples of useful tackifiers include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, and hydrogenated rosin esters. In some embodiments the tackifier is hydrogenated. In other embodiments the tackifier is non-polar. (Non-polar meaning that the tackifier is substantially free of monomers having polar groups. Preferably the polar groups are not present, however if they are preferably they are not present at more that 5 weight %, preferably not more that 2 weight %, even more preferably no more than 0.5 weight %.) In some embodiments the tackifier has a softening point (Ring and Ball, as measured by ASTM E-28) of 80° C. to 140° C., preferably 100° C. to 130° C. The tackifier, if present, is typically present at about 1 weight % to about 50 weight %, based upon the weight of the blend, more preferably 10 weight % to 40 weight %, even more preferably 20 weight % to 40 weight %. Preferably however, tackifier is not present, or if present, is present at less than 10 weight %, preferably less than 5 weight %, more preferably at less than 1 weight %.

More particularly, the components of the polyolefinic composition of the present invention may be blended by any suitable means to form the plasticized polyolefin, which is then suitable for further processing into useful articles. In one aspect of the invention, the polyolefin and NFP are blended, or melt blended, in an apparatus such as an extruder or batch mixer. The polyolefin may also be blended with the NFP using a tumbler, double-cone blender, ribbon blender, or other suitable blender. In yet another embodiment, the polyolefin and NFP are blended by a combination of, for example, a tumbler, followed by melt blending in an extruder. Extrusion technology for polypropylene is described in more detail in, for example, PLASTICS EXTRUSION TECHNOLOGY 26-37 (Friedhelm Hensen, ed. Hanser Publishers 1988) and in POLYPROPYLENE HANDBOOK 304-348 (Edward P. Moore, Jr. ed., Hanser Publishers 1996).

More particularly, the components of the polyolefinic composition of the present invention may be blended in solution by any suitable means to form the plasticized polyolefin, by using a solvent that dissolves both components to a significant extent. The blending may occur at any temperature or pressure where the NFP and the polyolefin remain in solution. Preferred conditions include blending at high temperatures, such as 20° C. or more, preferably 40° C.

or more over the melting point of the polyolefin. For example iPP would typically be solution blended with the NFP at a temperature of 200° C. or more, preferably 220° C. or more. Such solution blending would be particularly useful in processes where the polyolefin is made by solution process and the NFP is added directly to the finishing train, rather than added to the dry polymer in another blending step altogether. Such solution blending would also be particularly useful in processes where the polyolefin is made in a bulk or high pressure process where the both the polymer and the NFP were soluble in the monomer. As with the solution process the NFP is added directly to the finishing train, rather than added to the dry polymer in another blending step altogether.

The polyolefin suitable for use in the present invention can be in any physical form when used to blend with the NFP of the invention. In one embodiment, reactor granules, defined as the granules of polymer that are isolated from the polymerization reactor, are used to blend with the NFP of the invention. The reactor granules have an average diameter of from 10 µm to 5 mm, and from 50 µm to 10 mm in another embodiment. Alternately, the polyolefin is in the form of pellets, such as, for example, having an average diameter of from 1 mm to 6 mm that are formed from melt extrusion of the reactor granules.

One method of blending the NFP with the polyolefin is to contact the components in a tumbler, the polyolefin being in the form of reactor granules. This works particularly well with polypropylene homopolymer and random copolymer. This can then be followed, if desired, by melt blending in an extruder. Another method of blending the components is to melt blend the polyolefin pellets with the NFP directly in an extruder or Brabender.

Thus, in the cases of injection molding of various articles, simple solid state blends of the pellets serve equally as well as pelletized melt state blends of raw polymer granules, of granules with pellets, or of pellets of the two components since the forming process includes a remelting and mixing of the raw material. In the process of compression molding of medical devices, however, little mixing of the melt components occurs, and a pelletized melt blend would be preferred over simple solid state blends of the constituent pellets and/or granules. Those skilled in the art will be able to determine the appropriate procedure for blending of the polymers to balance the need for intimate mixing of the component ingredients with the desire for process economy.

Applications

The resultant plasticized polyolefin of the present invention may be processed by any suitable means such as by calendering, casting, coating, compounding, extrusion, foamed, laminated, blow molding, compression molding, injection molding, thermoforming, transfer molding, cast molding, rotational molding, casting such as for films, spun or melt bonded such as for fibers, or other forms of processing such as described in, for example, PLASTICS PROCESSING (Radian Corporation, Noyes Data Corp. 1986). More particularly, with respect to the physical process of producing the blend, sufficient mixing should take place to assure that a uniform blend will be produced prior to conversion into a finished product.

The compositions of this invention (and blends thereof as described above) may be used in any known thermoplastic or elastomer application. Examples include uses in molded parts, films, tapes, sheets, tubing, hose, sheeting, wire and cable coating, adhesives, shoesoles, bumpers, gaskets, bellows, films, fibers, elastic fibers, nonwovens, spunbonds, sealants, surgical gowns and medical devices.

These devices may be made or formed by any useful forming means for forming polyolefins. This will include, at least, molding including compression molding, injection molding, blow molding, and transfer molding; film blowing or casting; extrusion, and thermoforming; as well as by lamination, pultrusion, protrusion, draw reduction, rotational molding, spinbonding, melt spinning, melt blowing; or combinations thereof. Use of at least thermoforming or film applications allows for the possibility of and derivation of benefits from uniaxial or biaxial orientation of the radiation tolerant material.

Adhesives

The polymers of this invention or blends thereof can be used as adhesives, either alone or combined with tackifiers. Preferred tackifiers are described above. The tackifier is typically present at about 1 weight % to about 50 weight %, based upon the weight of the blend, more preferably 10 weight % to 40 weight %, even more preferably 20 weight % to 40 weight %. Other additives, as described above, may be added also.

The adhesives of this invention can be used in any adhesive application, including but not limited to, disposables, packaging, laminates, pressure sensitive adhesives, tapes labels, wood binding, paper binding, non-wovens, road marking, reflective coatings, and the like. In a preferred embodiment the adhesives of this invention can be used for disposable diaper and napkin chassis construction, elastic attachment in disposable goods converting, packaging, labeling, bookbinding, woodworking, and other assembly applications. Particularly preferred applications include: baby diaper leg elastic, diaper frontal tape, diaper standing leg cuff, diaper chassis construction, diaper core stabilization, diaper liquid transfer layer, diaper outer cover lamination, diaper elastic cuff lamination, feminine napkin core stabilization, feminine napkin adhesive strip, industrial filtration bonding, industrial filter material lamination, filter mask lamination, surgical gown lamination, surgical drape lamination, and perishable products packaging.

Films

The compositions described above and the blends thereof may be formed into monolayer or multilayer films. These films may be formed by any of the conventional techniques known in the art including extrusion, co-extrusion, extrusion coating, lamination, blowing and casting. The film may be obtained by the flat film or tubular process which may be followed by orientation in an uniaxial direction or in two mutually perpendicular directions in the plane of the film. One or more of the layers of the film may be oriented in the transverse and/or longitudinal directions to the same or different extents. This orientation may occur before or after the individual layers are brought together. For example a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, preferably between 5 and 7, and in the Transverse Direction (TD) at a ratio of up to 15 preferably 7 to 9. However in another embodiment the film is oriented to the same extent in both the MD and TD directions.

In another embodiment the layer comprising the plasticized polyolefin composition of this invention (and/or blends thereof) may be combined with one or more other layers. The other layer(s) may be any layer typically included in multilayer film structures. For example the other layer or layers may be:

1. Polyolefins

Preferred polyolefins include homopolymers or copolymers of C2 to C40 olefins, preferably C2 to C20 olefins, preferably a copolymer of an alpha-olefin and another olefin or alpha-olefin (ethylene is defined to be an alpha-olefin for purposes of this invention). Preferably homopolyethylene, homopolypropylene, propylene copolymerized with ethylene and or butene, ethylene copolymerized with one or more of propylene, butene or hexene, and optional dienes. Preferred examples include thermoplastic polymers such as ultra low density polyethylene, very low density polyethylene, linear low density polyethylene, low density polyethylene, medium density polyethylene, high density polyethylene, polypropylene, isotactic polypropylene, highly isotactic polypropylene, syndiotactic polypropylene, random copolymer of propylene and ethylene and/or butene, elastomers such as ethylene propylene rubber, ethylene propylene diene monomer rubber, neoprene, and blends of thermoplastic polymers and elastomers, such as for example, thermoplastic elastomers and rubber toughened plastics.

2. Polar Polymers

Preferred polar polymers include homopolymers and copolymers of esters, amides, actates, anhydrides, copolymers of a C2 to C20 olefin, such as ethylene and/or propylene and/or butene with one or more polar monomers such as acetates, anhydrides, esters, alcohol, and or acrylics. Preferred examples include polyesters, polyamides, ethylene vinyl acetate copolymers, and polyvinyl chloride.

3. Cationic polymers Preferred cationic polymers include polymers or copolymers of geminally disubstituted olefins, alpha-heteroatom olefins and/or styrenic monomers. Preferred geminally disubstituted olefins include isobutylene, isopentene, isoheptene, isohexane, isooctene, isodecene, and isododecene. Preferred alpha-heteroatom olefins include vinyl ether and vinyl carbazole, preferred styrenic monomers include styrene, alkyl styrene, para-alkyl styrene, alpha-methyl styrene, chloro-styrene, and bromo-para-methyl styrene. Preferred examples of cationic polymers include butyl rubber, isobutylene copolymerized with para methyl styrene, polystyrene, and poly-alpha-methyl styrene.

4. Miscellaneous

Other preferred layers can be paper, wood, cardboard, metal, metal foils (such as aluminum foil and tin foil), metallized surfaces, glass (including silicon oxide (SiO.x)coatings applied by evaporating silicon oxide onto a film surface), fabric, spunbonded fibers, and non-wovens (particularly polypropylene spun bonded fibers or non-wovens), and substrates coated with inks, dyes, pigments, and the like.

The films may vary in thickness depending on the intended application, however films of a thickness from 1 to 250 μm are usually suitable. Films intended for packaging are usually from 10 to 60 micron thick. The thickness of the sealing layer is typically 0.2 to 50 μm. There may be a sealing layer on both the inner and outer surfaces of the film or the sealing layer may be present on only the inner or the outer surface.

Additives such as block, antiblock, antioxidants, pigments, fillers, processing aids, UV stabilizers, neutralizers, lubricants, surfactants and/or nucleating agents may also be present in one or more than one layer in the films. Preferred additives include silicon dioxide, titanium dioxide, polydimethylsiloxane, talc, dyes, wax, calcium sterate, carbon black, low molecular weight resins and glass beads.

In another embodiment one more layers may be modified by corona treatment, electron beam irradiation, gamma irradiation, or microwave irradiation. In a preferred embodiment one or both of the surface layers is modified by corona treatment.

The films described herein may also comprise from 5 to 60 weight %, based upon the weight of the polymer and the resin, of a hydrocarbon resin. The resin may be combined with the polymer of the seal layer(s) or may be combined with the polymer in the core layer(s). The resin preferably has a softening point above 100° C., even more preferably from 130 to 180° C. Preferred hydrocarbon resins include those described above. The films comprising a hydrocarbon resin may be oriented in uniaxial or biaxial directions to the same or different degrees.

Molded Products

The plasticized polyolefin composition described above may also be used to prepare molded products in any molding process, including but not limited to, injection molding, gas-assisted injection molding, extrusion blow molding, injection blow molding, injection stretch blow molding, compression molding, rotational molding, foam molding, thermoforming, sheet extrusion, and profile extrusion. The molding processes are well known to those of ordinary skill in the art.

The compositions described herein may be shaped into desirable end use articles by any suitable means known in the art. Thermoforming, vacuum forming, blow molding, rotational molding, slush molding, transfer molding, wet lay-up or contact molding, cast molding, cold forming matched-die molding, injection molding, spray techniques, profile co-extrusion, or combinations thereof are typically used methods.

Thermoforming is a process of forming at least one pliable plastic sheet into a desired shape. An embodiment of a thermoforming sequence is described, however this should not be construed as limiting the thermoforming methods useful with the compositions of this invention. First, an extrudate film of the composition of this invention (and any other layers or materials) is placed on a shuttle rack to hold it during heating. The shuttle rack indexes into the oven which pre-heats the film before forming. Once the film is heated, the shuttle rack indexes back to the forming tool. The film is then vacuumed onto the forming tool to hold it in place and the forming tool is closed. The forming tool can be either "male" or "female" type tools. The tool stays closed to cool the film and the tool is then opened. The shaped laminate is then removed from the tool.

Thermoforming is accomplished by vacuum, positive air pressure, plug-assisted vacuum forming, or combinations and variations of these, once the sheet of material reaches thermoforming temperatures, typically of from 140° C. to 185° C. or higher. A pre-stretched bubble step is used, especially on large parts, to improve material distribution. In one embodiment, an articulating rack lifts the heated laminate towards a male forming tool, assisted by the application of a vacuum from orifices in the male forming tool. Once the laminate is firmly formed about the male forming tool, the thermoformed shaped laminate is then cooled, typically by blowers. Plug-assisted forming is generally used for small, deep drawn parts. Plug material, design, and timing can be critical to optimization of the process. Plugs made from insulating foam avoid premature quenching of the plastic. The plug shape is usually similar to the mold cavity, but smaller and without part detail. A round plug bottom will usually promote even material distribution and uniform side-wall thickness. For a semicrystalline polymer such as polypropylene, fast plug speeds generally provide the best material distribution in the part.

The shaped laminate is then cooled in the mold. Sufficient cooling to maintain a mold temperature of 30° C. to 65° C. is desirable. The part is below 90° C. to 100° C. before ejection in one embodiment. For the good behavior in thermoforming, the lowest melt flow rate polymers are desirable. The shaped laminate is then trimmed of excess laminate material.

Blow molding is another suitable forming means, which includes injection blow molding, multi-layer blow molding, extrusion blow molding, and stretch blow molding, and is especially suitable for substantially closed or hollow objects, such as, for example, gas tanks and other fluid containers. Blow molding is described in more detail in, for example, CONCISE ENCYCLOPEDIA OF POLYMER SCIENCE AND ENGINEERING 90-92 (Jacqueline I. Kroschwitz, ed., John Wiley & Sons 1990).

In yet another embodiment of the formation and shaping process, profile co-extrusion can be used. The profile co-extrusion process parameters are as above for the blow molding process, except the die temperatures (dual zone top and bottom) range from 150° C.-235° C., the feed blocks are from 90° C.-250° C., and the water cooling tank temperatures are from 10° C.-40° C.

One embodiment of an injection molding process is described as follows. The shaped laminate is placed into the injection molding tool. The mold is closed and the substrate material is injected into the mold. The substrate material has a melt temperature between 200° C. and 300° C. in one embodiment, and from 215° C. and 250° C. and is injected into the mold at an injection speed of between 2 and 10 seconds. After injection, the material is packed or held at a predetermined time and pressure to make the part dimensionally and aesthetically correct. Typical time periods are from 5 to 25 seconds and pressures from 1,380 kPa to 10,400 kPa. The mold is cooled between 10° C. and 70° C. to cool the substrate. The temperature will depend on the desired gloss and appearance desired. Typical cooling time is from 10 to 30 seconds, depending on part on the thickness. Finally, the mold is opened and the shaped composite article ejected.

Likewise, molded articles may be fabricated by injecting molten polymer into a mold that shapes and solidifies the molten polymer into desirable geometry and thickness of molded articles. Sheet may be made either by extruding a substantially flat profile from a die, onto a chill roll, or alternatively by calendaring. Sheet will generally be considered to have a thickness of from 10 mils to 100 mils (254 µm to 2540 µm), although sheet may be substantially thicker. Tubing or pipe may be obtained by profile extrusion for uses in medical, potable water, land drainage applications or the like. The profile extrusion process involves the extrusion of molten polymer through a die. The extruded tubing or pipe is then solidified by chill water or cooling air into a continuous extruded articles. The tubing will generally be in the range of from 0.31 cm to 2.54 cm in outside diameter, and have a wall thickness of in the range of from 254 µm to 0.5 cm. The pipe will generally be in the range of from 2.54 cm to 254 cm in outside diameter, and have a wall thickness of in the range of from 0.5 cm to 15 cm. Sheet made from the products of an embodiment of a version of the present invention may be used to form containers. Such containers may be formed by thermoforming, solid phase pressure forming, stamping and other shaping techniques. Sheets may also be formed to cover floors or walls or other surfaces.

In an embodiment of the thermoforming process, the oven temperature is between 160° C. and 195° C., the time in the oven between 10 and 20 seconds, and the die temperature, typically a male die, between 10° C. and 71° C. The final thickness of the cooled (room temperature), shaped laminate is from 10 µm to 6000 µm in one embodiment, from 200 µm to 6000 µm in another embodiment, and from 250 µm to 3000 µm in yet another embodiment, and from 500 µm to 1550 µm in yet another embodiment, a desirable range being any combination of any upper thickness limit with any lower thickness limit.

In an embodiment of the injection molding process, wherein a substrate material in injection molded into a tool including the shaped laminate, the melt temperature of the substrate material is between 230° C. and 255° C. in one embodiment, and between 235° C. and 250° C. in another embodiment, the fill time from 2 to 10 seconds in one embodiment, from 2 to 8 seconds in another embodiment, and a tool temperature of from 25° C. to 65° C. in one embodiment, and from 27° C. and 60° C. in another embodiment. In a desirable embodiment, the substrate material is at a temperature that is hot enough to melt any tie-layer material or backing layer to achieve adhesion between the layers.

In yet another embodiment of the invention, the compositions of this invention may be secured to a substrate material using a blow molding operation. Blow molding is particularly useful in such applications as for making closed articles such as fuel tanks and other fluid containers, playground equipment, outdoor furniture and small enclosed structures. In one embodiment of this process, Compositions of this invention are extruded through a multi-layer head, followed by placement of the uncooled laminate into a parison in the mold. The mold, with either male or female patterns inside, is then closed and air is blown into the mold to form the part.

It will be understood by those skilled in the art that the steps outlined above may be varied, depending upon the desired result. For example, the an extruded sheet of the compositions of this invention may be directly thermoformed or blow molded without cooling, thus skipping a cooling step. Other parameters may be varied as well in order to achieve a finished composite article having desirable features.

Preferred articles made using the plasticized polyolefins of this invention include cookware, storageware, toys, medical devices, sterilizable medical devices, sterilization containers, sheets, crates, containers, packaging, wire and cable jacketing, pipes, geomembranes, sporting equipment, chair mats, tubing, profiles, instrumentation sample holders and sample windows, outdoor furniture (e.g., garden furniture) playground equipment, automotive, boat and water craft components, and other such articles. In particular, the compositions are suitable for automotive components such as bumpers, grills, trim parts, dashboards and instrument panels, exterior door and hood components, spoiler, wind screen, hub caps, mirror housing, body panel, protective side molding, and other interior and external components associated with automobiles, trucks, boats, and other vehicles.

Non-Wovens and Fibers

The plasticized polyolefin composition described above may also be used to prepare the nonwoven fabrics and fibers in any nonwoven fabric and fiber making process, including but not limited to, melt blowing, spunbonding, film aperturing, and staple fiber carding. A continuous filament process may also be used. Preferably a spunbonding process is used. The spunbonding process is well known in the art. Generally it involves the extrusion of fibers through a spinneret. These fibers are then drawn using high velocity air and laid on an endless belt. A calender roll is generally then used to heat the web and bond the fibers to one another although other techniques may be used such as sonic bonding and adhesive bonding.

Fiber Preparation

The formation of woven and nonwoven articles from the polyolefin/NFP blends described herein typically requires the manufacture of fibers by extrusion followed by weaving or bonding. The extrusion process is typically accompanied by mechanical or aerodynamic drawing of the fibers. Essentially all fibers are oriented both during the extrusion process as well as during the process of manufacture of the non woven article.

a. Conventional Fine Denier PP Fibers

The three more conventional PP fiber operations, continuous filament, bulked continuous filament, and staple, are are useful as means for preparing fibers of the blends of the present invention. Typically the molten blend is extruded through the holes in a die (spinneret) between 0.3 mm to 0.8 mm (10 mil to 30 mil) in diameter. Low melt viscosity of the polymer blend is preferred and is typically achieved through the use of high melt temperature (230° C. to 280° C.) and high melt flow rates (15 g/10 min to 40 g/10 min). A relatively large extruder is typically equipped with a manifold to distribute a high output of molten blend to a bank of eight to twenty spinnerets. Each spinhead is typically equipped with a separate gear pump to regulate output through that spinhead; a filter pack, supported by a "breaker plate;" and the spinneret plate within the head. The number of holes in the spinneret plate determines the number of filaments in a yarn and varies considerably with the different yarn constructions, but it is typically in the range of 50 to 250. The holes are typically grouped into round, annular, or rectangular patterns to assist in good distribution of the quench air flow.

b. Continuous Filament

Continuous filament yarns typically range from 40 denier to 2,000 denier (denier=number of grams/9000 yd). Filaments typically range from 1 to 20 dpf, but can be larger. Spinning speeds are typically 800 m/min to 1500 m/min (2500 ft/min to 5000 ft/min). The filaments are drawn at draw ratios of 3:1 or more (one- or two-stage draw) and wound onto a package. Two-stage drawing allows higher draw ratios to be achieved. Winding speeds are 2,000 m/min to 3,500 n/min (6,600 ft/min to 11,500 ft/min). Spinning speeds in excess of 900 m/min (3000 ft/min) require a NMWD to get the best spinnability with the finer filaments.

c. Bulked Continuous Filament

Bulked Continuous Filament fabrication processes fall into two basic types, one-step and two step. In the older, two-step process, an undrawn yarn is spun at less than 1,000 m/min (3,300 ft/min), usually 750 m/min, and placed on a package. The yarn is drawn (usually in two stages) and "bulked" on a machine called a texturizer. Winding and drawing speeds are limited by the bulking or texturizing device to 2,500 m/min (8,200 ft/mim) or less. Typically if secondary crystallization occurs in the two-step CF process, then one typically promptly uses draw texturizing. The most common process today is the one-step spin/draw/text (SDT) process. This process provides better economics, efficiency and quality than the two-step process. It is similar to the one-step CF process, except that the bulking device is in-line. Bulk or texture changes yarn appearance, separating filaments and adding enough gentle bends and folds to make the yarn appear fatter (bulkier).

d. Staple Fiber

There are two basic staple fiber fabrication processes: traditional and compact spinning. The traditional process involves two steps: 1) producing, applying finish, and winding followed by 2) drawing, a secondary finish application, crimping, and cutting into staple. Filaments can range from 1.5 dpf to >70 dpf, depending on the application. Staple length can be as short as 7 mm or as long as 200 mm (0.25 in. to 8 in.) to suit the application. For many applications the fibers are crimped. Crimping is accomplished by over-feeding the tow into a steam-heated stuffer box with a pair of nip rolls. The over-feed folds the tow in the box, forming bends or crimps in the filaments. These bends are heat-set by steam injected into the box.

e. Melt-Blown Fibers

Melt blown fibers can make very fine filaments and produce very lightweight fabrics with excellent uniformity. The result is often a soft fabric with excellent "barrier" properties. In the melt blown process molten polymer moves from the extruder to the special melt blowing die. As the molten filaments exit the die, they are contacted by high temperature, high velocity air (called process or primary air). This air rapidly draws and, in combination with the quench air, solidifies the filaments. The entire fiber forming process generally takes place within 7 mm (0.25 in.) of the die. The fabric is formed by blowing the filaments directly onto a forming wire, 200 mm to 400 mm (8 in. to 15 in.) from the spinnerets.

Melt blown microfibers useful in the present invention can be prepared as described in Van A. Wente, "Superfine Thermoplastic Fibers," Industrial Engineering Chemistiy, vol. 48, pp. 1342-1346 and in Report No. 4364 of the Naval Research Laboratories, published May 25, 1954, entitled "Manufacture of Super Fine Organic Fibers" by Van A. Wente et al. In some preferred embodiments, the microfibers are used in filters. Such blown microfibers typically have an effective fiber diameter of from about 3 to 30 micrometers preferably from about 7 to 15 micrometers, as calculated according to the method set forth in Davies, C. N., "The Separation of Airborne Dust and Particles," Institution of Mechanical Engineers, London, Proceedings 1B, 1952.

f. Spunbonded Fibers

Fiber formation may also be accomplished by extrusion of the molten polymer from either a large spinneret having several thousand holes or with banks of smaller spinnerets containing as few as 40 holes. After exiting the spinneret, the molten fibers are quenched by a cross-flow air quench system, then pulled away from the spinneret and attenuated (drawn) by high pressure air. There are two methods of air attenuation, both of which use the venturi effect. The first draws the filament using an aspirator slot (slot draw), which runs the width of the machine. The second method draws the filaments through a nozzle or aspirator gun. Filaments formed in this manner are collected on a screen ("wire") or porous forming belt to form the fabric. The fabric is then passed through compression rolls and then between heated calender rolls where the raised lands on one roll bond the fabric at points covering 20% to 40% of its area.

Annealing

In additional embodiments, the mechanical properties of fibers comprising the blends of this inventioncan be improved by the annealing the fibers or the non-woven materials made from the blends of this invention. Annealing is often combined with mechanical orientation, although annealing is preferred. Annealing partially relieves the internal stress in the stretched fiber and restores the elastic recovery properties of the blend in the fiber. Annealing has been shown to lead to significant changes in the internal organization of the crystalline structure and the relative ordering of the amorphous and semicrystalline phases. Annealing typically leads to improved elastic properties. The fiber or fabirc is preferably annealed at a temperature of at least 40° F., preferably at least 20° F. above room temperature (but slightly below the crystalline melting point of the blend). Thermal annealing of the blend is conducted by maintaining the polymer blends or the articles made from a such a blend at temperature between room temperature to a maximum of 160° C. or more preferably to a maximum of 130° C. for a period between 5 minutes to less than 7 days. A typical annealing period is 3 days at 50° C. or 5 minutes at 100° C. While the annealing is done in the absence of mechanical orientation, the latter can be a part of the annealing process on the fiber (past the extrusion operation). Mechanical orientation can be done by the temporary, forced extension of the fiber for a short period of time before it is allowed to relax in the absence of the extensional forces. Oriented fibers are conducted by maintaining the fibers or the articles made from a blend at an extension of 100% to 700% for a period of 0.1 seconds to 24 hours. A typical orientation is an extension of 200% for a momentary period at room temperature.

For orientation, a fiber at an elevated temperature (but below the crystalline melting point of the polymer) is passed from a feed roll of fiber around two rollers driven at different surface speeds and finally to a take-up roller. The driven roller closest to the take-up roll is driven faster than the driven roller closest to the feed roll, such that the fiber is stretched between the driven rollers. The assembly may include a roller intermediate the second roller and take-up roller to cool the fiber. The second roller and the take-up roller may be driven at the same peripheral speeds to maintain the fiber in the stretched condition. If supplementary cooling is not used, the fiber will cool to ambient temperature on the take up roll.

For more information on fiber and non-woven production please see Polypropylene Handbook, E. P. Moore, Jr., et al., Hanser/Gardner Publications, Inc. New York, 1996, pages 314 to 322, which is incorporated by reference herein.

Nonwoven Web

In a preferred embodiment, a nonwoven fiber web is prepared from the polyolefin/NFP blends of this invention. The fibers employed in such a web typically and preferably have denier ranging from about 0.5 to about 10 (about 0.06 to about 11 tex), although higher denier fibers may also be employed. Fibers having denier from about 0.5 to 3 (0.06 to about 3.33 tex) are particularly preferred. ("Denier" means weight in grams of 9000 meters of fiber, whereas "tex" means weight in grams per kilometer of fiber.) Fiber stock having a length ranging from about 0.5 to about 10 cm is preferably employed as a starting material, particularly fiber lengths ranging from about 3 to about 8 cm. Nonwoven webs of fibers may be made using methods well documented in the nonwoven literature (see for example Turbak, A. "Nonwovens: An Advanced Tutorial", Tappi Press, Atlanta, Ga., (1989). The uncoated (i.e., before application of any binder) web should have a thickness in the range of about 10 to 100 mils (0.254 to 2.54 mm), preferably 30 to 70 mils (0.762 to 1.778 mm), more preferably 40 to 60 mils (1.02 to 1.524 mm). These preferred thicknesses may be achieved either by the carding/crosslapping operation or via fiber entanglement (e.g., hydroentanglement, needling, and the like). The basis weight of the uncoated web preferably ranges from about 50 $g/m^2$ up to about 250 $g/m^2$. In some embodiments, one may improve the tensile and tear strength of the inventive articles, and reduce lint on the surface of the articles, by entangling (such as by needletacking, hydroentanglement, and the like) the nonwoven web, or calendering the uncoated and/or coated and cured nonwoven web. Hydroentanglement may be employed in cases where fibers are water insoluble. Calendering of the nonwoven web at temperatures from about 5 to about 40° C. below the melting point of the fiber may reduce the likelihood of lint attaching to the surface of the utimate articles and provide a smooth surface. Embossing of a textured pattern onto the nonwoven web may be performed simultaneously with calendering, or in a subsequent step.

In addition to the polyolefins and the NFP's of this invention, it may also be desirable to add colorants (especially pigments), softeners (such as ethers and alcohols), fragrances, fillers (such as for example silica, alumina, and titanium dioxide particles), and bactericidal agents (for example iodine, quaternary ammonium salts, and the like) to the blends.

Likewise the nonwoven webs and fibers may be coated with other materials, such as binders, adhesives, reflectants, and the like. Coating of the nonwoven web or the fiber may be accomplished by methods known in the art, including roll coating, spray coating, immersion coating, gravure coating, or transfer coating. The coating weight as a percentage of the total wiping article may be from about 1% to about 95%, preferably from about 10% to about 60%, more preferably 20 to 40%.

Staple fibers may also be present in the nonwoven web. The presence of staple fibers generally provides a more lofty, less dense web than a web of only blown microfibers. Preferably, no more than about 90 weight percent staple fibers are present, more preferably no more than about 70 weight percent. Such webs containing staple fiber are disclosed in U.S. Pat. No. 4,118,531 (Hauser) which is incorporated herein by reference.

Sorbent particulate material such as activated carbon or alumina may also be included in the web. Such particles may be present in amounts up to about 80 volume percent of the contents of the web. Such particle-loaded webs are described, for example, in U.S. Pat. No. 3,971,373 (Braun), U.S. Pat. No. 4,100,324 (Anderson) and U.S. Pat. No. 4,429,001 (Kolpin et al.), which are incorporated herein by reference.

The fibers and nonwoven webs prepared using the blends of this invention can be formed into fabrics, garments, clothing, medical garments, surgical gowns, surgical drapes, diapers, training pants, sanitary napkins, panty liners, incontinent wear, bed pads, bags, packaging material, packages, swimwear, body fluid impermeable backsheets, body fluid impermeable layers, body fluid permeable layers, body fluid permeable covers, absorbents, tissues, nonwoven composites, liners, cloth linings, scrubbing pads, face masks, respirators, air filters, vacuum bags, oil and chemical spill sorbents, thermal insulation, first aid dressings, medical wraps, fiberfill, outerwear, bed quilt stuffing, furniture padding, filter media, scrubbing pads, wipe materials, hosiery, automotive seats, upholstered furniture, carpets, carpet backing, filter media, disposable wipes, diaper coverstock, gardening fabric, geomembranes, geotextiles, sacks, housewrap, vaopr barriers, breathable clothing, envelops, tamper evident fabrics, protective packaging, and coasters.

The fibers prepared using the blends of this invention can be formed into yarns, woven fabrics, nonwoven fabrics, hook and loop fasteners, fabrics, garments, clothing, medical garments, surgical gowns, surgical drapes, diapers, training pants, sanitary napkins, panty liners, incontinent wear, bed pads, bags, packaging material, packages, swimwear, body fluid impermeable backsheets, body fluid impermeable layers, body fluid permeable layers, body fluid permeable covers, absorbents, tissues, nonwoven composites, liners, cloth linings, scrubbing pads, face masks, respirators, air filters, vacuum bags, oil and chemical spill sorbents, thermal insulation, first aid dressings, medical wraps, fiberfill, outerwear, bed quilt stuffing, furniture padding, filter media, scrubbing pads, wipe materials, hosiery, automotive seats, upholstered furniture, carpets, carpet backing, filter media, disposable wipes, diaper coverstock, gardening fabric, geomembranes, geotextiles, sacks, housewrap, vaopr barriers, breathable clothing, envelops, tamper evident fabrics, protective packaging, and coasters.

Test Methods

Dynamic Mechanical Thermal Analysis

The glass transition temperature ($T_g$) and storage modulus (E') were measured using dynamic mechanical thermal analysis (DMTA). This test provides information about the small-strain mechanical response (relaxation behavior) of a sample as a function of temperature over a temperature range that includes the glass transition region and the visco-elastic region prior to melting.

Typically, samples were tested using a three point bending configuration (TA Instruments DMA 2980). A solid rectangular compression molded bar was placed on two fixed supports; a movable clamp applied a periodic deformation to the sample midpoint at a frequency of 1 Hz and an amplitude of 20 μm. The sample was initially cooled to −130° C. then heated to 60° C. at a heating rate of 3° C./min. In some cases, compression molded bars were tested using other deformation configurations, namely dual cantilever bending and tensile elongation (Rheometrics RSAII). The periodic deformation under these configurations was applied at a frequency of 1 Hz and strain amplitude of 0.05%. The sample was cooled to −130° C. and then heated to 60° C. at a rate of 2° C./min. The slightly difference in heating rate does not influence the glass transition temperature measurements significantly.

The output of these DMTA experiments is the storage modulus (E') and loss modulus (E"). The storage modulus measures the elastic response or the ability of the material to store energy, and the loss modulus measures the viscous response or the ability of the material to dissipate energy. Tanδ is the ratio of E"/E' and gives a measure of the damping ability of the material. The beginning of the broad glass transition (β-relaxation) is identified as the extrapolated tangent to the Tanδ peak. In addition, the peak temperature and area under the peak are also measured to more fully characterize the transition from glassy to visco-elastic region.

Differential Scanning Calorimetry

Crystallization temperature ($T_c$) and melting temperature ($T_m$) were measured using Differential Scanning Calorimetry (DSC). This analysis was conducted using either a TA Instruments MDSC 2920 or a Perkin Elmer DSC7. Typically, 6 to 10 mg of molded polymer or plasticized polymer was sealed in an aluminum pan and loaded into the instrument at room temperature. Melting data (first heat) were acquired by heating the sample to at least 30° C. above its melting temperature at a heating rate of 10° C./min. This provides information on the melting behavior under as-molded conditions, which can be influenced by thermal history as well as any molded-in orientation or stresses. The sample was then held for 10 minutes at this temperature to destroy its thermal history. Crystallization data was acquired by cooling the sample from the melt to at least 50° C. below the crystallization temperature at a cooling rate of 10° C./min. The sample was then held at 25° C. for 10 minutes, and finally heated at 10° C./min to acquire additional melting data (second heat). This provides information about the melting behavior after a controlled thermal history and free from potential molded-in orientation and stress effects. The endothermic melting transition (first and second heat) and exothermic crystallization transition were analyzed for onset of transition and peak temperature. The melting temperatures reported in the tables are the peak melting temperatures from the second heat unless otherwise indicated. For polymers displaying multiple peaks, the higher melting peak temperature is reported.

Areas under the curve was used to determine the heat of fusion ($\Delta H_f$) which can be used to calculate the degree of crystallinity. A value of 207 J/g was used as the equilibrium heat of fusion for 100% crystalline polypropylene (obtained from B. Wunderlich, "Thermal Analysis", Academic Press, Page 418, 1990). The percent crystallinity is calculated using the formula, [area under the curve (J/g)/207 (J/g)] *100.

Size-Exclusion Chromatography of Polymers

Molecular weight distribution was characterized using Size-Exclusion Chromatography (SEC). Molecular weight (weight-average molecular weight, Mw, and number-average molecular weight, Mn) were determined using a High Temperature Size Exclusion Chromatograph (either from Waters Corporation or Polymer Laboratories), equipped with a differential refractive index detector (DRI), an online light scattering detector, and a viscometer. Experimental details not described below, including how the detectors were calibrated, are described in: T. Sun, P. Brant, R. R. Chance, and W. W. Graessley, Macromolecules, Volume 34, Number 19, 6812-6820, (2001).

Three Polymer Laboratories PLgel 10 mm Mixed-B columns were used. The nominal flow rate was 0.5 cm³/min, and the nominal injection volume was 300 μL. The various transfer lines, columns and differential refractometer (the DRI detector) were contained in an oven maintained at 135° C.

Solvent for the SEC experiment was prepared by dissolving 6 grams of butylated hydroxy toluene as an antioxidant in 4 liters of Aldrich reagent grade 1,2,4 trichlorobenzene (TCB). The TCB mixture was then filtered through a 0.7 μm glass pre-filter and subsequently through a 0.1 μm Teflon filter. The TCB was then degassed with an online degasser before entering the SEC.

Polymer solutions were prepared by placing dry polymer in a glass container, adding the desired amount of TCB, then heating the mixture at 160° C. with continuous agitation for about 2 hours. All quantities were measured gravimetrically. The TCB densities used to express the polymer concentration in mass/volume units are 1.463 g/ml at room temperature and 1.324 g/ml at 135° C. The injection concentration ranged from 1.0 to 2.0 mg/ml, with lower concentrations being used for higher molecular weight samples.

Prior to running each sample the DRI detector and the injector were purged. Flow rate in the apparatus was then increased to 0.5 ml/minute, and the DRI was allowed to stabilize for 8-9 hours before injecting the first sample. The LS laser was turned on 1 to 1.5 hours before running samples.

The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the same as described below for the LS analysis. Units on parameters throughout this description of the SEC method are such that concentration is expressed in g/cm$^3$, molecular weight is expressed in g/mole, and intrinsic viscosity is expressed in dL/g.

The light scattering detector used was a Wyatt Technology High Temperature mini-DAWN. The polymer molecular weight, M, at each point in the chromatogram is determined by analyzing the LS output using the Zimm model for static light scattering (M. B. Huglin, LIGHT SCATTERING FROM POLYMER SOLUTIONS, Academic Press, 1971):

$$\frac{K_o c}{\Delta R(\theta)} = \frac{1}{MP(\theta)} + 2A_c c$$

Here, $\Delta R(\theta)$ is the measured excess Rayleigh scattering intensity at scattering angle $\theta$, c is the polymer concentration determined from the DRI analysis, $A_2$ is the second virial coefficient, $P(\theta)$ is the form factor for a monodisperse random coil (described in the above reference), and $K_o$ is the optical constant for the system:

$$K_o = \frac{4\pi^2 n^2 (dn/dc)^2}{\lambda^4 N_A}$$

in which $N_A$ is Avogadro's number, and (dn/dc) is the refractive index increment for the system. The refractive index, n=1.500 for TCB at 135° C. and $\lambda$=690 nm. In addition, $A_2$=0.0006 for propylene polymers and 0.0015 for butene polymers, and (dn/dc)=0.104 for propylene polymers and 0.098 for butene polymers.

A high temperature Viscotek Corporation viscometer was used, which has four capillaries arranged in a Wheatstone bridge configuration with two pressure transducers. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, $[\eta]$, at each point in the chromatogram is calculated from the following equation:

$$\eta_s = c[\eta] + 0.3(c[\eta])^2$$

where c was determined from the DRI output.

The branching index (g') is calculated using the output of the SEC-DRI-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromotographic slices, i, between the integration limits. The branching index g' is defined as:

$$g' = \frac{[\eta]_{avg}}{k M_v^\alpha}$$

where k=0.0002288 and $\alpha$=0.705 for propylene polymers, and k=0.00018 and $\alpha$=0.7 for butene polymers. $M_v$ is the viscosity-average molecular weight based on molecular weights determined by LS analysis.

$^{13}$C-NMR Spectroscopy

Polymer microstructure was determined by $^{13}$C-NMR spectroscopy, including the concentration of isotactic and syndiotactic diads ([m] and [r]), triads ([mm] and [rr]), and pentads ([mmmm] and [rrrr]). Samples were dissolved in d$_2$-1,1,2,2-tetrachloroethane. Spectra were recorded at 125° C. using a NMR spectrometer of 75 or 100 MHz. Polymer resonance peaks are referenced to mmmm=21.8 ppm. Calculations involved in the characterization of polymers by NMR follow the work of F. A. Bovey in "Polymer Conformation and Configuration" Academic Press, New York 1969 and J. Randall in "Polymer Sequence Determination, $^{13}$C-NMR Method", Academic Press, New York, 1977. The percent of methylene sequences of two in length, %(CH$_2$)$_2$, were calculated as follows: the integral of the methyl carbons between 14-18 ppm (which are equivalent in concentration to the number of methylenes in sequences of two in length) divided by the sum of the integral of the methylene sequences of one in length between 45-49 ppm and the integral of the methyl carbons between 14-18 ppm, times 100. This is a minimum calculation for the amount of methylene groups contained in a sequence of two or more since methylene sequences of greater than two have been excluded. Assignments were based on H. N. Cheng and J. A. Ewen, Makromol. Chem. 1989, 190, 1931.

Viscosity of Polymers and Blends

The shear viscosity as a function of shear rate was determined using a dual-barrel capillary rheometer. The capillary rheometer (Rosand Model RAH7/2 by Bohun Instruments) was equipped with a 30:1 length to diameter ratio capillary. A total mass of 25-30 g of pellets were packed into the capillary barrels and preheated at 230° C. for 10 minutes to remove any entrained air before the test. Each test was performed at 230° C. over the shear rate range of from 30 to 3000 s$^{-1}$. Corrections to the data for entrance pressure losses (i.e., the Bagley correction) were performed on-line via simultaneous pressure loss measurements for the flow of the material through an orifice that was installed into the second barrel of the rheometer.

The dynamic shear viscosity as a function of frequency was determined by small-amplitude oscillatory shear rheology. A Rheometrics Scientific DSR-500 dynamic stress-controlled rheometer with a cone and plate sample fixture was used. Testing was performed at 190° C. Samples were subjected to an oscillatory shear stress at a nominal amplitude of 100 Pa by oscillating the upper cone at a fixed frequency, and the resultant strain was measured. The auto-stress adjustment capability was utilized to keep the strain within limits of 1-30% (stress adjustment setting=32% of current stress, maximum stress=100 Pa). These conditions ensure that each material was characterized within its linear viscoelastic region. The dynamic shear viscosity was calculated from the measured strain and applied stress as a function of frequency. Frequency sweeps were conducted starting at 500 rad/s and decreasing to 0.02 rad/s, using a logarithmic sweep mode with 6 points per decade.

The dynamic shear viscosity ($\eta^*$) versus frequency ($\omega$) curves were fitted using the Cross model (as described in C. W. Macoskco, "Rheology: Principles, Measurements, and Applications", Wiley-VCH, 1994):

$$\eta^* = \frac{\eta_0}{1 + (\lambda\omega)^{1-n}}$$

The three parameters in this model are: $\eta_0$, the zero-shear viscosity; $\lambda$, the average relaxation time; and n, the power law exponent. The zero-shear viscosity is the value at a plateau in the Newtonian region of the flow curve at a low frequency, where the dynamic shear viscosity is independent of frequency. The average relaxation time corresponds to the inverse of the frequency at which shear-thinning starts. The power law exponent n is the slope of the shear thinning region at high shear rates in a log-log plot of dynamic shear viscosity versus frequency. These parameters provide a means to compare the effect of plasticization on a material's flow behavior, sensitivity to shear, and molecular structure.

Melt Flow Rate

Melt Flow Rate (MFR) is measured according to ASTM D1238 at 230° C. under a load of 2.16 kg unless otherwise noted. Melt Index (MI) is measured according to ASTM D 1238 at 190° C. under a load of 2.16 kg. The units for MFR and MI are g/10 min, or dg/min.

Polymer Density

Density is measured by density-gradient column, such as described in ASTM D1505, on a compression-molded specimen that has been slowly cooled to room temperature.

Dynamic Mechanical Thermal Analysis

The glass transition temperature ($T_g$) and storage modulus (E') were measured using dynamic mechanical thermal analysis (DMTA). This test provides information about the small-strain mechanical response (relaxation behavior) of a sample as a function of temperature over a temperature range that includes the glass transition region and the visco-elastic region prior to melting.

Typically, samples were tested using a three point bending configuration (TA Instruments DMA 2980). A solid rectangular compression molded bar was placed on two fixed supports; a movable clamp applied a periodic deformation to the sample midpoint at a frequency of 1 Hz and an amplitude of 20 μm. The sample was initially cooled to −130° C. then heated to 60° C. at a heating rate of 3° C./min. In some cases, compression molded bars were tested using other deformation configurations, namely dual cantilever bending and tensile elongation (Rheometrics RSAII). The periodic deformation under these configurations was applied at a frequency of 1 Hz and strain amplitude of 0.05%. The sample was cooled to −130° C. and then heated to 60° C. at a rate of 2° C./min. The slightly difference in heating rate does not influence the glass transition temperature measurements significantly.

The output of these DMTA experiments is the storage modulus (E') and loss modulus (E"). The storage modulus measures the elastic response or the ability of the material to store energy, and the loss modulus measures the viscous response or the ability of the material to dissipate energy. Tanδ is the ratio of E"/E' and gives a measure of the damping ability of the material. The beginning of the broad glass transition (β-relaxation) is identified as the extrapolated tangent to the Tanδ peak. In addition, the peak temperature and area under the peak are also measured to more fully characterize the transition from glassy to visco-elastic region.

Differential Scanning Calorimetry

Crystallization temperature ($T_c$) and melting temperature ($T_m$) were measured using Differential Scanning Calorimetry (DSC). This analysis was conducted using either a TA Instruments MDSC 2920 or a Perkin Elmer DSC7. Typically, 6 to 10 mg of molded polymer or plasticized polymer was sealed in an aluminum pan and loaded into the instrument at room temperature. Melting data (first heat) were acquired by heating the sample to at least 30° C. above its melting temperature at a heating rate of 10° C./min. This provides information on the melting behavior under as-molded conditions, which can be influenced by thermal history as well as any molded-in orientation or stresses. The sample was then held for 10 minutes at this temperature to destroy its thermal history. Crystallization data was acquired by cooling the sample from the melt to at least 50° C. below the crystallization temperature at a cooling rate of 10° C./min. The sample was then held at 25° C. for 10 minutes, and finally heated at 10° C./min to acquire additional melting data (second heat). This provides information about the melting behavior after a controlled thermal history and free from potential molded-in orientation and stress effects. The endothermic melting transition (first and second heat) and exothermic crystallization transition were analyzed for onset of transition and peak temperature. The melting temperatures reported in the tables are the peak melting temperatures from the second heat unless otherwise indicated. For polymers displaying multiple peaks, the higher melting peak temperature is reported.

Areas under the curve was used to determine the heat of fusion ($\Delta H_f$) which can be used to calculate the degree of crystallinity. A value of 207 J/g was used as the equilibrium heat of fusion for 100% crystalline polypropylene (obtained from B. Wunderlich, "Thermal Analysis", Academic Press, Page 418, 1990). The percent crystallinity is calculated using the formula, [area under the curve (J/g)/207 (J/g)]*100.

Size-Exclusion Chromatography of Polymers

Molecular weight distribution was characterized using Size-Exclusion Chromatography (SEC). Molecular weight (weight-average molecular weight, Mw, and number-average molecular weight, Mn) were determined using a High Temperature Size Exclusion Chromatograph (either from Waters Corporation or Polymer Laboratories), equipped with a differential refractive index detector (DRI), an online light scattering detector, and a viscometer. Experimental details not described below, including how the detectors were calibrated, are described in: T. Sun, P. Brant, R. R. Chance, and W. W. Graessley, Macromolecules, Volume 34, Number 19, 6812-6820, (2001).

Three Polymer Laboratories PLgel 10 mm Mixed-B columns were used. The nominal flow rate was 0.5 cm$^3$/min, and the nominal injection volume was 300 μL. The various transfer lines, columns and differential refractometer (the DRI detector) were contained in an oven maintained at 135° C.

Solvent for the SEC experiment was prepared by dissolving 6 grams of butylated hydroxy toluene as an antioxidant in 4 liters of Aldrich reagent grade 1,2,4 trichlorobenzene (TCB). The TCB mixture was then filtered through a 0.7 μm glass pre-filter and subsequently through a 0.1 μm Teflon filter. The TCB was then degassed with an online degasser before entering the SEC.

Polymer solutions were prepared by placing dry polymer in a glass container, adding the desired amount of TCB, then heating the mixture at 160° C. with continuous agitation for about 2 hours. All quantities were measured gravimetrically. The TCB densities used to express the polymer concentration in mass/volume units are 1.463 g/ml at room temperature and 1.324 g/ml at 135° C. The injection concentration ranged from 1.0 to 2.0 mg/ml, with lower concentrations being used for higher molecular weight samples.

Prior to running each sample the DRI detector and the injector were purged. Flow rate in the apparatus was then increased to 0.5 ml/minute, and the DRI was allowed to stabilize for 8-9 hours before injecting the first sample. The LS laser was turned on 1 to 1.5 hours before running samples.

The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the same as described below for the LS analysis. Units on parameters throughout this description of the SEC method are such that concentration is expressed in g/cm$^3$, molecular weight is expressed in g/mole, and intrinsic viscosity is expressed in dL/g.

The light scattering detector used was a Wyatt Technology High Temperature mini-DAWN. The polymer molecular weight, M, at each point in the chromatogram is determined by analyzing the LS output using the Zimm model for static light scattering (M. B. Huglin, LIGHT SCATTERING FROM POLYMER SOLUTIONS, Academic Press, 1971):

$$\frac{K_o c}{\Delta R(\theta)} = \frac{1}{M P(\theta)} + 2 A_c c$$

Here, $\Delta R(\theta)$ is the measured excess Rayleigh scattering intensity at scattering angle θ, c is the polymer concentration determined from the DRI analysis, $A_2$ is the second virial coefficient, $P(\theta)$ is the form factor for a monodisperse random coil (described in the above reference), and $K_o$ is the optical constant for the system:

$$K_o = \frac{4\pi^2 n^2 (dn/dc)^2}{\lambda^4 N_A}$$

in which $N_A$ is Avogadro's number, and (dn/dc) is the refractive index increment for the system. The refractive index, n=1.500 for TCB at 135° C. and λ=690 nm. In addition, $A_2$=0.0006 for propylene polymers and 0.0015 for butene polymers, and (dn/dc)=0.104 for propylene polymers and 0.098 for butene polymers.

A high temperature Viscotek Corporation viscometer was used, which has four capillaries arranged in a Wheatstone bridge configuration with two pressure transducers. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, [η], at each point in the chromatogram is calculated from the following equation:

$$\eta_s = c[\eta] + 0.3(c[\eta])^2$$

where c was determined from the DRI output.

The branching index (g') is calculated using the output of the SEC-DRI-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromotographic slices, i, between the integration limits. The branching index g' is defined as:

$$g' = \frac{[\eta]_{avg}}{k M_v^\alpha}$$

where k=0.0002288 and α=0.705 for propylene polymers, and k=0.00018 and α=0.7 for butene polymers. $M_v$ is the viscosity-average molecular weight based on molecular weights determined by LS analysis.

$^{13}$C-NMR Spectroscopy

Polymer microstructure was determined by $^{13}$C-NMR spectroscopy, including the concentration of isotactic and syndiotactic diads ([m] and [r]), triads ([mm] and [rr]), and pentads ([mmmm] and [rrrr]). Samples were dissolved in d$_2$-1,1,2,2-tetrachloroethane. Spectra were recorded at 125° C. using a NMR spectrometer of 75 or 100 MHz. Polymer resonance peaks are referenced to mmmm=21.8 ppm. Calculations involved in the characterization of polymers by NMR follow the work of F. A. Bovey in "Polymer Conformation and Configuration" Academic Press, New York 1969 and J. Randall in "Polymer Sequence Determination, $^{13}$C-NMR Method", Academic Press, New York, 1977. The percent of methylene sequences of two in length, %(CH$_2$)$_2$, were calculated as follows: the integral of the methyl carbons between 14-18 ppm (which are equivalent in concentration to the number of methylenes in sequences of two in length) divided by the sum of the integral of the methylene sequences of one in length between 45-49 ppm and the integral of the methyl carbons between 14-18 ppm, times 100. This is a minimum calculation for the amount of methylene groups contained in a sequence of two or more since methylene sequences of greater than two have been excluded. Assignments were based on H. N. Cheng and J. A. Ewen, Makromol. Chem. 1989, 190, 1931.

Viscosity of Polymers and Blends

The shear viscosity as a function of shear rate was determined using a dual-barrel capillary rheometer. The capillary rheometer (Rosand Model RAH7/2 by Bohun Instruments) was equipped with a 30:1 length to diameter ratio capillary. A total mass of 25-30 g of pellets were packed into the capillary barrels and preheated at 230° C. for 10 minutes to remove any entrained air before the test. Each test was performed at 230° C. over the shear rate range of from 30 to 3000 s$^{-1}$. Corrections to the data for entrance pressure losses (i.e., the Bagley correction) were performed on-line via simultaneous pressure loss measurements for the flow of the material through an orifice that was installed into the second barrel of the rheometer.

The dynamic shear viscosity as a function of frequency was determined by small-amplitude oscillatory shear rheology. A Rheometrics Scientific DSR-500 dynamic stress-controlled rheometer with a cone and plate sample fixture was used. Testing was performed at 190° C. Samples were subjected to an oscillatory shear stress at a nominal amplitude of 100 Pa by oscillating the upper cone at a fixed frequency, and the resultant strain was measured. The auto-stress adjustment capability was utilized to keep the strain within limits of 1-30% (stress adjustment setting=32% of current stress, maximum stress=100 Pa). These conditions ensure that each material was characterized within its linear viscoelastic region. The dynamic shear viscosity was calculated from the measured strain and applied stress as a function of frequency. Frequency sweeps were conducted starting at 500 rad/s and decreasing to 0.02 rad/s, using a logarithmic sweep mode with 6 points per decade.

The dynamic shear viscosity ($\eta^*$) versus frequency ($\omega$) curves were fitted using the Cross model (as described in C. W. Macoskco, "Rheology: Principles, Measurements, and Applications", Wiley-VCH, 1994):

$$\eta^* = \frac{\eta_0}{1 + (\lambda\omega)^{1-n}}$$

The three parameters in this model are: $\eta_0$, the zero-shear viscosity; $\lambda$, the average relaxation time; and n, the power law exponent. The zero-shear viscosity is the value at a plateau in the Newtonian region of the flow curve at a low frequency, where the dynamic shear viscosity is independent of frequency. The average relaxation time corresponds to the inverse of the frequency at which shear-thinning starts. The power law exponent n is the slope of the shear thinning region at high shear rates in a log-log plot of dynamic shear viscosity versus frequency. These parameters provide a means to compare the effect of plasticization on a material's flow behavior, sensitivity to shear, and molecular structure.

Melt Flow Rate

Melt Flow Rate (MFR) is measured according to ASTM D1238 at 230° C. under a load of 2.16 kg unless otherwise noted. Melt Index (MI) is measured according to ASTM D 1238 at 190° C. under a load of 2.16 kg. The units for MFR and MI are g/10 min, or dg/min.

Polymer Density

Density is measured by density-gradient column, such as described in ASTM D1505, on a compression-molded specimen that has been slowly cooled to room temperature.

Mechanical Properties

Test specimens for mechanical property testing were injection-molded, unless otherwise specified. The testing temperature was standard laboratory temperature (23±2° C.) as specified in ASTM D618, unless otherwise specified. Instron load frames were used for tensile and flexure testing.

Tensile properties were determined according to ASTM D638, including Young's modulus (also called modulus of elasticity), yield stress (also called tensile strength at yield), yield strain (also called elongation at yield), break stress (also called tensile strength at break), and break strain (also called elongation at break). The energy to yield is defined as the area under the stress-strain curve from zero strain to the yield strain. The energy to break is defined as the area under the stress-strain from zero strain to the break strain. Injection-molded tensile bars were of either ASTM D638 Type I or Type IV geometry, tested at a speed of 2 inch/min. Compression-molded tensile bars were of ASTM D412 Type C geometry, tested at a speed of 20 inch/min. For compression-molded specimens only: the yield stress and yield strain were determined as the 10% offset values as defined in ASTM D638. Break properties were reported only if a majority of test specimens broke before a strain of about 2000%, which is the maximum strain possible on the load frame used for testing.

Flexure properties were determined according to ASTM D790A, including the 1% secant modulus and 2% secant modulus. In some cases, test specimen geometry was as specified under the ASTM D790 section "Molding Materials (Thermoplastics and Thermosets)", and the support span was 2 inches.

Heat deflection temperature was determined according to ASTM D648, at 66 psi, on injection-molded specimens.

Rockwell hardness was determined according to ASTM D785, using the R-scale.

Impact Properties

Gardner impact strength was determined according to ASTM D5420, on 3.5 inch diameter X 0.125 inch thick injection-molded disks, at the specified temperature.

Notched izod impact resistance was determined according to ASTM D256, at the specified temperature. A TMI Izod Impact Tester was used. Specimens were either cut individually from the center portion of injection-molded ASTM D638 Type I tensile bars, or pairs of specimens were made by cutting injection-molded flexure bars in half, where the flexure bar geometry was as specified in the ASTM D790 section "Molding Materials (Thermoplastics and Thermosets)". The notch was oriented such that the impact occurred on the notched side of the specimen (following Procedure A of ASTM D256) in most cases; where specified, the notch orientation was reversed (following Procedure E of ASTM D256) and referred to as "Reverse Notched Izod" (RNI) or "Unnotched Izod" (UNI) impact. All specimens were assigned a thickness of 0.122 inch for calculation of the impact resistance. All breaks were complete, unless specified otherwise.

Optical Properties

Haze was determined by ASTM D1003, on a 0.04 inch think injection-molded plaque. Gloss was determined by ASTM D2457, at an angle of 45°.

Fabric and Film Properties

Flexure and tensile properties (including 1% Secant Flexure Modulus, Peak Load, Tensile Strength at Break, and Elongation at Break) are determined by ASTM D 882. Elmendorf tear is determined by ASTM D 1922. Puncture and puncture energy are determined by ASTM D 3420. Total energy dart impact is determined by ASTM D 4272

Softness or "hand" of spunbond nonwoven fabric as it is known in the art was measured using the Thwing-Albert Handle-O-Meter (Model 211-10-B/America.) The quality of "hand" is considered to be the combination of resistance due to the surface friction and flexibility of a fabric material. The Handle-O-Meter measures the above two factors using and LVDT (Linear Variable Differential Transformer) to detect the resistance that a blade encounters when forcing a specimen of material into a slot of parallel edges. A 3½ digit digital voltmeter (DVM) indicates the resistance directly in grams. The "total hand" of any given sheet of material is the average of four readings taken on both sides and both directions of a test sample and is recorded in grams per standard width of sample material. A decrease in "total hand" indicates the improvement of fabric softness.

Fluid Properties

Pour Point is measured by ASTM D 97. Kinematic Viscosity (KV) is measured by ASTM D 445. Specific gravity is typically determined by ASTM D 4052, at the temperature specified. Viscosity index (VI) is determined by ASTM D 2270. Boiling point and distillation range are typically determined by ASTM D 86 or ASTM D 1160. Saturates and aromatics content can be determined by various methods, such as ASTM D 3238.

The number-average molecular weight (Mn) can be determined by Gas Chromatography (GC), as described in "Modern Practice of Gas Chromatography", R. L. Grob and E. F. Barry, Wiley-Interscience, 3rd Edition (July 1995); or determined by Gel Permeation Chromatography (GPC), as described in "Modern Size Exclusion Liquid Chromatographs", W. W. Yan, J. J. Kirkland, and D. D. Bly, J. Wiley & Sons (1979); or estimated by ASTM D 2502; or estimated by freezing point depression, as described in "Lange's Handbook of Chemistry", 15th Edition, McGrawHill. The average carbon number (Cn) is calculated from Mn by $Cn=(Mn-2)/14$.

Processing Methods

Blending

The components of the present invention can be blended by any suitable means. For example, they may be blended in a static mixer, batch mixer, extruder, or a combination thereof, that is sufficient to achieve an adequate dispersion of plasticizer in the polymer. The mixing step may involve first dry blending using, for example, a tumble blender. It may also involve a "master batch" approach, where the final plasticizer concentration is achieved by combining neat polymer with an appropriate amount of plasticized polymer that had been previously prepared at a higher plasticizer concentration. Dispersion may take place as part of a processing method used to fabricate articles, such as in the extruder on an injection molding maching or fiber line. The plasticizer may be injected into the extruder barrel or introduced at the feed throat of the extruder to save the step of preblending. This is a preferred method when a larger percentage of plasticizer is to be used or large quantities of plasticized resin are desired.

Two general methods were used to generate examples of plasticized blends. The first method, which is referred to as the Extruder Method, involved first "dry blending" reactor granules of the polymer with appropriate amounts of plasticizer and an additive package (including such components as antioxidants and nucleating agents) in a tumble blender to achieve a homogeneous mixing of components at the desired plasticizer and additive concentrations. This was followed by compounding and pelletizing the blend using an extruder (either a 30 or 57 mm twin screw extruder) at an appropriate extrusion temperature above the melting point of the polymer, but always in the range of 200-230° C. In some cases, a sample of desired plasticizer concentration was produced by adding neat polymer pellets to plasticized polymer pellets that had been blended previously at a higher plasticizer concentration.

The second method, which is referred to as the Brabender Method, involved mixing polymer pellets with the plasticizer in a heated C. W. Brabender Instruments Plasticorder to achieve a homogeneous melt at the desired plasticizer concentration. The Brabender was equipped with a Prep-Mixer head (approximately 200 cm$^3$ volume) and roller blades. The operating temperature was above the melting point of the polymer, but always in the range of 180-190° C. Polymer was first melted in the Brabender for 1 minute at 60 RPM. Plasticizer was then added slowly to prevent pooling in the melted polymer. The blend was then mixed for 5 minutes at 60 RPM under a nitrogen purge. The Brabender was opened and the melt removed from the mixing head and blades as quickly as possible, and allowed to solidify. For those blends later subjected to injection molding, the pieces of material from the Brabender were cut into smaller pieces using a guillotine, then ground into even smaller pieces using a Wiley Mill.

Injection Molding

For materials blended using the Extruder Method, standard ASTM tensile and HDT bars, and Gardner impact discs, were molded using 120 ton injection molding equipment according to ASTM D4101. For materials blended using the Brabender Method, tensile and flexure bars were molded using 20 ton injection molding equipment according to ASTM D4101, except for the following provisions: the mold temperature was 40° C.; the inject time was 30 sec; the tensile and flex bars were of ASTM D638 Type IV and ASTM D790 geometries, respectively; and the melt temperature was, in some cases, 10° C. off from the ASTM D4101-specified value, but always in the range of 190-200° C. (except for the polybutene blends, which were molded with a melt temperature in the range of 220-230° C.).

Compression Molding

Material to be molded was placed between two sheets of PTFE-coated aluminum foil onto a 0.125 inch thick chase, and pressed in a Carver press at 160° C. The material was allowed to melt for 5 minutes without pressure applied, then compressed for 5 minutes at 10 tons pressure. It was then removed and immediately placed between water-cooled cold platens and pressed for another 5 minutes at 10 tons pressure. The foil-sample-foil assembly was allowed to anneal for at least 40 hours at room temperature, then quenched in dry ice prior to removing the sample from the foil to prevent deformation of the material when peeling off the foil. Tensile and flexure specimens were died out of the sample once it warmed to room temperature.

Spunbond Fabric Process

A typical spunbond process consists of a continuous filament extrusion, followed by drawing, web formation by the use of some type of ejector, and bonding the web. The polymer pellets are first fed into an extruder. In the extruder, the pellets simultaneously are melted and forced through the system by a heating melting screw. At the end of the screw, a spinning pump meters the molten polymer through a filter to a spinneret where the molten polymer is extruded under pressure through capillaries at a certain throughput rate (grams per hole per minute). The spinneret contains a few hundred capillaries, measuring 0.4 mm in diameter. The polymer is melted at about 30-50° C. above its melting point to achieve sufficiently low melt viscosity for extrusion. The fibers exiting the spinneret are quenched and drawn into fine fibers measuring about 16 microns in diameter. The solidified fiber is laid randomly on a moving belt to form a random netlike structure known in the art as web. Different basis weight (grams per square meter) of web is obtained by controlling the belt moving speed. After web formation, the web is bonded to achieve its final strength using a heated textile calender known in the art as thermobond calender. The calender consists of two heated steel rolls; one roll is plain and the other bears a pattern of raised points. The web is conveyed to the calender wherein a fabric is formed by pressing the web between the rolls at a bonding temperature of about 138° C.

Cast Film Process

Cast films were prepared using the following operations. Cast monolayer films were fabricated on a Killion cast film line. This line has three 24:1 L/D 2.54 cm diameter extruder, which feed polymer into a feedblock. The feedblock diverts molten polymer from the extruder to a 20.32 cm wide Cloeren die. Molten polymer exits the die at a temperature of 230° C. and is cast on a chill roll (20.3 cm diameter, 25.4 cm roll face) at 21° C. The casting unit is equipped with adjustable winding speeds to obtain film of the targeted thickness.

Methods for Determining NFP Content in Blend

Method 1: Extraction

One method to determine the amount of NFP in a blend is Soxhlet extraction, wherein at least a majority of the NFP is extracted with refluxing n-heptane. Analysis of the base polymer is also required because it may contain low molecular weight and/or amorphous material that is soluble in refluxing n-heptane. The level of plasticizer in the blend is determined by correcting its extractables level, in weight percent, by the extractables level for the base polymer, as described below.

The Soxhlet extraction apparatus consists of a 400 ml Soxhlet extractor, with a widened overflow tube (to prevent siphoning and to provide constant flow extraction); a metal screen cage fitted inside the main Soxhlet chamber; a Soxhlet extraction thimble (Whatman, single thickness, cellulose) placed inside the screen cage; a condenser with cooling water and drain; and a one-neck 1000 ml round bottom flask with appropriately sized stir bar and heating mantle.

The procedure is as follows. Dry the soxhlet thimbles in a 95° C. oven for ~60 minutes. Weigh the dry thimble directly after removal from oven; record this weight as A: Thimble Weight Before, in g. Weigh out 15-20 grams of sample (either in pellet or ground pellet form) into the thimble; record as B: Polymer Weight, in g. Place the thimble containing the polymer in the Soxhlet apparatus. Pour about 300 ml of HPLC-grade n-heptane into the round bottom flask with stir bar and secure the flask on the heating mantle. Connect the round bottom flask, the soxhlet, and the condenser in series. Pour more n-heptane down through the center of the condenser into the Soxhlet main chamber until the solvent level is just below the top of the overflow tube. Turn on the cooling water to the condenser. Turn on the heating mantle and adjust the setting to generate a rolling boil in the round bottom flask and maintain a good reflux. Allow to reflux for 16 hours. Turn the heat off but leave the cooling system on. Allow the system to cool down to room temperature. Disassemble the apparatus. Remove the thimble and rinse with a small amount of fresh n-heptane.

Allow to air dry in the laboratory hood, followed by oven drying at 95° C. for 90 minutes. Weigh the thimble containing the polymer directly after removal from oven; record as C: Polymer/Thimble Weight After, in g.

The quantity of extract is determined by calculating the weight loss from the sample, W=(A+B−C), in g. The extractables level, E, in weight percent, is then calculated by E=100(W/B). The plasticizer content in the blend, P, in weight percent, is calculated by P=E(blend)−E(base polymer).

Method 2: Crystallization Analysis Fractionation (CRYSTAF)

Another method to determine the amount of NFP in a blend is fractionation using the Crystallization Analysis Fractionation (CRYSTAF) technique. This technique involves dissolving a sample in a solvent at high temperature, then cooling the solution slowly to cause fractionation of the sample based on solubility. For semi-crystalline samples, including blends, solubility depends primarily on crystallizability: portions of the sample that are more crystalline will precipitate out of solution at a higher temperature than portions of the sample that are less crystalline. The relative amount of sample in solution as a function of temperature is measured using an infrared (IR) detector to obtain the cumulative solubility distribution. The soluble fraction (SF) is defined as the IR signal at the lowest temperature divided by the IR signal when all the sample is dissolved at high temperature, and corresponds to the weight fraction of sample that has not crystallized.

In the case of plasticized polyolefins, the plasticizer is mostly amorphous and therefore contributes to the SF. Thus, the SF will be larger for blends with higher plasticizer content. This relationship is exploited to determine the plasticizer content of a blend of known composition (polymer and plasticizer types) but unknown concentration. A calibration curve that describes the SF as a function of plasticizer content is developed by making a series of physical blends of known concentration using the same polymer and plasticizer materials, and then analyzing these blends under the same run conditions as used for blends of unknown concentration. This series of calibrants must include plasticizer concentrations above and below the concentration of the unknown sample(s), but not greater than 50 weight percent plasticizer, in order to reliably apply the calibration curve to the unknown sample(s). Typically, a linear fit of the calibration points is found to provide a good description of the SF as a function of plasticizer content ($R^2>0.9$); other functional forms with 2 or fewer fitting parameters may be used if they improve the goodness-of-fit (increase $R^2$).

A commercial CRYSTAF 200 instrument (Polymer Char S. A., Valencia, Spain) with five stirred stainless steel vessels of 60 mL volume was used to perform this test. Approximately 30 mg of sample were dissolved for 60 min at 160° C. in 30 mL of 1,2-dichlorobenzene that was stabilized with 2 g/4 L of butylated hydroxytoluene. The solution was then stabilized for 45 min at 100° C. The crystallization was carried out from 100 to 30° C. at a crystallization rate of 0.2° C./min. A dual wavelength infrared detector with a heated flow through cell maintained at 150° C. was used to measure the polymer concentration in solution at regular intervals during the crystallization cycle; the measuring wavelength was 3.5 μm and the reference wavelength was 3.6 μm.

EXAMPLES

The present invention, while not meant to be limiting by, may be better understood by reference to the following examples and tables. The polymers and fluids used in the examples are described in Tables 4 and 5.

Examples in Tables 6-14 Based on Blends Made Using the Extruder Method

Samples 1-9 in Tables 6 and 9 were blended using the Extruder Method; the additive package contained 600 ppm of Irganox 1076 and 260 ppm of calcium stearate; a 57 mm twin-screw extruder was used at an extrusion temperature of 230° C. Samples 10-14 in Tables 7 and 10 were blended using the Extruder Method; the additive package contained 825 ppm calcium stearate, 800 ppm of Ultranox 626, 500 ppm of Tinuvin 622, and 2500 ppm of Millad 3940; a 30 mm twin-screw extruder was used at an extrusion temperature of 216° C. Samples 15-19 in Tables 8 and 11 were blended using the Extruder Method; the additive package contained 800 ppm of calcium stearate, 1500 ppm of Irganox 1010, 500 ppm of Ultranox 626, and 675 ppm of sodium benzoate; a 30 mm twin-screw extruder was used at an extrusion temperature of 205° C. Samples 20-24 in Table 12 were made by dry blending neat polymer pellets with previously blended pellets of higher plasticizer concentration (Samples 6-9) to attain the desired plasticizer concentration.

Figure 11:
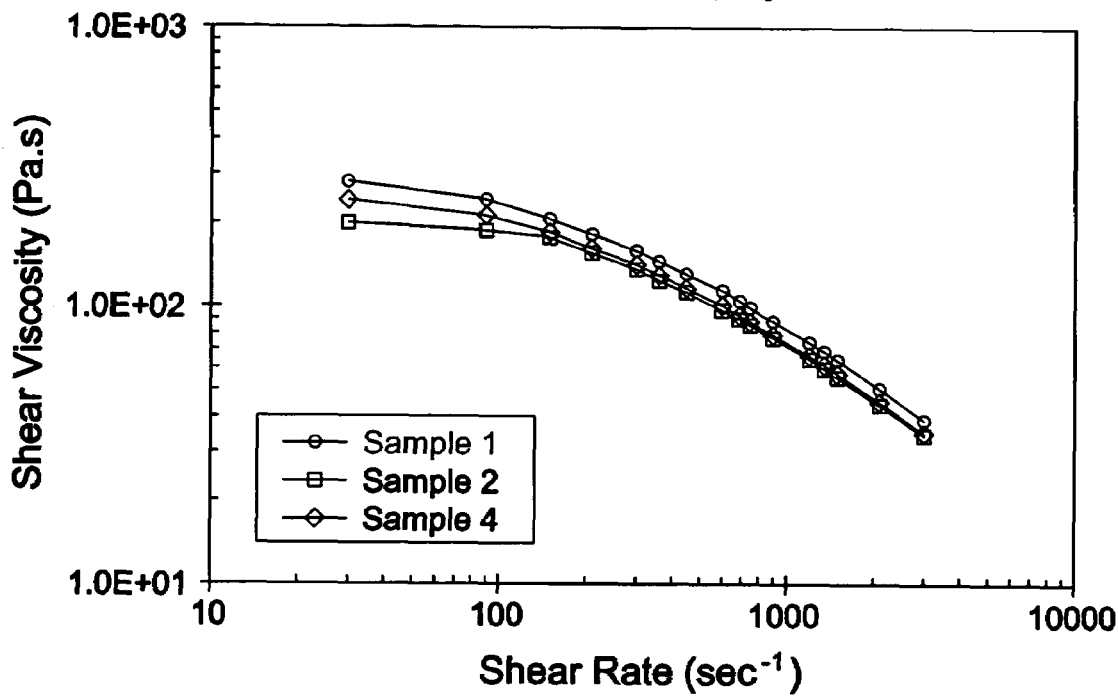
FIG. 11 is a graphical representation of the shear viscosity as a function of shear rate for various plasticized propylene homopolymer samples illustrative of the invention.
Figure 12:
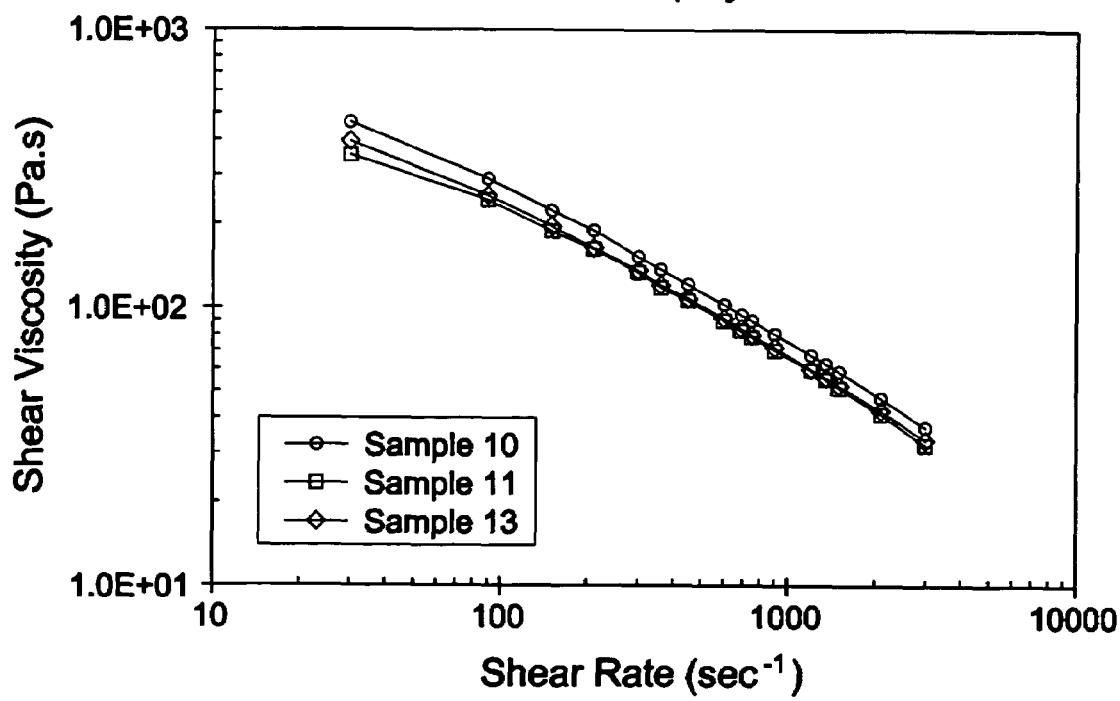
FIG. 12 is a graphical representation of the shear viscosity as a function of shear rate for various plasticized propylene copolymer samples illustrative of the invention.
Figure 13:
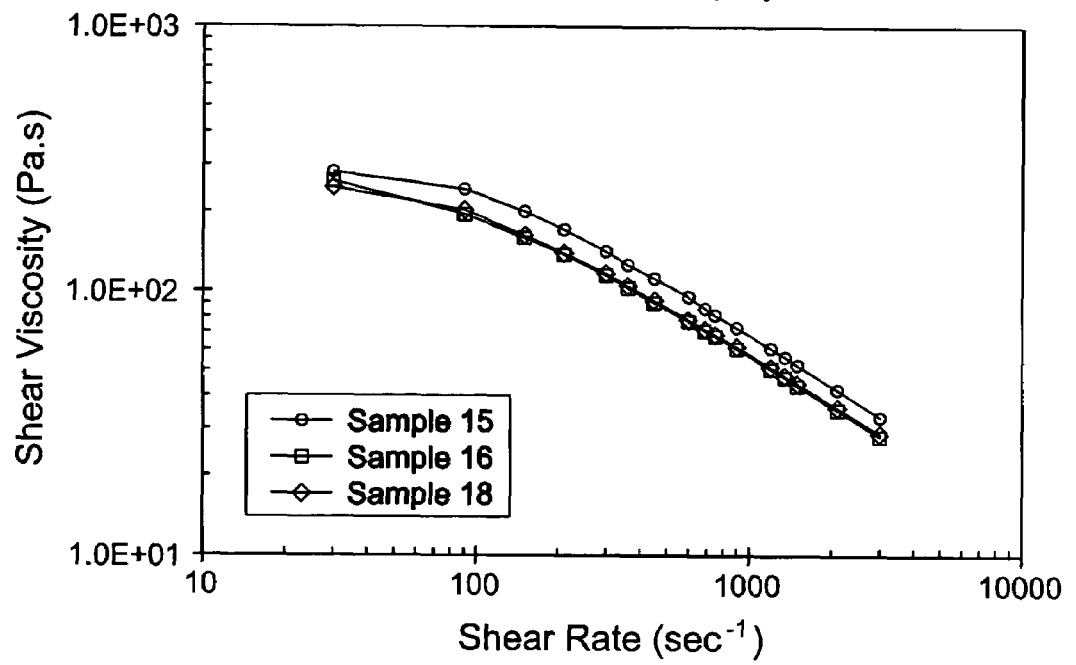
FIG. 13 is a graphical representation of the shear viscosity as a function of shear rate for various plasticized propylene impact copolymer samples illustrative of the invention.
Figure 14:
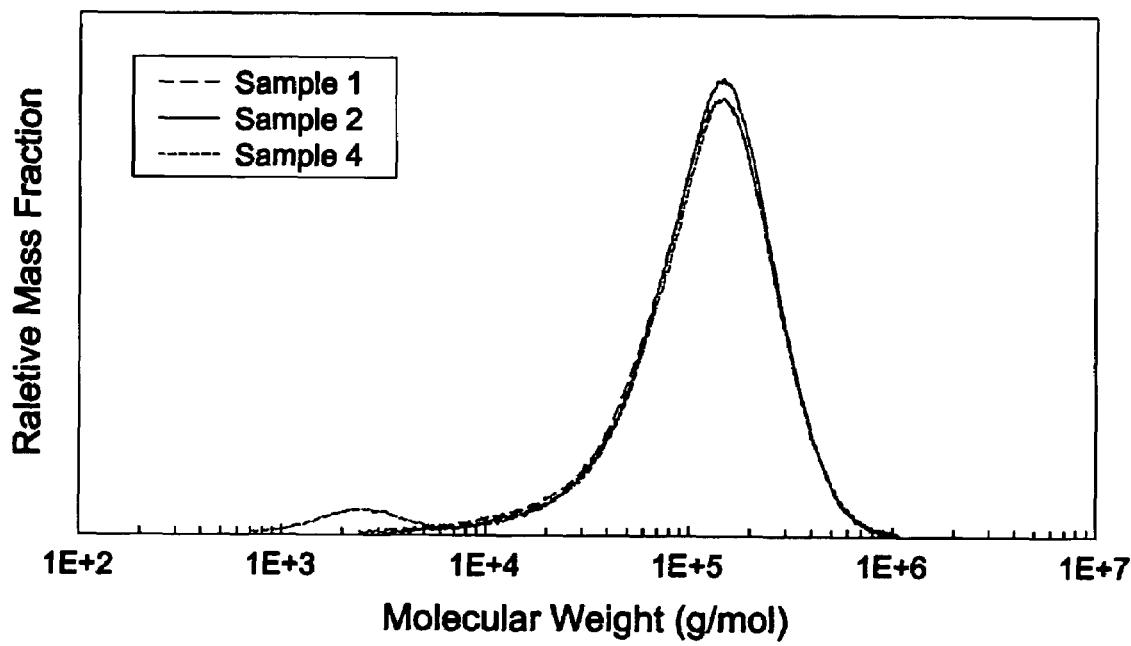
FIG. 14 is a graphical representation of the molecular weight distribution for various plasticized propylene homopolymer samples illustrative of the invention.

The resin properties of these samples are listed in Tables 6-8. The addition of NFP in the propylene polymers improve melt flowability, as indicated by the significant increase of melt flow rate. The improvement of melt flowability can be characterized by the decrease of shear viscosity as a function of shear rate range, as illustrated in FIGS. 11-13. In contrast to a peroxide degrading (or so called "vis-breaking") process, the increase of melt flowability in the current invention is mainly due to the plasticizing effect of the NFP; the polymer molecular weight is unchanged. This is evident in the comparison of molecular weight distribution, as shown in FIG. 14. The improvement of melt flowability usually benefits fabrication processes (for example, fiber spinning, film casting, extrusion, and injection molding) in terms of better draw-down, lower extruder torque, thin wall injection, and faster cycle time.

The NFP in the current invention provides a significant depression in the storage modulus of propylene polymers. As illustrated in FIG. 1, the storage modulus of plasticized propylene polymers are drastically reduced as a function of temperature relative to the unplasticized polyolefins. A propylene polymer having lower a storage modulus (or "elastic modulus") at any particular temperature indicates better flexibility for the end-use at that particular temperature.

The NFP in the current invention demonstrates the ability to depress $T_g$ without altering the melting temperature and crystallization temperature of propylene polymers, as illustrated in FIGS. 5-10. Traditional methods to depress $T_g$ include the incorporation of comonomers as in the case for the propylene copolymers, which also depresses the melting temperature and crystallization temperature of polymer. Polymers having lower $T_g$ without compromising the melting characteristics are very desirable and can provide better impact resistance, particularly for below freezing temperature impact resistance, while maintaining the ability for high temperature usage. The plasticized polyolefins of the present invention provide this.

Figure 2:
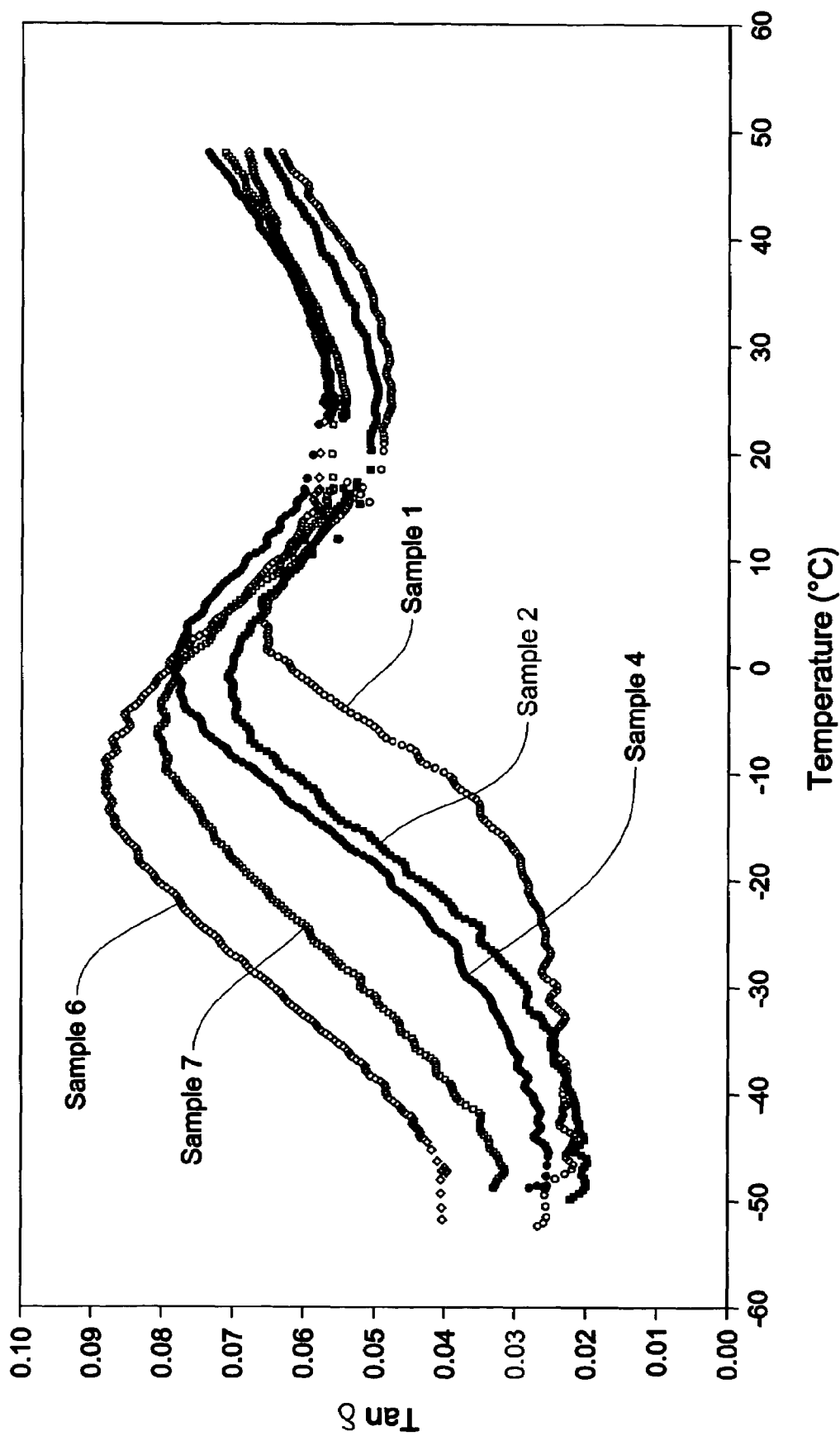
FIG. 2 is a graphical representation of the Tan δ as a function of temperature for various plasticized propylene homopolymer examples cited herein.
Figure 3:
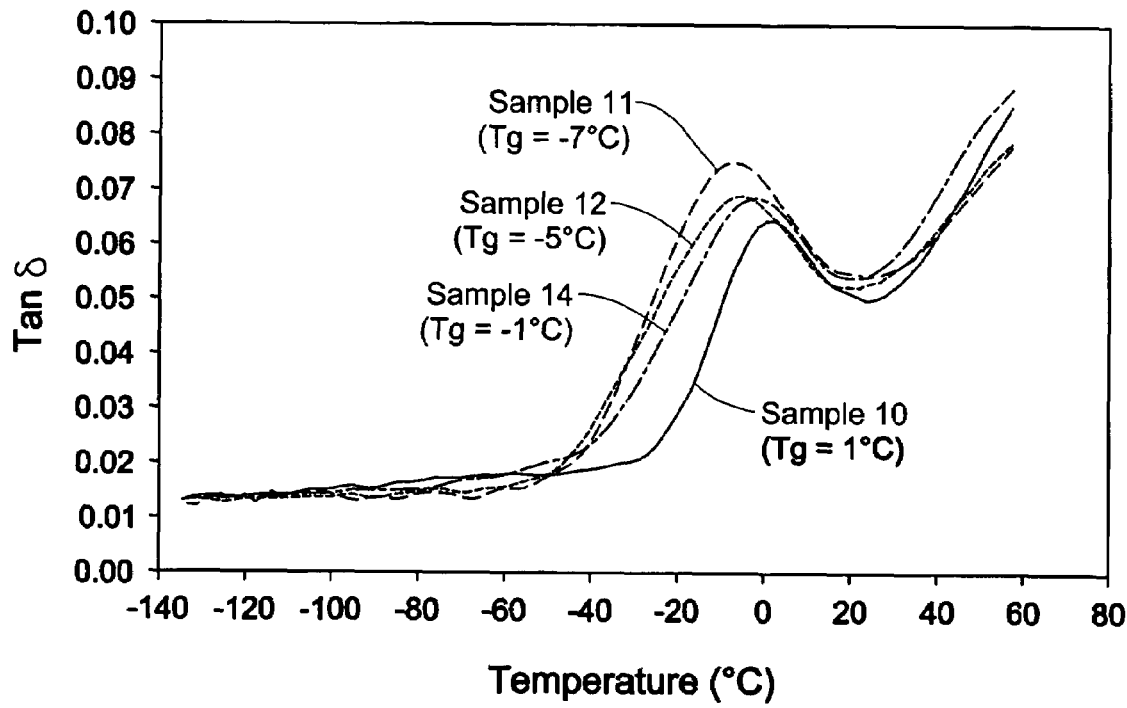
FIG. 3 is a graphical representation of the Tan δ as a function of temperature for various plasticized propylene copolymer examples cited herein.
Figure 4:
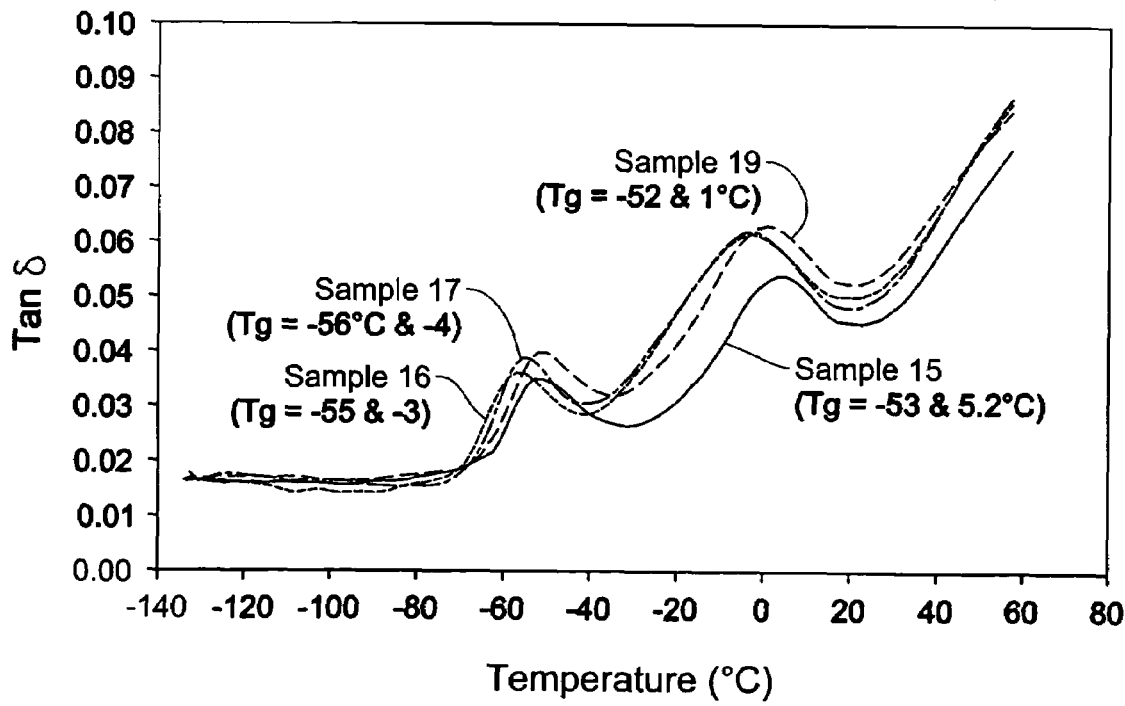
FIG. 4 is a graphical representation of the Tan δ as a function of temperature for various plasticized propylene impact copolymer examples cited herein.
Figure 5:
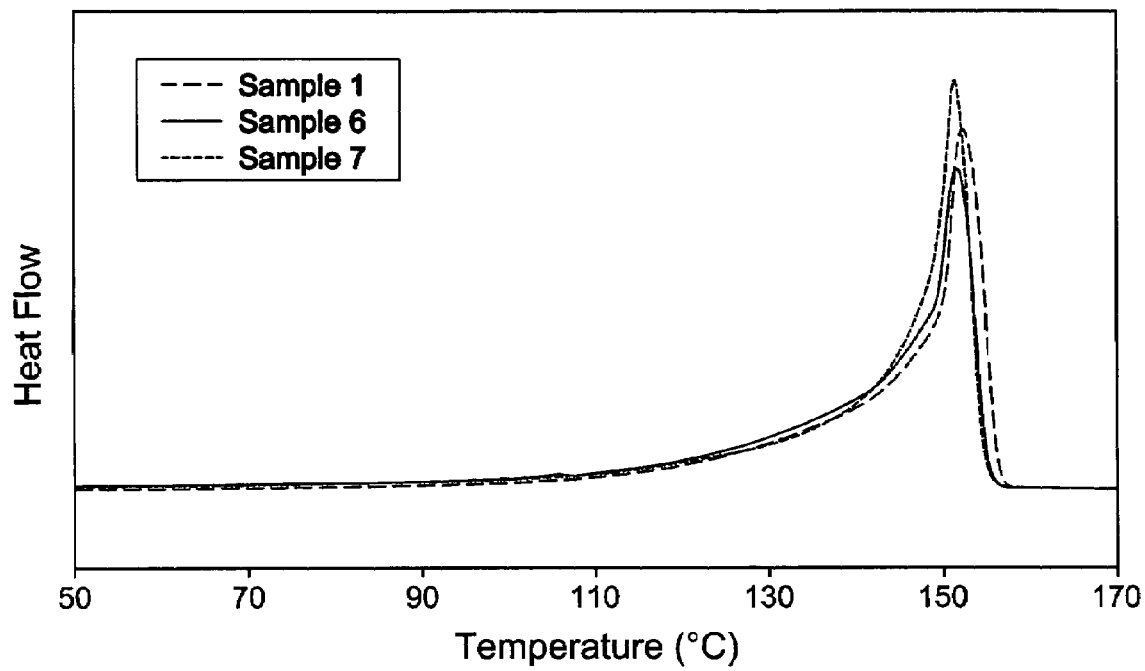
FIG. 5 is a graphical representation of the melting heat flow from DSC as a function of temperature for various plasticized propylene homopolymer samples illustrative of the invention.
Figure 6:
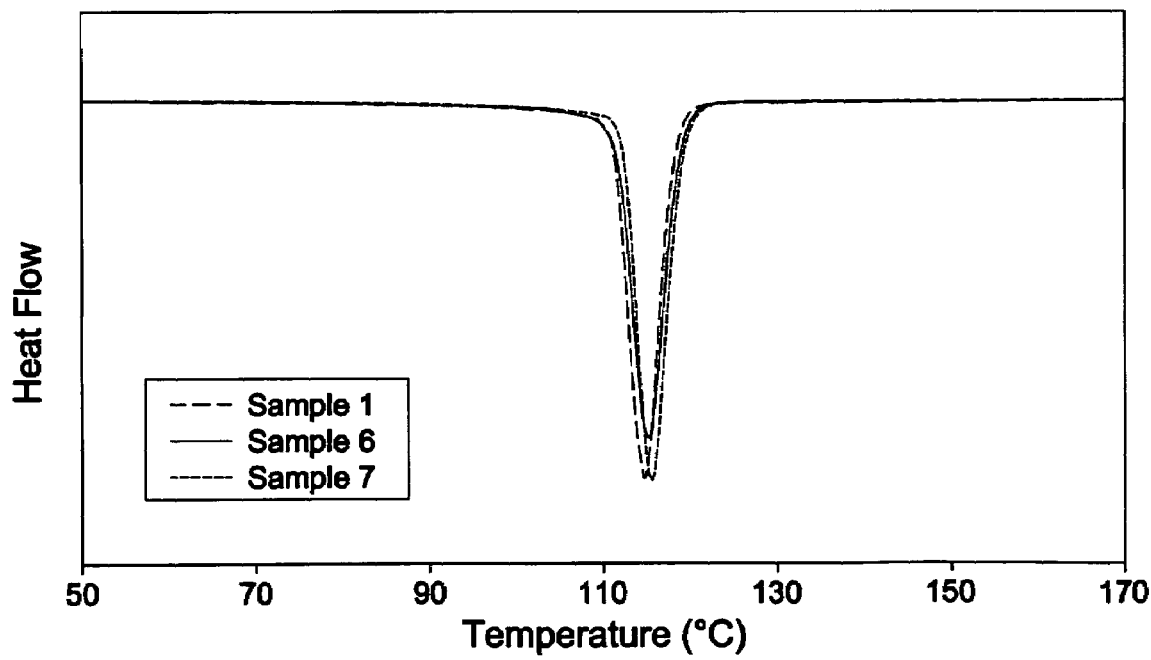
FIG. 6 is a graphical representation of the crystallization heat flow from DSC as a function of temperature for various samples plasticized propylene homopolymer samples illustrative of the invention.
Figure 7:
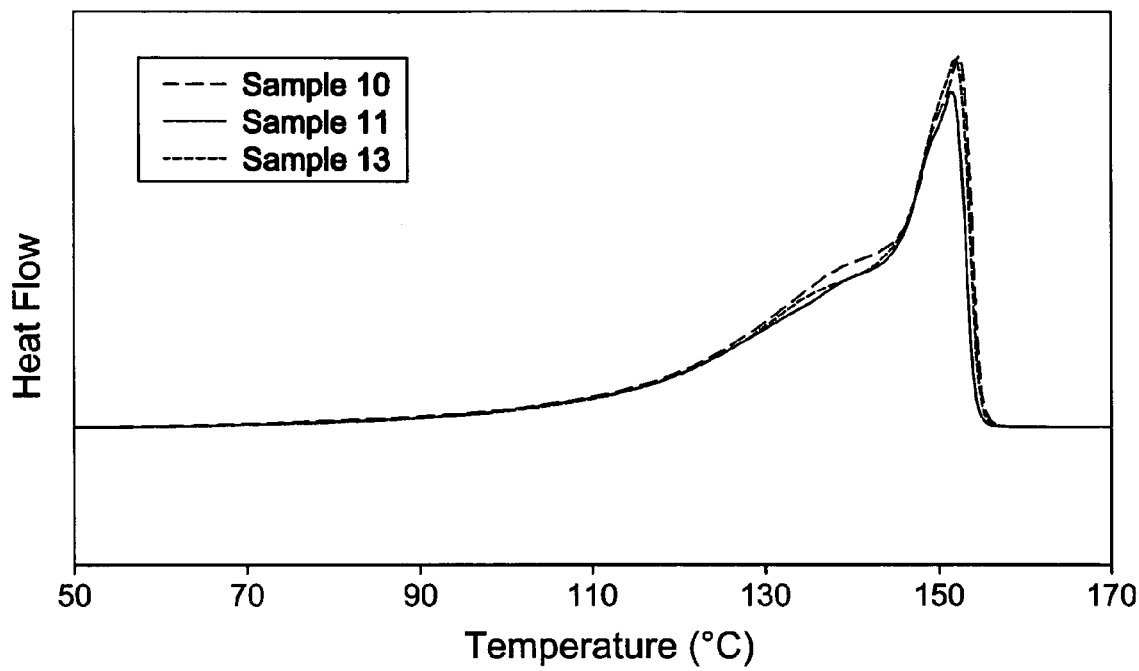
FIG. 7 is a graphical representation of the melting heat flow from DSC as a function of temperature for various plasticized propylene copolymer samples illustrative of the invention.
Figure 8:
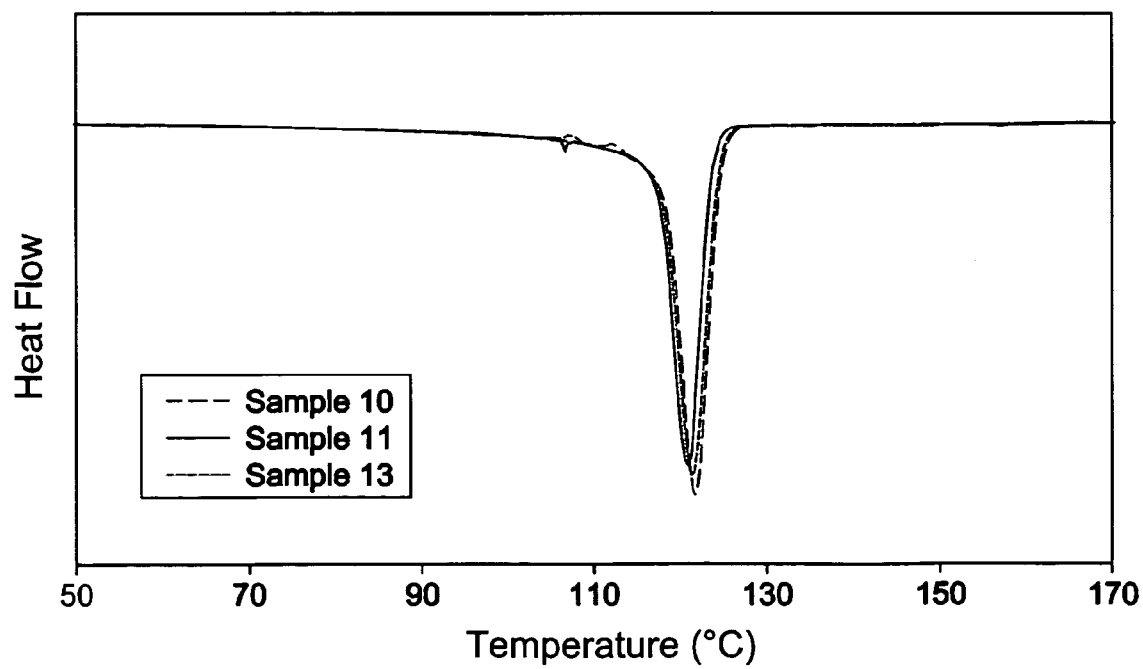
FIG. 8 is a graphical representation of the crystallization heat flow from DSC as a function of temperature for various plasticized propylene copolymer samples illustrative of the invention.
Figure 9:
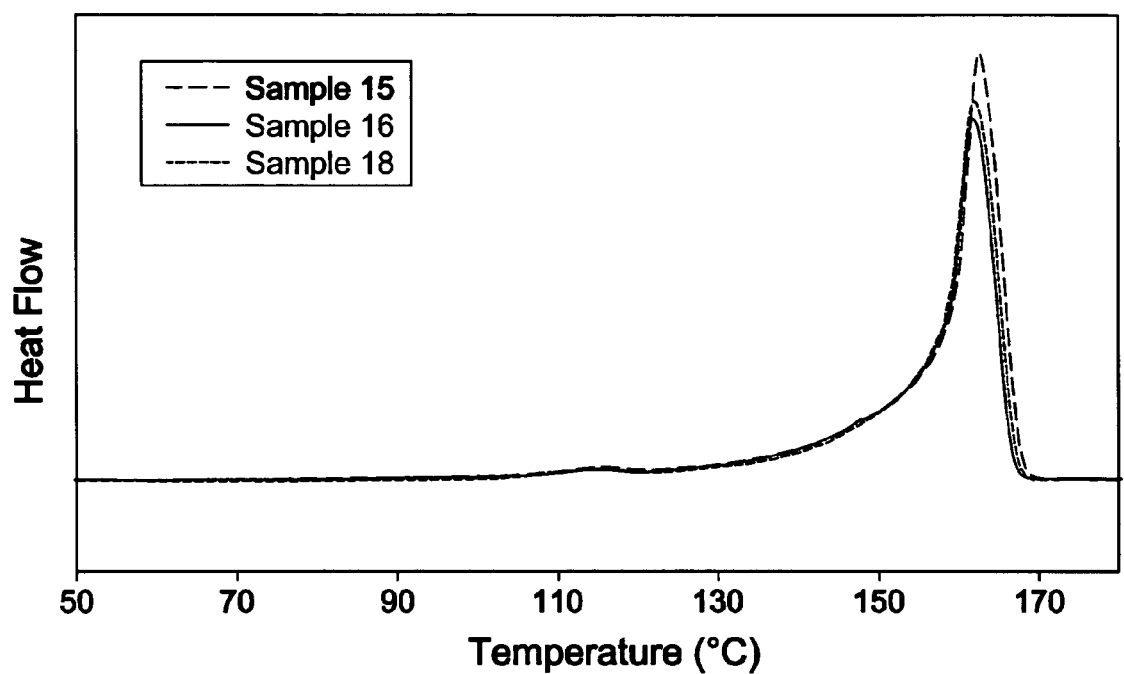
FIG. 9 is a graphical representation of the melting heat flow from DSC as a function of temperature for various plasticized propylene impact copolymer samples illustrative of the invention.
Figure 10:
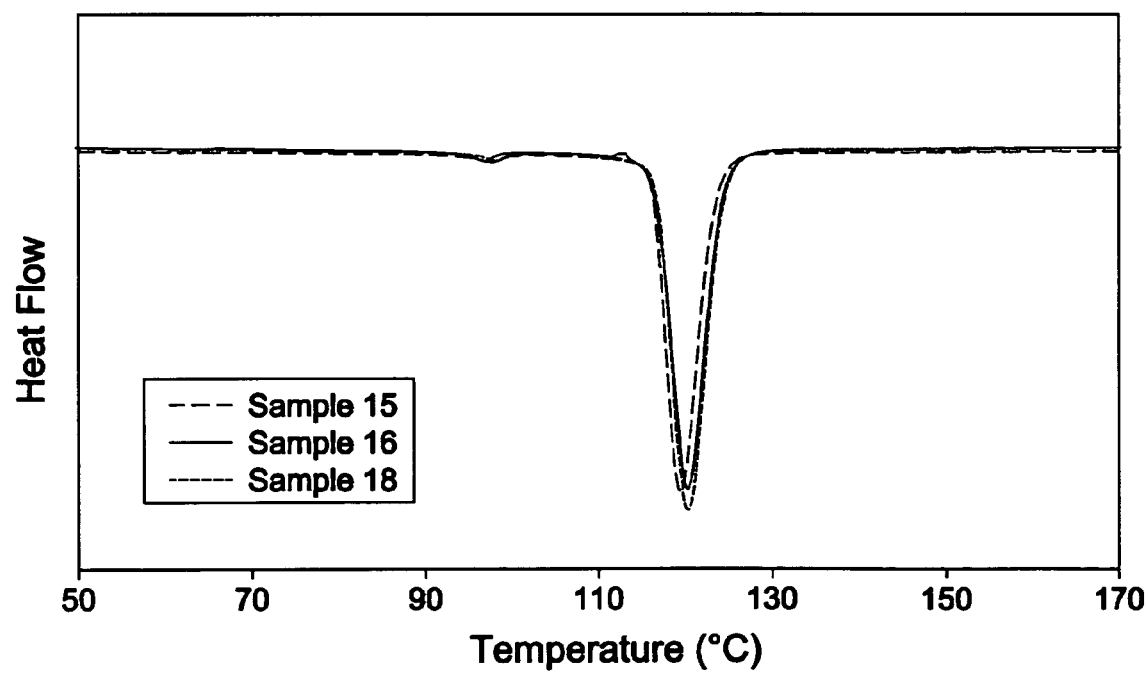
FIG. 10 is a graphical representation of the crystallization heat flow from DSC as a function of temperature for various plasticized propylene impact copolymer samples illustrative of the invention.

The NFP in the current invention is miscible with the propylene polymer, as determined by, for example, the single $T_g$ profile of the plasticized propylene homopolymer and propylene copolymer. This is shown graphically in FIGS. 2-3. The NFP in the current invention is also miscible with the propylene impact copolymer, as determined by, for example, the two $T_g$ profile of the plasticized propylene impact copolymer, one being the lower $T_g$ profile for the ethylene-propylene rubber phase and one being the higher $T_g$ profile for the propylene polymer phase. This is shown graphically in FIG. 4.

Summaries of injection molded properties for these samples are provided in Tables 9-11. Molded parts from the invention plasticized polypropylene homopolymers show a significant decrease in flexural and tensile modulus at a loading of 4 wt % PAO or isoparaffin, while maintaining their tensile strength, room temperature Izod impact resistance and heat deflection temperature. For comparison, molded samples were also prepared with erucamide (cis-13-docosenoamide from Crompton), a common lubricant designed to reduce molded part surface friction of 4 wt % concentration. The effect of the erucamide on the flexural modulus is insignificant, as shown in Table 12.

The addition of NFP substantially improves the impact resistance of molded parts without the significant decrease of heat deflection temperature. For example, Gardner impact strength, at both room and freezing temperatures, has improved from 350% to 400% for propylene homopolymers, from 140 to 165% for propylene copolymers, and from 20 to 40% for propylene impact copolymers due to the addition of 4-5 wt % of NFP. It is anticipated that further increase of impact resistance is attainable by the increase of NFP concentration in the propylene polymers. Other measures of impact resistance, including Izod impact at room and freezing temperatures, are also significantly improved.

Another advantage of the current invention is that the heat deflection temperature of plasticized polyolefins is not compromised (either maintained or only slightly reduced) which is crucial for applications requiring maintenance of molded article dimensions at high temperature. Further indication of toughness improvement is shown by the significant increase of elongation at yield and break. Many applications require good conformability during the end-use. A higher elongation facilitates the compliance of molded articles to the deformation during either the conversion process or at the end-use.

The NFP also demonstrate the ability to provide substantial softness improvement in spunbond nonwoven fabrics, as provided by the lower "total hand" in Table 13. In many applications, particularly in personal hygiene and health care, a soft nonwoven is very desirable for skin contact comfort. The current invention not only provides the improvement in softness but also maintains the necessary tensile strength, tear resistance and fabric uniformity.

Comparison of cast film properties are listed in Table 14. The NFP, particularly the Isopar-V plasticized propylene homopolymer (Sample 2) provides improvement in the tear and impact resistance, as indicated by the relatively high (relative to the unplasticized polyolefin) Elmendorf tear in both machine direction (MD) and transverse direction (TD) and dart impact at both room and freezing temperatures. In addition, the optical properties, i.e., haze and gloss, are also improved. The improvement offers advantages in many film applications, for examples, food packaging, stationery cover, tape, medical and electronic packaging.

Examples in Tables 15-24 Based on Blends Made Using the Brabender Method

Samples presented in Tables 15-24 were blended using the Brabender Method. The data in these tables show similar benefits as those in Tables 6-13. Flowability is enhanced by the addition of the NFP as seen in the increase of MFR. Low temperature toughness increases as evidenced by the rise in Notched Izod at −18° C. Softness is enhanced as seen by a drop in flexural modulus. The Tg drops can be substantial, but the melting point and crystallization point remains essentially unchanged (to within 1-2° C.).

Examples in Tables 25-26 Based on Blends Made Using the Extruder Method

The data in tables 25 and 26 show similar benefits. Flowability is enhanced by the addition of the NFP as seen in the increase of MFR. Toughness increases as evidenced by the rise in impact properties. Softness is enhanced as seen by a drop in flexural modulus, but HDT is largely unaffected. The Tg drops can be substantial, but the melting point and crystallization point remains essentially unchanged (to within 1-2° C.).

Examples in Table 27 Showing Plasticizer Permanence

The loss of plasticizer as a function of time at elevated temperature provides a way to assess permanence of the plasticizer. The results in Table 27 for plasticized propylene random copolymer demonstrate the importance of molecular weight of the plasticizer. The plasticizers were PAO liquids of increasing molecular weight and a white mineral oil. Each plasticized sample was prepared by dry blending granules of the propylene polymer with 10 wt % plasticizer, then was melt mixed using a single-screw extruder to make pellets. A portion was compression molded into 0.25 mm thick sheets for emission testing conducted according to ASTM D1203. Test specimens were 50 mm in diameter. The testing temperature was 70° C. Specimens were weighed at 0, 24, 48, 139, 167, and 311 hours, and percentage of weight loss calculated. Over the prolonged time period examined, only the highest molecular weight PAO did not show any additional weight loss than observed for the neat polymer. Notably, the mineral oil exhibits significantly lower permanence than PAO liquids of comparable KV at 100° C. (>5 wt % lost at 311 hr vs. 1-2 wt % lost for PAO).

Examples in Table 28 Showing Plasticizer Content

The measured plasticizer content in the final blend is compared to the original plasticizer content before blending for several resin/plasticizer combinations in Table 28. Extraction and CRYSTAF method results are compared. In general, there is good agreement between the original blend composition based on component weights and the final composition determined by the analytical methods.

Examples in Tables 29-32 of Spunbond Fabric

Blends of mPP and fluids were prepared by melt-mixing in a single-screw compounding extruder (Extruder Method). 25 gsm (grams per square meter) basis weight spunbond fabrics were obtained at a pilot spunbond line at throughput of 0.4 grams per hole per minute. The fluids demonstrate the ability to provide substantial softness improvement in spunbond nonwoven fabrics, as provided by the lower "total hand" in Table 29. In many applications, particularly in personal hygiene and health care, a soft nonwoven is very desirable for skin contact comfort. The current invention not only provides the improvement in softness but also maintains the necessary tensile strength, tear resistance and fabric uniformity.

Other blends of znPP, mPP and fluids were prepared by melt-mixing in a single-screw compounding extruder (Extruder Method). 34 gsm basis weight fabrics were produced at different throughputs and their softness measured using a handle-o-meter. The "total hand" is summarized in Tables 30 and 31. Significant increase in softness or drop in "total hand" is observed for all fabrics made of plasticized resins. Furthermore, softness increases with increasing fluid concentration. High molecular weight PAO is generally less efficient in increase softness than low molecular weight PAO. Emission loss of PAO during fabrication, addressed using CRYSTAF, is minor as presented in Table 32.

While the present invention has been described and illustrated by reference to particular embodiments, those of ordinary skill in the art will appreciate that the invention lends itself to many different variations not illustrated herein. For these reasons, then, reference should be made solely to the appended claims for purposes of determining the scope of the present invention. Further, certain features of the present invention are described in terms of a set of numerical upper limits and a set of numerical lower limits. It should be appreciated that ranges formed by any combination of these limits are within the scope of the invention unless otherwise indicated.

All priority documents are herein fully incorporated by reference for all jurisdictions in which such incorporation is permitted. Further, all documents cited herein, including testing procedures, are herein fully incorporated by reference for all jurisdictions in which such incorporation is permitted.

TABLE 4a

List of Commercial Polymers used in Examples

| Polymer | Description* | Source |
|---|---|---|
| znPP | Z-N isotactic propylene homopolymer, 12 MFR | PP 1024 E4, ExxonMobil Chemical |
| znPP-2 | Z-N isotactic propylene homopolymer, 36 MFR | PP 3155, ExxonMobil Chemical |
| mPP-1 | metallocene isotactic propylene homopolymer, 24 MFR, $T_m$~152° C. | Achieve ™ 3854, ExxonMobil Chemical |
| mPP-2 | metallocene isotactic propylene homopolymer, 16 MFR | Achieve ™ 1654, ExxonMobil Chemical |
| sPP | syndiotactic propylene homopolymer, 2.2 MFR, 93% syndiotactic, $T_m$~125° C., $M_w$~174 kg/mole, $M_n$~75 kg/mole | Aldrich Chemicals, Catalog # 452149 |
| RCP-1 | Z-N propylene random copolymer, 12 MFR, $T_m$~152° C. | Clarified PP 9054, ExxonMobil Chemical |
| RCP-2 | Z-N propylene random copolymer, 7 MFR, $T_m$~146° C. | PP 9513, ExxonMobil Chemical |
| RCP-3 | Z-N propylene random copolymer, 12 MFR | PP 9374 MED, ExxonMobil Chemical |
| RCP-4 | Z-N propylene random copolymer, 12 MFR | PP 9574 E6, ExxonMobil Chemical |
| ICP-1 | Z-N propylene impact copolymer, 21 MFR, $T_m$~163° C. | PP 7684 E2, ExxonMobil Chemical |
| ICP-2 | Z-N propylene impact copolymer, 8 MFR | PP 7033, ExxonMobil Chemical |
| ICP-3 | Z-N propylene impact copolymer, nucleated, 8 MFR | PP 7033N, ExxonMobil Chemical |

TABLE 4a-continued

List of Commercial Polymers used in Examples

| Polymer | Description* | Source |
|---|---|---|
| TPO | propylene-based thermoplastic polyolefin containing 70 wt % metallocene isotactic propylene homopolymer and 30 wt % metallocene ethylene-butene copolymer (0.88 g/cm³ density, 0.8 MI) | 70 wt % Achieve ™ 3854, 30 wt % Exact ®4033, ExxonMobil Chemical |
| PB | isotactic 1-butene homopolymer, 0.4 MI, $T_m$~125° C., $M_w$~570 kg/mole | Aldrich Chemicals, Catalog # 189391 |

*"Z-N" indicates a Ziegler-Natta catalyst was used for synthesis
"metallocene" indicates an Exxpol ® metallocene catalyst was used for synthesis

TABLE 4b

List of Experimental Polymers used in Examples

| Polymer | Description |
|---|---|
| EP-1 | metallocene propylene-ethylene copolymer, 9 MFR, 11 wt % ethylene made according to EP 1 003 814B1 using dimethylaniliniumtetrakis(pentafluorophenyl) borate and dimethylsilylbis(indenyl)hafnium dimethyl |
| EP-2 | metallocene propylene-ethylene copolymer, 14 MFR, 14 wt % ethylene made according to EP 1 003 814B1 using dimethylaniliniumtetrakis(pentafluorophenyl) borate and dimethylsilylbis(indenyl)hafnium dimethyl |

TABLE 5a

List of Fluids used as Plasticizers in Examples

| Fluid | Description | Source |
|---|---|---|
| SHF-21 | PAO liquid | ExxonMobil Chemical |
| SHF-41 | PAO liquid | ExxonMobil Chemical |
| SHF-61 | PAO liquid | ExxonMobil Chemical |
| SHF-82 | PAO liquid | ExxonMobil Chemical |
| SHF-101 | PAO liquid (also SpectraSyn ™ 10) | ExxonMobil Chemical |
| SHF-403 | PAO liquid (also SpectraSyn ™ 40) | ExxonMobil Chemical |
| SHF-1003 | PAO liquid (also SpectraSyn ™ 100) | ExxonMobil Chemical |
| SuperSyn 2150 | PAO liquid (also SpectraSyn Ultra ™ 150) | ExxonMobil Chemical |
| SuperSyn 23000 | PAO liquid | ExxonMobil Chemical |
| Rudol | white mineral oil | Crompton |
| Freezene 200 | white mineral oil | Crompton |
| ParaLux 6001R | paraffinic process oil | Chevron |
| Isopar V | isoparaffinic hydrocarbon fluid | ExxonMobil Chemical |
| Norpar 15 | normal paraffinic hydrocarbon fluid | ExxonMobil Chemical |
| Exxsol D130 | dearomatized aliphatic hydrocarbon fluid | ExxonMobil Chemical |
| CORE 2500 | Group I basestock | ExxonMobil Chemical |
| EHC 110 | Group II basestock | ExxonMobil Chemical |
| VISOM 6 | Group III basestock | ExxonMobil Chemical |
| VHVI-8 | Group III basestock | PetroCanada |
| GTL6/MBS | Group III basestock | ExxonMobil Chemical |
| GTL14/HBS | Group III basestock | ExxonMobil Chemical |
| TPC 137 | polyisobutylene liquid | Texas Petrochemicals |
| Lucant HC-10 | Blend of decene oligomer with an ethylene/α-olefin liquid | Mitsui Chemicals America |
| C-9900 | polybutene liquid | Infineum |

TABLE 5b

Properties of PAO Fluids used as Plasticizers in Examples

| Fluid | KV, 40° C. (cSt) | KV, 100° C. (cSt) | VI (--) | pour point (° C.) | Mn (g/mole) | Cn | specific gravity |
|---|---|---|---|---|---|---|---|
| SHF-21 | 5 | <2 | N.D. | -66 | 280[#] | 20 | 0.798 |
| SHF-41 | 19 | 4 | 126 | -66 | 450[#] | 32 | 0.820 |
| SHF-61 | 31 | 6 | 138 | -57 | 540[#] | 38 | 0.827 |
| SHF-82 | 48 | 8 | 139 | -48 | 640[#] | 46 | 0.833 |
| SHF-101 | 66 | 10 | 137 | -48 | 720[#] | 51 | 0.835 |
| SHF-403 | 396 | 39 | 147 | -36 | 1,700[+] | 120 | 0.850 |
| SHF-1003 | 1240 | 100 | 170 | -30 | 3,000[+] | 210 | 0.853 |
| SuperSyn 2150 | 1,500 | 150 | 218 | -33 | 3,700[+] | 260 | 0.850 |
| SuperSyn 23000 | 35,000 | 2,800 | 360 | -9 | 18,800[+] | 1,340 | 0.855 |
| Rudol | 29 | 5 | 103 | -24 | 400 | 28 | 0.86 [a] |
| Freezene 200 | 39 | 5 | 38 | -42 | 350 | 25 | 0.88 [a] |
| ParaLux 6001R | 116 | 12 | 99 | -12 | 580 | 41 | 0.87 |
| Isopar V | 9 | <2 | N.D. | -63 | 240[#] | 17 | 0.82 |
| Norpar 15 | 2 | <2 | N.D. | 7 | 210[#] | 15 | 0.77 |
| Exxsol D130 | 4 | <2 | N.D. | -6 | 250[#] | 18 | 0.83 |
| CORE 2500 | 490 | 32 | 95 | -6 | 800* | 57 | 0.896 |
| EHC 110 | 99 | 11 | 95 | -12 | 500* | 36 | 0.860 |
| VISOM 6 | 35 | 7 | 148 | -18 | 510* | 36 | 0.836 |
| VHVI-8 | 50 | 8 | 129 | -12 | 560 | 40 | 0.850 |
| GTL6/MBS | 30 | 6 | 156 | -18 | 510* | 36 | 0.823 |
| GTL14/HBS | 95 | 14 | 155 | -24 | 750* | 53 | 0.834 |
| TPC 137 | 30 | 6 | 132 | -51 | 350 | 25 | 0.845 |
| Lucant HC-10 | 60 | 10 | 150 | -53 | 590 | 42 | 0.826 [b] |
| C-9900 | 140 | 12 | 60 | -36 | 540 | 38 | 0.846 |

N.D. = not defined, due to KV at 100° C. < 2 cSt.
Mn reported by manufacturer or estimated according to ASTM D2502, except as indicated:
*estimated by freezing point depression,
[#]measured by GC,
[+]measured by GPC. Specific gravity at 60° F. (15.6° C.) except
[a] at 25° C. or
[b] at 20° C.

TABLE 6

Resin properties of plasticized mPP-1 propylene homopolymer

| | Sample No. | | | | | | | | |
|---|---|---|---|---|---|---|---|---|---|
| | 1 | 2 | 3 | 4 | 5 | 6 | 7 | 8 | 9 |
| NFP | none | Isopar-V | SHF-101 | SHF-403 | SuperSyn-2150 | Isopar-V | SHF-403 | SuperSyn-2150 | SuperSyn-23000 |
| Concentration of NFP (wt%) | 0 | 4 | 4 | 4 | 4 | 10 | 10 | 10 | 10 |
| Resin Properties | | | | | | | | | |
| MFR | 23 | 32 | 29 | 29 | 29 | 51 | 45 | 39 | 37 |
| Melting Temperature (° C.) | 152 | 151 | 153 | 152 | 153 | 152 | 151 | 152 | 152 |
| Crystallization Temperature (° C.) | 115 | 115 | 118 | 118 | 118 | 115 | 116 | 115 | 115 |
| Glass Transition Temperature (° C.) | 4 | −1 | −1 | 0 | 2 | −11 | −5 | −3 | 1 |

TABLE 7

Resin properties of plasticized RCP-1 propylene random copolymer

| | Sample No. | | | | |
|---|---|---|---|---|---|
| | 10 | 11 | 12 | 13 | 14 |
| NFP | None | Isopar-V | SHF-101 | SHF-403 | SuperSyn-2150 |
| Concentration of NFP (wt %) | 0 | 5 | 5 | 5 | 5 |
| Resin Properties | | | | | |
| MFR | 12 | 16 | 16 | 15 | 15 |
| Melting Temperature (° C.) | 152 | 152 | 152 | 152 | 152 |
| Crystallization Temperature (° C.) | 122 | 121 | 121 | 121 | 121 |
| Glass Transition Temperature (° C.) | 1 | −7 | −5 | −3 | −1 |

TABLE 8

Resin properties of plasticized ICP-1 propylene impact copolymer

| | Sample No. | | | | |
|---|---|---|---|---|---|
| | 15 | 16 | 17 | 18 | 19 |
| NFP | None | Isopar-V | SHF-101 | SHF-403 | SuperSyn-2150 |
| Concentration of NFP (wt %) | 0 | 5 | 5 | 5 | 5 |
| Resin Properties | | | | | |
| Melt Flow Rate | 23 | 32 | 29 | 29 | 29 |
| Melting Temperature (° C.) | 163 | 162 | 162 | 162 | 162 |
| Crystallization Temperature (° C.) | 119 | 120 | 120 | 120 | 121 |
| Glass Transition Temperature (° C.) | −53, 5.2 | −55, −3 | −56, −4 | −50, −1 | −52, 1 |

TABLE 9

Molded part properties of plasticized mPP-1 propylene homopolymer

| | Sample No. | | | | |
|---|---|---|---|---|---|
| | 1 | 2 | 3 | 4 | 5 |
| NFP: | none | Isopar V | SHF-101 | SHF-403 | SuperSyn-2150 |
| Concentration of NFP (wt %) | 0 | 4 | 4 | 4 | 4 |
| Optical Properties | | | | | |
| Haze (%) | 65 | 62 | 65 | 61 | 64 |
| Gloss @ 45° | 85 | 87 | 86 | 85 | 86 |
| Mechanical Properties | | | | | |
| Tensile Strength @ Yield (kpsi) | 4.9 | 4.4 | 4.5 | 4.5 | 4.6 |
| Elongation @ Yield (%) | 9 | 12 | 11 | 11 | 10 |
| Flexural Modulus, 1% Secant (kpsi) | 200 | 155 | 175 | 177 | 179 |
| Heat Deflection Temperature @ 66 psi (° C.) | 105 | 101 | 108 | 107 | 104 |
| Rockwell Hardness (R-Scale) | 104 | 97 | 99 | 99 | 99 |
| Impact Properties | | | | | |
| Notched Izod Impact @ 23° C. (ft-lb/in) | 0.4 | 0.7 | 0.6 | 0.6 | 0.5 |
| Gardner Impact Strength @ 23° C. (in-lb) | 31 | 153 | 166 | 164 | 141 |
| Gardner Impact Strength @ 0° C. (in-lb) | —[a] | 14 | <8[b] | <8[b] | <8[b] |

[a] Samples too brittle to perform this test.
[b] Samples failed at the lowest hammer weight.

TABLE 10

Molded part properties of plasticized RCP-1 propylene random copolymer

| | Sample No. | | | | |
|---|---|---|---|---|---|
| | 10 | 11 | 12 | 13 | 14 |
| NFP: | None | Isopar V | SHF-101 | SHF-403 | SuperSyn-2150 |
| Concentration of NFP (wt %) | 0 | 5 | 5 | 5 | 5 |
| Optical Properties | | | | | |
| Haze (%) | 8.2 | 10.3 | 8.7 | 11.7 | 11.6 |
| Gloss @ 45° | 80 | 81 | 79 | 75 | 76 |
| Mechanical Properties | | | | | |
| Tensile Strength @ Yield (kpsi) | 5.0 | 4.4 | 4.4 | 4.4 | 4.4 |
| Elongation @ Yield (%) | 9 | 14 | 13 | 11 | 11 |
| Elongation @ Break (%) | 185 | 754 | 559 | 259 | 196 |
| Flexural Modulus, 1% Secant (kpsi) | 205 | 141 | 158 | 166 | 173 |
| Heat Deflection Temperature @ 66 psi (° C.) | 87 | 84 | 85 | 77 | 77 |
| Impact Properties | | | | | |
| Notched Izod Impact @ 23° C. (ft-lb/in) | 0.9 | 2.0 | 1.2 | 1.2 | 1.2 |
| Reversed Notched Izod Impact @ −18° C. (ft-lb/in) | 3.9 | 12.6 | 12.4 | 10.5 | 9.0 |
| Gardner Impact Strength @ 23° C. (in-lb) | 83 | 203 | 207 | 201 | 219 |

TABLE 11

Molded part properties of plasticized ICP-1 propylene impact copolymer

| | Sample No. | | | | |
|---|---|---|---|---|---|
| | 15 | 16 | 17 | 18 | 19 |
| NFP: | None | Isopar V | SHF-101 | SHF-403 | SuperSyn-2150 |
| Concentration of NFP (wt %) | 0 | 5 | 5 | 5 | 5 |
| Mechanical Properties | | | | | |
| Tensile Strength @ Yield (kpsi) | 3.3 | 3.0 | 3.0 | 3.0 | 3.0 |
| Elongation @ Yield (%) | 5 | 12 | 10 | 8 | 8 |
| Elongation @ Break (%) | 125 | 230 | 185 | 120 | 110 |
| Flexural Modulus, 1% Secant (kpsi) | 163 | 112 | 124 | 132 | 135 |
| Heat Deflection Temperature @ 66 psi (° C.) | 95 | 81 | 88 | 84 | 86 |
| Impact Properties | | | | | |
| Notched Izod Impact @ 23° C. (ft-lb/in) | 4.8 | 6.5 | 6.0 | 3.9 | 3.5 |
| Gardner Impact Strength @ −29° C. (in-lb) | 123 | 170 | 165 | 159 | 148 |

TABLE 12

Molded part properties of plasticized mPP-1 propylene homopolymer

| | Sample No. | | | | |
|---|---|---|---|---|---|
| | 20 | 21 | 22 | 23 | 24 |
| NFP | None | Isopar V | SHF-403 | SuperSyn-23000 | Erucamide |
| Concentration of NFP (%) | 0 | 4 | 4 | 4 | 4 |
| Resin Properties | | | | | |
| MFR | 24 | 35 | 33 | 30 | 23 |
| Mechanical Properties | | | | | |
| Tensile Strength @ Yield (kpsi) | 4.7 | 4.5 | 4.4 | 4.5 | 4.5 |
| Elongation @ Yield (%) | 9 | 11 | 11 | 10 | 11 |
| Flexural Modulus, 1% Secant (kpsi) | 190 | 155 | 170 | 180 | 188 |
| Heat Deflection Temperature @ 66 psi (° C.) | 92 | 94 | 90 | 90 | 89 |
| Impact Properties | | | | | |
| Notched Izod Impact @ 23° C. (ft-lb/in) | 0.4 | 0.5 | 0.3 | 0.4 | 0.4 |
| Reverse Notched Izod Impact @ −18° C. (ft-lb/in) | 2.7 | 3.1 | 3.0 | n/a | n/a |

TABLE 13

Softness properties of spunbond nonwoven fabrics made of plasticized mPP-1 propylene homopolymer

| | Sample No. | | | | |
|---|---|---|---|---|---|
| | 1 | 2 | 3 | 4 | 5 |
| NFP: | none | Isopar V | SHF-101 | SHF-403 | SuperSyn-2150 |
| Concentration of NFP (%) | 0 | 4 | 4 | 4 | 4 |
| Fabric Properties | | | | | |
| Peak Load (lbs) MD/TD | 9.4/4.8 | 8.0/4.4 | 7.8/4.1 | 8.3/4.1 | 7.5/3.9 |
| Elongation @ Break (%) MD/TD | 76/77 | 65/76 | 58/67 | 72/73 | 64/73 |
| Elmendorf Tear (g/basis weight) TD | 17 | 19 | 15 | 18 | 20 |
| Total Hand (grams) | 31 | 32 | 24 | 21 | 15 |

Properties per total hand. Total hand is based on measurements on fabrics at 25 gsm (grams per square meter).

TABLE 14

Cast film properties of plasticized mPP-1 propylene homopolymer

| | Sample No. | | | | |
|---|---|---|---|---|---|
| | 1 | 2 | 3 | 4 | 5 |
| NFP: | none | Isopar V | SHF-101 | SHF-403 | SuperSyn-2150 |
| Concentration of NFP (%) | 0 | 4 | 4 | 4 | 4 |

TABLE 14-continued

Cast film properties of plasticized mPP-1 propylene homopolymer

| | Sample No. | | | | |
|---|---|---|---|---|---|
| | 1 | 2 | 3 | 4 | 5 |
| Optical Properties | | | | | |
| Haze (%) | 8.8 | 6.2 | 16.7 | 14.7 | 10.5 |
| Gloss | 68 | 70 | 57 | 58 | 65 |
| Mechanical Properties | | | | | |
| 1% Sec. Modulus (kpsi) MD/TD | 140/130 | 84/86 | 119/120 | 133/121 | 120/115 |
| Tensile Strength @ Break (kpsi) MD/TD | 7.6/7.8 | 7.5/7.1 | 7.1/7.5 | 7.2/7.0 | 7.0/6.9 |
| Elongation @ Break (%) MD/TD | 730/728 | 725/680 | 770/792 | 785/765 | 738/739 |
| Elmendorf Tear (g/mil) MD | 29/32 | 54/58 | 17/19 | 17/18 | 22/24 |
| Puncture (lb/mil) | 9.0 | 8.1 | 8.6 | 8.6 | 9.2 |
| Puncture Energy (in · lb/mil) | 18 | 21 | 19 | 17 | 20 |
| Total Energy Dart Impact (ft · lb) | | | | | |
| @ 23° C. | 0.4 | 1.9 | 0.6 | 0.7 | 0.6 |
| @ −15° C. | 0.04 | 0.07 | 0.09 | 0.09 | 0.05 |

Film properties are based on 2 mil thickness.

TABLE 15a

Tensile modulus and yield properties for plasticized znPP propylene homopolymer

| Plasticizer type | Plasticizer content (wt %) | Young's Modulus (kpsi) | Yield Stress (psi) | Yield Strain (%) | Energy to Yield (ft-lbf) |
|---|---|---|---|---|---|
| — | 0 | 130.2 | 4934 | 12.4 | 21.0 |
| Rudol | 5 | 92.1 | 4578 | 17.8 | 27.3 |
| Rudol | 10 | 75.2 | 3947 | 21.6 | 28.5 |
| SHF-101 | 5 | 98.5 | 4614 | 17.3 | 26.9 |
| SHF-101 | 10 | 78.9 | 3844 | 23.3 | 31.2 |
| SHF-101 | 20 | 48.7 | 2658 | 44.1 | 41.8 |
| SHF-403 | 5 | 102.2 | 4547 | 16.9 | 26.5 |
| SHF-403 | 10 | 86.4 | 4006 | 20.0 | 27.3 |
| SuperSyn 2150 | 5 | 108.8 | 4736 | 16.1 | 26.4 |
| SuperSyn 2150 | 10 | 88.5 | 4131 | 19.3 | 26.9 |
| Isopar V | 5 | 93.4 | 4716 | 17.8 | 28.0 |
| IsoPar V | 10 | 70.3 | 4100 | 20.9 | 28.0 |
| Norpar 15 | 5 | 90.3 | 4627 | 17.7 | 27.2 |
| Norpar 15 | 10 | 80.4 | 4304 | 20.5 | 28.7 |
| Exxsol D130 | 5 | 87.8 | 4628 | 18.3 | 28.1 |
| Exxsol D130 | 10 | 71.5 | 4038 | 21.9 | 29.0 |
| CORE 2500 | 5 | 103.3 | 4720 | 17.0 | 27.2 |
| EHC 110 | 5 | 98.9 | 4680 | 17.6 | 27.9 |
| VISOM 6 | 5 | 92.4 | 4576 | 17.8 | 27.3 |
| VHVI-8 | 5 | 92.4 | 4577 | 17.8 | 27.4 |
| GTL6/MBS | 5 | 92.3 | 4526 | 18.6 | 28.2 |
| GTL14/HBS | 5 | 97.1 | 4525 | 18.3 | 28.2 |
| TPC 137 | 5 | 94.5 | 4617 | 18.3 | 28.6 |
| Lucant HC-10 | 5 | 97.9 | 4701 | 17.8 | 28.3 |
| C-9900 | 5 | 100.3 | 4641 | 17.6 | 27.8 |

TABLE 15b

Tensile break properties for plasticized znPP propylene homopolymer

| Plasticizer type | Plasticizer content (wt %) | Break stress (psi) | Break Strain (%) | Energy to Break (ft-lbf) |
|---|---|---|---|---|
| — | 0 | 3428 | 639 | 72.5 |
| Rudol | 5 | 3080 | 643 | 71.2 |
| Rudol | 10 | 3093 | 663 | 69.9 |
| SHF-101 | 5 | 3121 | 700 | 77.5 |
| SHF-101 | 10 | 3003 | 683 | 71.6 |
| SHF-101 | 20 | 2632 | 53 | 4.3 |
| SHF-403 | 5 | 3003 | 608 | 67.3 |
| SHF-403 | 10 | 2953 | 620 | 65.2 |
| SuperSyn 2150 | 5 | 3027 | 521 | 58.5 |
| SuperSyn 2150 | 10 | 2875 | 413 | 43.7 |
| Isopar V | 5 | 3212 | 672 | 75.2 |
| IsoPar V | 10 | 3380 | 717 | 76.9 |
| Norpar 15 | 5 | 3516 | 714 | 79.9 |
| Norpar 15 | 10 | 3451 | 678 | 73.8 |
| Exxsol D130 | 5 | 3339 | 708 | 78.6 |
| Exxsol D130 | 10 | 3482 | 693 | 74.1 |
| CORE 2500 | 5 | 3092 | 741 | 81.8 |
| EHC 110 | 5 | 3142 | 690 | 76.7 |
| VISOM 6 | 5 | 3146 | 687 | 76.4 |
| VHVI-8 | 5 | 3190 | 696 | 78.4 |
| GTL6/MBS | 5 | 3484 | 699 | 78.4 |
| GTL14/HBS | 5 | 3235 | 687 | 76.6 |
| TPC 137 | 5 | 3195 | 725 | 79.7 |
| Lucant HC-10 | 5 | 3128 | 699 | 78.3 |
| C-9900 | 5 | 3276 | 698 | 77.1 |

TABLE 15c

Flexure and Notched Izod impact properties for plasticized znPP propylene homopolymer

| Plasticizer type | Plasticizer content (wt %) | 1% Secant Modulus (kpsi) | 2% Secant Modulus (kpsi) | −18° C. RNI* impact resistance (ft-lb/in) |
|---|---|---|---|---|
| — | 0 | 189.6 | 171.5 | 2.7 |
| Rudol | 5 | 145.4 | 128.7 | 4.3 |
| Rudol | 10 | 107.9 | 94.7 | 10.1 |
| SHF-101 | 5 | 153.8 | 135.7 | 4.7 |
| SHF-101 | 10 | 116.0 | 101.2 | 13.0 |
| SHF-101 | 20 | 65.8 | 57.7 | 6.3 |
| SHF-403 | 5 | 163.8 | 145.2 | 3.0 |
| SHF-403 | 10 | 123.4 | 107.9 | 8.7 |
| SuperSyn 2150 | 5 | 170.2 | 151.5 | 3.1 |
| SuperSyn 2150 | 10 | 132.2 | 115.8 | 7.2 |
| Isopar V | 5 | 145.6 | 128.9 | 3.6 |
| IsoPar V | 10 | 109.2 | 96.3 | 10.2 |
| Norpar 15 | 5 | 143.6 | 126.8 | 8.2 |
| Norpar 15 | 10 | 120.8 | 106.0 | 12.1 |
| Exxsol D130 | 5 | 138.7 | 122.1 | 7.8 |
| Exxsol D130 | 10 | 106.8 | 94.3 | 14.7 |
| CORE 2500 | 5 | 155.4 | 137.8 | 2.8 |
| EHC 110 | 5 | 146.6 | 129.6 | 3.3 |
| VISOM 6 | 5 | 147.6 | 130.1 | 7.7 |
| VHVI-8 | 5 | 147.3 | 130.0 | 5.9 |
| GTL6/MBS | 5 | 144.4 | 126.8 | 8.5 |
| GTL14/HBS | 5 | 160.8 | 140.2 | 7.4 |
| TPC 137 | 5 | 145.5 | 128.8 | 6.2 |
| Lucant HC-10 | 5 | 148.5 | 130.5 | 6.2 |
| C-9900 | 5 | 146.7 | 129.9 | 3.2 |

*Results were obtained using the Reversed Notched Izod testing protocol (ASTM D256E).

TABLE 15d

Rheological properties for plasticized znPP propylene homopolymer

| Plasticizer type | Plasticizer content (wt %) | $\eta_0$ (Pa·s) | $\lambda$ (s) | N | MFR (g/10 min) |
|---|---|---|---|---|---|
| — | 0 | 2243 | 0.075 | 0.325 | 11.51 |
| Rudol | 5 | | | | |
| Rudol | 10 | 1334 | 0.057 | 0.328 | 32.22 |
| SHF-101 | 5 | 1786 | 0.067 | 0.324 | |
| SHF-101 | 10 | 1311 | 0.053 | 0.311 | 31.75 |
| SHF-101 | 20 | 753 | 0.039 | 0.309 | |
| SHF-403 | 5 | 1827 | 0.068 | 0.323 | 18.99 |
| SHF-403 | 10 | 1366 | 0.055 | 0.314 | 29.01 |
| SuperSyn 2150 | 5 | 1822 | 0.069 | 0.323 | 17.93 |
| SuperSyn 2150 | 10 | 1385 | 0.056 | 0.323 | |
| Isopar V | 5 | 1876 | 0.068 | 0.329 | |
| IsoPar V | 10 | 1414 | 0.059 | 0.332 | 28.74 |
| Norpar 15 | 5 | 1943 | 0.071 | 0.334 | |
| Norpar 15 | 10 | 1698 | 0.069 | 0.335 | 28.85 |
| Exxsol D130 | 5 | 1927 | 0.071 | 0.331 | 16.78 |
| Exxsol D130 | 10 | 1583 | 0.063 | 0.327 | |
| CORE 2500 | 5 | | | | |
| EHC 110 | 5 | 1835 | 0.069 | 0.327 | 17.52 |
| VISOM 6 | 5 | 1780 | 0.068 | 0.326 | 18.16 |
| VHVI-8 | 5 | 1764 | 0.064 | 0.323 | 20.27 |
| GTL6/MBS | 5 | 1745 | 0.065 | 0.322 | |
| GTL14/HBS | 5 | 1828 | 0.069 | 0.322 | |
| TPC 137 | 5 | 1834 | 0.068 | 0.327 | 23.19 |
| Lucant HC-10 | 5 | 1776 | 0.066 | 0.318 | 17.10 |
| C-9900 | 5 | 1816 | 0.068 | 0.325 | |

TABLE 15e1

DSC properties for plasticized znPP propylene homopolymer

| Plasticizer type | Plasticizer content (wt %) | $T_m$ at onset, first heating (°C.) | $T_m$ at peak, first heating (°C.) | $\Delta H_f$, first heating (J/g) | $T_c$ at onset (°C.) | $T_c$ at peak (°C.) |
|---|---|---|---|---|---|---|
| — | 0 | | 166.0 | 95.8 | 114.7 | 109.0 |
| Rudol | 5 | 150.8 | 166.9 | 98.6 | 117.1 | 108.0 |
| Rudol | 10 | 150.0 | 163.7 | 87.7 | 116.3 | 109.5 |
| SHF-101 | 5 | 151.7 | 167.1 | 93.8 | 118.4 | 110.0 |
| SHF-101 | 10 | 151.2 | 164.7 | 86.6 | 116.6 | 108.7 |
| SHF-101 | 20 | 149.3 | 162.4 | 79.5 | 113.1 | 106.8 |
| SHF-403 | 5 | 151.0 | 167.4 | 89.2 | 117.6 | 109.2 |
| SHF-403 | 10 | 152.9 | 165.6 | 86.8 | 117.5 | 110.6 |
| SuperSyn 2150 | 5 | 151.5 | 167.7 | 102.3 | 118.9 | 110.6 |
| SuperSyn 2150 | 10 | 153.6 | 166.1 | 88.0 | 117.0 | 110.9 |
| Isopar V | 5 | 148.9 | 166.6 | 92.3 | 116.7 | 110.0 |
| IsoPar V | 10 | 149.4 | 163.9 | 82.8 | 116.5 | 107.6 |
| Norpar 15 | 5 | 149.1 | 166.2 | 98.2 | 116.5 | 109.3 |
| Norpar 15 | 10 | 151.6 | 165.3 | 86.7 | 117.5 | 109.6 |
| Exxsol D130 | 5 | 150.4 | 166.6 | 89.5 | 117.1 | 109.6 |
| Exxsol D130 | 10 | | | | | |
| CORE 2500 | 5 | 152.4 | 167.6 | 91.5 | 116.0 | 106.5 |
| EHC 110 | 5 | 150.8 | 167.0 | 91.0 | 116.3 | 108.4 |
| VISOM 6 | 5 | 151.6 | 167.0 | 94.4 | 117.4 | 108.7 |
| VHVI-8 | 5 | 150.1 | 167.3 | 87.7 | 116.7 | 109.4 |
| GTL6/MBS | 5 | | | | | |
| GTL14/HBS | 5 | | | | | |
| TPC 137 | 5 | 151.8 | 167.6 | 85.2 | 117.0 | 108.8 |
| Lucant HC-10 | 5 | | | | | |
| C-9900 | 5 | 149.9 | 166.8 | 94.4 | 117.2 | 109.9 |

TABLE 15e2

DSC properties for plasticized znPP propylene homopolymer

| Plasticizer type | Plasticizer content (wt %) | $T_m$ at onset, second heating (°C.) | $T_m$ at peak, second heating (°C.) | $\Delta H_f$, second heating (J/g) |
|---|---|---|---|---|
| — | 0 | | 161.4 | 96.2 |
| Rudol | 5 | 153.4 | 164.5 | 102.0 |
| Rudol | 10 | 151.1 | 158.5 | 93.3 |
| SHF-101 | 5 | 154.0 | 164.9 | 94.2 |
| SHF-101 | 10 | 151.6 | 159.4 | 85.4 |
| SHF-101 | 20 | 146.9 | 161.0 | 81.4 |
| SHF-403 | 5 | 154.6 | 166.0 | 93.5 |
| SHF-403 | 10 | 153.5 | 160.7 | 94.8 |
| SuperSyn 2150 | 5 | 154.7 | 165.8 | 107.8 |
| SuperSyn 2150 | 10 | 154.4 | 161.0 | 98.4 |
| Isopar V | 5 | 154.0 | 164.9 | 101.8 |
| IsoPar V | 10 | 153.8 | 164.9 | 95.0 |
| Norpar 15 | 5 | 154.4 | 164.7 | 97.5 |
| Norpar 15 | 10 | 155.1 | 161.0 | 97.0 |
| Exxsol D130 | 5 | 154.4 | 165.2 | 91.6 |
| Exxsol D130 | 10 | | | |
| CORE 2500 | 5 | 153.2 | 166.5 | 97.5 |
| EHC 110 | 5 | 153.0 | 165.3 | 98.9 |
| VISOM 6 | 5 | 153.2 | 165.1 | 101.3 |
| VHVI-8 | 5 | 153.8 | 164.6 | 96.2 |
| GTL6/MBS | 5 | | | |
| GTL14/HBS | 5 | | | |
| TPC 137 | 5 | 154.2 | 165.7 | 91.2 |
| Lucant HC-10 | 5 | | | |
| C-9900 | 5 | 153.2 | 165.2 | 102.6 |

TABLE 15f1

DMTA properties for plasticized znPP propylene homopolymer

| Plasticizer type | Plasticizer content (wt %) | $T_g$ at onset (°C.) | $T_g$ at peak (°C.) | Peak Area |
|---|---|---|---|---|
| — | 0 | −9.7 | 4.7 | 0.19 |
| Rudol | 5 | −39.4 | −5.2 | 0.61 |
| Rudol | 10 | −51.5 | −10.4 | 0.70 |
| SHF-101 | 5 | −44.0 | −5.9 | 0.51 |
| SHF-101 | 10 | −54.9 | −12.1 | 0.65 |
| SHF-101 | 20 | −78.7 | −36.9 | 0.94 |
| SHF-403 | 5 | −39.0 | −3.8 | 0.45 |
| SHF-403 | 10 | −45.2 | −7.0 | 0.62 |
| SuperSyn 2150 | 5 | −36.9 | −0.5 | 0.26 |
| SuperSyn 2150 | 10 | −41.5 | −6.9 | 0.49 |
| Isopar V | 5 | −33.5 | −4.6 | 0.41 |
| IsoPar V | 10 | −46.9 | −10.7 | 0.73 |
| Norpar 15 | 5 | −46.1 | −9.0 | 0.38 |
| Norpar 15 | 10 | −46.6 | −16.4 | 0.57 |
| Exxsol D130 | 5 | −40.2 | −9.4 | 0.60 |
| Exxsol D130 | 10 | | | |
| CORE 2500 | 5 | −34.3 | −0.7 | 0.36 |
| EHC 110 | 5 | −36.3 | −3.1 | 0.47 |
| VISOM 6 | 5 | −47.3 | −6.4 | 0.47 |
| VHVI-8 | 5 | −39.7 | −8.2 | −0.56 |
| GTL6/MBS | 5 | | | |
| GTL14/HBS | 5 | | | |
| TPC 137 | 5 | −38.7 | −5.25 | 0.45 |
| Lucant HC-10 | 5 | −39 | −5.2 | 0.39 |
| C-9900 | 5 | −33.5 | −5 | 0.46 |

TABLE 15f2

DMTA properties for plasticized znPP propylene homopolymer

| Plasticizer type | Plasticizer content (wt %) | E' before $T_g$ (MPa) | E' at 25° C. (MPa) |
|---|---|---|---|
| — | 0 | 3199 | 1356 |
| Rudol | 5 | 3250 | 714 |
| Rudol | 10 | 4040 | 919 |
| SHF-101 | 5 | 3201 | 915 |
| SHF-101 | 10 | 3776 | 986 |
| SHF-101 | 20 | 3209 | 522 |
| SHF-403 | 5 | 3056 | 739 |
| SHF-403 | 10 | 3001 | 726 |
| SuperSyn 2150 | 5 | 3047 | 929 |
| SuperSyn 2150 | 10 | 2829 | 685 |
| Isopar V | 5 | 2681 | 853 |
| IsoPar V | 10 | 3437 | 673 |
| Norpar 15 | 5 | 4037 | 1210 |
| Norpar 15 | 10 | 3623 | 1034 |
| Exxsol D130 | 5 | 2973 | 723 |
| Exxsol D130 | 10 | | |
| CORE 2500 | 5 | 3716 | 1170 |
| EHC 110 | 5 | 3193 | 743 |
| VISOM 6 | 5 | 3782 | 1009 |
| VHVI-8 | 5 | 3459 | 847 |
| GTL6/ MBS | 5 | | |
| GTL14/HBS | 5 | | |
| TPC 137 | 5 | 2836 | 784 |
| Lucant HC-10 | 5 | 3165 | 762 |
| C-9900 | 5 | 2808 | 835.6 |

TABLE 16a

Tensile modulus and yield properties for plasticized mPP-1 propylene homopolymer

| Plasticizer type | Plasticizer content (wt %) | Young's Modulus (kpsi) | Yield Stress (psi) | Yield Strain (%) | Energy to Yield (ft-lbf) |
|---|---|---|---|---|---|
| — | 0 | 132.3 | 4983 | 11.3 | 18.9 |
| Rudol | 10 | 68.9 | 3852 | 20.5 | 26.5 |
| Freezene 200 | 10 | 65.6 | 3930 | 20.5 | 26.9 |
| SHF-403 | 5 | 88.1 | 4338 | 15.5 | 22.9 |
| SHF-403 | 10 | 70.9 | 3888 | 18.8 | 25.1 |
| CORE 2500 | 10 | 70.0 | 3869 | 18.7 | 24.6 |
| VISOM 6 | 10 | 59.1 | 3574 | 21.3 | 25.9 |
| C-9900 | 10 | 65.6 | 3778 | 20.3 | 26.0 |

TABLE 16b

Tensile break properties for plasticized mPP-1 propylene homopolymer

| Plasticizer type | Plasticizer content (wt %) | Break stress (psi) | Break Strain (%) | Energy to Break (ft-lbf) |
|---|---|---|---|---|
| — | 0 | 3336 | 654 | 69.1 |
| Rudol | 10 | 4307 | 853 | 92.1 |
| Freezene 200 | 10 | 4414 | 875 | 95.4 |
| SHF-403 | 5 | 4375 | 857 | 92.6 |
| SHF-403 | 10 | 4235 | 866 | 92.7 |
| CORE 2500 | 10 | 4234 | 858 | 91.2 |
| VISOM 6 | 10 | 4150 | 851 | 88.1 |
| C-9900 | 10 | 4249 | 906 | 95.3 |

TABLE 16c

Flexure and Notched Izod impact properties for plasticized mPP-1 propylene homopolymer

| Plasticizer type | Plasticizer content (wt %) | 1% Secant Modulus (kpsi) | 2% Secant Modulus (kpsi) | −18° C. RNI* impact resistance (ft-lb/in) |
|---|---|---|---|---|
| — | 0 | 180.4 | 165.8 | 2.5 |
| Rudol | 10 | 99.6 | 89.5 | 10.2 |
| Freezene 200 | 10 | 102.6 | 91.8 | 5.7 |
| SHF-403 | 5 | 156.9 | 141.3 | 2.6 |
| SHF-403 | 10 | 120.5 | 106.9 | 5.8 |
| CORE 2500 | 10 | 114.3 | 101.5 | 4.4 |
| VISOM 6 | 10 | 106.3 | 94.4 | 13.3 |
| C-9900 | 10 | 104.9 | 93.8 | 5.8 |

*Results were obtained using the Reversed Notched Izod testing protocol (ASTM D256E).

TABLE 16d

Rheological properties for plasticized mPP-1 propylene homopolymer

| Plasticizer type | Plasticizer content (wt %) | $\eta_0$ (Pa·s) | λ (s) | n | MFR (g/10 min) |
|---|---|---|---|---|---|
| — | 0 | 830 | 0.012 | 0.190 | 25.54 |
| Rudol | 10 | 515 | 0.009 | 0.155 | 50.21 |
| Freezene 200 | 10 | 519 | 0.009 | 0.185 | 47.04 |
| SHF-403 | 5 | | | | |
| SHF-403 | 10 | 521 | 0.009 | 0.135 | |
| CORE 2500 | 10 | 527 | 0.009 | 0.137 | |
| VISOM 6 | 10 | | | | |
| C-9900 | 10 | 515 | 0.009 | 0.173 | |

TABLE 16e

DSC properties for plasticized mPP-1 propylene homopolymer

| Plasticizer type | Plasticizer content (wt %) | T_m at onset, first heating (° C.) | T_m at peak, first heating (° C.) | ΔH_f, first heating (J/g) | T_c at onset (° C.) | T_c at peak (° C.) | T_m at onset, second heating (° C.) | T_m at peak, second heating (° C.) | ΔH_f, second heating (J/g) |
|---|---|---|---|---|---|---|---|---|---|
| — | 0 |  | 151.4 | 79.1 | 109.1 | 104.2 |  | 149.5 | 89.2 |
| Rudol | 10 | 133.0 | 149.6 | 70.2 | 107.1 | 102.6 | 138.7 | 105.9 | 77.5 |
| Freezene 200 | 10 | 133.3 | 149.4 | 73.7 | 107.4 | 104.0 | 138.6 | 147.5 | 85.2 |
| SHF-403 | 5 |  |  |  |  |  |  |  |  |
| SHF-403 | 10 | 135.9 | 151.3 | 74.7 | 108.6 | 103.5 | 139.9 | 149.2 | 82.6 |
| CORE 2500 | 10 | 134.8 | 151.4 | 74.5 | 107.1 | 101.2 | 139.3 | 147.4 | 78.3 |
| VISOM 6 | 10 |  |  |  |  |  |  |  |  |
| C-9900 | 10 |  |  |  |  |  |  |  |  |

TABLE 16f

DMTA properties for plasticized mPP-1 propylene homopolymer

| Plasticizer type | Plasticizer content (wt %) | T_g at onset (° C.) | T_g at peak (° C.) | Peak Area | E' before T_g (MPa) | E' at 25° C. (MPa) |
|---|---|---|---|---|---|---|
| — | 0 | −15.4 | 5.6 | 0.19 | 2179 | 807 |
| Rudol | 10 | −46.2 | −7.9 | 0.62 | 3894 | 898 |
| Freezene 200 | 10 | −36.3 | −5.2 | 0.64 | 3497 | 571 |
| SHF-403 | 5 |  |  |  |  |  |
| SHF-403 | 10 | −42.0 | −6.8 | 0.47 | 2884 | 702 |
| CORE 2500 | 10 | −68.0 | −51.7 | 0.07 | 3472 | 601 |
| VISOM 6 | 10 |  |  |  |  |  |
| C-9900 | 10 | −41.1 | −8.8 | 0.71 | 3139 | 673 |

TABLE 17a

Tensile modulus and yield properties for plasticized RCP-2 propylene random copolymer

| Plasticizer type | Plasticizer content (wt %) | Young's Modulus (kpsi) | Yield Stress (psi) | Yield Strain (%) | Energy to Yield (ft-lbf) |
|---|---|---|---|---|---|
| — | 0 | 75.2 | 3997 | 17.0 | 23.0 |
| Rudol | 10 | 39.8 | 3126 | 26.5 | 27.6 |
| ParaLux 6001R | 10 | 45.8 | 3156 | 26.0 | 27.8 |
| SuperSyn 2150 | 10 | 49.6 | 3192 | 24.7 | 27.0 |
| EHC 110 | 10 | 41.1 | 3129 | 26.5 | 27.9 |
| VISOM 6 | 10 | 38.5 | 3114 | 26.7 | 27.8 |
| GTL14/HBS | 10 | 43.6 | 3160 | 26.5 | 28.2 |

TABLE 17b

Tensile break properties for plasticized RCP-2 propylene random copolymer

| Plasticizer type | Plasticizer content (wt %) | Break stress (psi) | Break Strain (%) | Energy to Break (ft-lbf) |
|---|---|---|---|---|
| — | 0 | 4422 | 710 | 82.0 |
| Rudol | 10 | 4883 | 1057 | 127.1 |
| ParaLux 6001R | 10 | 3919 | 763 | 79.4 |
| SuperSyn 2150 | 10 | 4568 | 1006 | 116.7 |
| EHC 110 | 10 | 4793 | 1039 | 123.8 |
| VISOM 6 | 10 | 4751 | 1096 | 128.8 |
| GTL14/HBS | 10 | 4865 | 1052 | 127.4 |

TABLE 17c

Flexure and Notched Izod impact properties for plasticized RCP-2 propylene random copolymer

| Plasticizer type | Plasticizer content (wt %) | 1% Secant Modulus (kpsi) | 2% Secant Modulus (kpsi) | −18° C. RNI* impact resistance (ft-lb/in) |
|---|---|---|---|---|
| — | 0 | 121.2 | 109.7 | 3.0 |
| Rudol | 10 | 67.8 | 60.2 | 26.2 |
| ParaLux 6001R | 10 | 75.2 | 66.8 | 20.9 |
| SuperSyn 2150 | 10 | 82.6 | 72.4 | 16.2 |
| EHC 110 | 10 | 70.4 | 62.6 | 21.6 |
| VISOM 6 | 10 | 71.8 | 63.6 | 30.0** |
| GTL14/HBS | 10 | 76.6 | 67.3 | 27.2 |

*Results were obtained using the Reversed Notched Izod testing protocol (ASTM D256E).
**Some RNI failures were incomplete breaks.

TABLE 17d

Rheological properties for plasticized RCP-2 propylene random copolymer

| Plasticizer type | Plasticizer content (wt %) | η_0 (Pa·s) | λ (s) | n | MFR (g/10 min) |
|---|---|---|---|---|---|
| — | 0 | 4467 | 0.120 | 0.297 | 7.20 |
| Rudol | 10 | 2605 | 0.124 | 0.352 |  |
| ParaLux 6001R | 10 |  |  |  | 19.30 |
| SuperSyn 2150 | 10 | 2752 | 0.125 | 0.345 | 15.38 |
| EHC 110 | 10 |  |  |  |  |
| VISOM 6 | 10 | 2514 | 0.114 | 0.345 | 16.59 |
| GTL14/HBS | 10 |  |  |  |  |

TABLE 17e

DSC properties for plasticized RCP-2 propylene random copolymer

| Plasticizer type | Plasticizer content (wt %) | $T_m$ at onset, first heating (° C.) | $T_m$ at peak, first heating (° C.) | $\Delta H_f$, first heating (J/g) | $T_c$ at onset (° C.) | $T_c$ at peak (° C.) | $T_m$ at onset, second heating (° C.) | $T_m$ at peak, second heating (° C.) | $\Delta H_f$, second heating (J/g) |
|---|---|---|---|---|---|---|---|---|---|
| — | 0 | | 149.7 | 67.9 | 104.1 | 99.2 | | 146.2 | 77.9 |
| Rudol | 10 | 122.0 | 147.0 | 65.2 | 101.7 | 95.2 | 130.1 | 141.2 | 61.5 |
| ParaLux 6001R | 10 | | | | | | | | |
| SuperSyn 2150 | 10 | 127.1 | 149.3 | 70.8 | 104.9 | 97.4 | 133.2 | 143.4 | 69.7 |
| EHC 110 | 10 | 123.7 | 148.2 | 67.2 | 101.4 | 94.8 | 130.6 | 144.3 | 64.3 |
| VISOM 6 | 10 | 125.1 | 148.6 | 65.1 | 101.3 | 94.5 | 130.3 | 144.8 | 65.6 |
| GTL14/HBS | 10 | | | | | | | | |

TABLE 17f

DMTA properties for plasticized RCP-2 propylene random copolymer

| Plasticizer type | Plasticizer content (wt %) | $T_g$ at onset (° C.) | $T_g$ at peak (° C.) | Peak Area | E' before $T_g$ (MPa) | E' at 25° C. (MPa) |
|---|---|---|---|---|---|---|
| — | 0 | −19.8 | −1.9 | 0.39 | 3344 | 1038 |
| Rudol | 10 | −48.8 | −10.0 | 1.03 | 3992 | 600 |
| ParaLux 6001R | 10 | −48.0 | −11.5 | 0.87 | 3263 | 472 |
| SuperSyn 2150 | 10 | −39.7 | −6.7 | 0.70 | 3086 | 510 |
| EHC 110 | 10 | −46.4 | −9.8 | 0.91 | 3503 | 464 |
| VISOM 6 | 10 | −59.5 | −15.7 | 0.83 | 3425 | 481 |
| GTL14/HBS | 10 | | | | | |

TABLE 18a

Tensile modulus and yield properties for plasticized EP-1 propylene-ethylene copolymer

| Plasticizer type | Plasticizer content (wt %) | Young's Modulus (kpsi) | Yield Stress * (psi) | Yield Strain * (%) |
|---|---|---|---|---|
| — | 0 | 4.23 | 564 | 24 |
| Rudol | 10 | 2.68 | 434 | 27 |
| SHF-101 | 10 | 2.78 | 442 | 27 |
| VHVI-8 | 10 | 2.74 | 449 | 28 |
| TPC 137 | 10 | 2.78 | 456 | 28 |
| Lucant HC-10 | 10 | 2.50 | 453 | 30 |
| C-9900 | 10 | 2.82 | 444 | 27 |

* Compression-molded test specimens; yield determined using 10% off-set definition.

TABLE 18b

Tensile break properties for plasticized EP-1 propylene-ethylene copolymer

| Plasticizer type | Plasticizer content (wt %) | Break stress (psi) | Break Strain (%) | Energy to Break (ft-lbf) |
|---|---|---|---|---|
| — | 0 | 2896 | 1791 | 94.5 |
| Rudol | 10 | * | * | * |
| SHF-101 | 10 | * | * | * |
| VHVI-8 | 10 | 2679 | 1930 | 88.8 |
| TPC 137 | 10 | * | * | * |
| Lucant HC-10 | 10 | 2947 | 1883 | 87.7 |
| C-9900 | 10 | 2865 | 1861 | 85.2 |

* Majority of specimens did not break before maximum strain limit reached.

TABLE 18c

Flexure properties for plasticized EP-1 propylene-ethylene copolymer

| Plasticizer type | Plasticizer content (wt %) | 1% Secant Modulus (kpsi) | 2% Secant Modulus (kpsi) |
|---|---|---|---|
| — | 0 | 5.854 | 5.816 |
| Rudol | 10 | 4.598 | 4.456 |
| SHF-101 | 10 | 4.668 | 4.448 |
| VHVI-8 | 10 | 4.895 | 4.786 |
| TPC 137 | 10 | 4.579 | 4.439 |
| Lucant HC-10 | 10 | 4.615 | 4.506 |
| C-9900 | 10 | 4.568 | 4.437 |

TABLE 18d

Rheological properties plasticized EP-1 propylene-ethylene copolymer

| Plasticizer type | Plasticizer content (wt %) | $\eta_0$ (Pa · s) | $\lambda$ (s) | n | MFR (g/10 min) |
|---|---|---|---|---|---|
| — | 0 | 2032 | 0.022 | 0.252 | |
| Rudol | 10 | | | | |
| SHF-101 | 10 | | | | |
| VHVI-8 | 10 | | | | |
| TPC 137 | 10 | | | | |
| Lucant HC-10 | 10 | | | | |
| C-9900 | 10 | | | | |

TABLE 18e

DSC properties for plasticized EP-1 propylene-ethylene copolymer

| Plasticizer type | Plasticizer content (wt %) | $T_m$ at onset, first heating (° C.) | $T_m$ at peak, first heating (° C.) | $\Delta H_f$, first heating (J/g) | $T_c$ at onset (° C.) | $T_c$ at peak (° C.) | $T_m$ at onset, second heating (° C.) | $T_m$ at peak, second heating (° C.) | $\Delta H_f$, second heating (J/g) |
|---|---|---|---|---|---|---|---|---|---|
| — | 0 | 41.8 | 55.6 | 34.3 | 22.6 | 8.3 | 33.7 | 61.4 | 20.9 |
| Rudol | 10 | 40.5 | 51.8 | 25.5 | 29.8 | 22.0 | 41.2 | 50.8, 67.2 | 19.2 |
| SHF-101 | 10 | 38.3 | 51.4 | 29.0 | 32.2 | 25.1 | 48.6 | 57.8, 67.0 | 18.3 |
| VHVI-8 | 10 | | | | | | | | |
| TPC 137 | 10 | | | | | | | | |
| Lucant HC-10 | 10 | | | | | | | | |
| C-9900 | 10 | | | | | | | | |

TABLE 18f

DMTA properties for plasticized EP-1 propylene-ethylene copolymer

| Plasticizer type | Plasticizer Content (wt %) | $T_g$ at onset (° C.) | $T_g$ at peak (° C.) | Peak Area | E' before $T_g$ (MPa) | E' at 25° C. (MPa) |
|---|---|---|---|---|---|---|
| — | 0 | −24.5* | | | | |
| Rudol | 10 | −35.5 | −21.8 | 3.7 | 2515 | 16.1 |
| SHF-101 | 10 | −38.2 | −22.5 | 4.3 | 3196 | 18.7 |
| VHVI-8 | 10 | −38.3 | −22.1 | 4.4 | 3307 | 36.1 |
| TPC 137 | 10 | −38.0 | −23.1 | 3.2 | 3028 | 26.9 |
| Lucant HC-10 | 10 | | | | | |
| C-9900 | 10 | | | | | |

*As measured by DSC.

TABLE 19a

Tensile modulus and yield properties for plasticized EP-2 propylene-ethylene copolymer

| Plasticizer type | Plasticizer content (wt %) | Young's Modulus (kpsi) | Yield Stress * (psi) | Yield Strain * (%) |
|---|---|---|---|---|
| — | 0 | 1.457 | 246 | 28 |
| Rudol | 10 | 0.846 | 128 | 28 |
| Freezene 200 | 10 | 1.043 | 181 | 29 |
| SHF-403 | 10 | 0.886 | 143 | 27 |
| IsoPar V | 10 | 0.793 | 124 | 27 |
| Exxsol D130 | 10 | 0.833 | 125 | 28 |
| GTL6/MBS | 10 | 1.092 | 189 | 28 |

* Compression-molded test specimens; yield determined using 10% off-set definition.

TABLE 19b

Tensile break properties for plasticized EP-2 propylene-ethylene copolymer

| Plasticizer type | Plasticizer content (wt %) | Break stress (psi) | Break Strain (%) | Energy to Break (ft-lbf) |
|---|---|---|---|---|
| — | 0 | * | * | * |
| Rudol | 10 | * | * | * |
| Freezene 200 | 10 | * | * | * |
| SHF-403 | 10 | * | * | * |
| IsoPar V | 10 | * | * | * |
| Exxsol D130 | 10 | * | * | * |
| GTL6/MBS | 10 | * | * | * |

* Majority of specimens did not break before maximum strain limit reached.

TABLE 19c

Flexure properties for plasticized EP-2 propylene-ethylene copolymer

| Plasticizer type | Plasticizer content (wt %) | 1% Secant Modulus (kpsi) | 2% Secant Modulus (kpsi) |
|---|---|---|---|
| — | 0 | 2.354 | 2.267 |
| Rudol | 10 | 1.856 | 1.791 |
| Freezene 200 | 10 | 2.032 | 1.920 |
| SHF-403 | 10 | 1.930 | 1.884 |
| IsoPar V | 10 | 1.521 | 1.502 |
| Exxsol D130 | 10 | 1.775 | 1.733 |
| GTL6/MBS | 10 | 1.942 | 1.858 |

TABLE 19d

Rheological properties for plasticized EP-2 propylene-ethylene copolymer

| Plasticizer type | Plasticizer content (wt %) | $\eta_0$ (Pa · s) | $\lambda$ (s) | n | MFR (g/10 min) |
|---|---|---|---|---|---|
| — | 0 | 1167 | 0.011 | 0.194 | |
| Rudol | 10 | | | | |
| Freezene 200 | 10 | | | | |
| SHF-403 | 10 | | | | |
| IsoPar V | 10 | | | | |
| Exxsol D130 | 10 | | | | |
| GTL6/MBS | 10 | | | | |

TABLE 19e

DSC properties for plasticized EP-2 propylene-ethylene copolymer

| Plasticizer type | Plasticizer content (wt %) | $T_m$ at onset, first heating (° C.) | $T_m$ at peak, first heating (° C.) | $\Delta H_f$, first heating (J/g) | $T_c$ at onset (° C.) | $T_c$ at peak (° C.) | $T_m$ at onset, second heating (° C.) | $T_m$ at peak, second heating (° C.) | $\Delta H_f$, second heating (J/g) |
|---|---|---|---|---|---|---|---|---|---|
| — | 0 | 39.7 | 47.0 | 13.4 | — | — | — | — | — |
| Rudol | 10 | 40.2 | 50.8 | 10.1 | — | — | 44.7 | 56.2 | 3.5 |
| Freezene 200 | 10 | | | | | | | | |
| SHF-403 | 10 | 39.0 | 49.7 | 14.2 | — | — | 44.4 | 54.3 | 4.9 |
| IsoPar V | 10 | | | | | | | | |
| Exxsol D130 | 10 | 42.1 | 49.5 | 10.2 | — | — | — | — | — |
| GTL6/MBS | 10 | | | | | | | | |

TABLE 20a

Tensile modulus and yield properties for plasticized sPP propylene homopolymer

| Plasticizer type | Plasticizer content (wt %) | Young's Modulus (kpsi) | Yield Stress (psi) | Yield Strain (%) | Energy to Yield (ft-lbf) |
|---|---|---|---|---|---|
| — | 0 | 36.7 | 2481 | 21.7 | 17.7 |
| Rudol | 10 | 21.9 | 1991 | 31.5 | 20.7 |
| IsoPar V | 10 | 23.3 | 2057 | 28.9 | 19.5 |
| VHVI-8 | 10 | 22.9 | 2047 | 32.9 | 22.6 |

TABLE 20b

Tensile break properties for plasticized sPP propylene homopolymer

| Plasticizer type | Plasticizer content (wt %) | Break stress (psi) | Break Strain (%) | Energy to Break (ft-lbf) |
|---|---|---|---|---|
| — | 0 | 2321 | 254 | 19.8 |
| Rudol | 10 | 2288 | 338 | 23.3 |
| IsoPar V | 10 | 2260 | 341 | 23.7 |
| VHVI-8 | 10 | 2347 | 355 | 25.1 |

TABLE 20c

Flexure and Notched Izod impact properties for plasticized sPP propylene homopolymer

| Plasticizer type | Plasticizer content (wt %) | 1% Secant Modulus (kpsi) | 2% Secant Modulus (kpsi) | −18° C. RNI* impact resistance (ft-lb/in) |
|---|---|---|---|---|
| — | 0 | 64.2 | 60.8 | 3.4 |
| Rudol | 10 | 39.5 | 37.3 | 5.0 |
| IsoPar V | 10 | 41.8 | 39.4 | 4.8 |
| VHVI-8 | 10 | 41.7 | 39.1 | 31.9** |

*Results were obtained using the Reversed Notched Izod testing protocol (ASTM D256E).
**All RNI specimens did not break.

TABLE 20d

Rheological properties for plasticized sPP propylene homopolymer

| Plasticizer type | Plasticizer content (wt %) | $\eta_0$ (Pa · s) | $\lambda$ (s) | n | MFR (g/10 min) |
|---|---|---|---|---|---|
| — | 0 | 12431 | 0.179 | 0.307 | |
| Rudol | 10 | 6823 | 0.136 | 0.328 | |
| IsoPar V | 10 | 7445 | 0.143 | 0.325 | |
| VHVI-8 | 10 | 6652 | 0.131 | 0.327 | |

TABLE 20e

DSC properties for plasticized sPP propylene homopolymer

| Plasticizer type | Plasticizer content (wt %) | $T_m$ at onset, first heating (° C.) | $T_m$ at peak, first heating (° C.) | $\Delta H_f$, first heating (J/g) | $T_c$ at onset (° C.) | $T_c$ at peak (° C.) | $T_m$ at onset, second heating (° C.) | $T_m$ at peak, second heating (° C.) | $\Delta H_f$, second heating (J/g) |
|---|---|---|---|---|---|---|---|---|---|
| — | 0 | 116.9 | 128.9 | 39.0 | 81.9 | 70.7 | — | — | — |
| Rudol | 10 | | | | | | | | |
| IsoPar V | 10 | | | | | | | | |
| VHVI-8 | 10 | 114.0 | 127.0 | 34.2 | 80.8 | 72.2 | 116.1 | 127.5 | 33.9 |

TABLE 20f

DMTA properties for plasticized sPP propylene homopolymer

| Plasticizer type | Plasticizer content (wt %) | T$_g$ at onset (° C.) | T$_g$ at peak (° C.) | Peak Area | E' before T$_g$ (MPa) | E' at 25° C. (MPa) |
|---|---|---|---|---|---|---|
| — | 0 | −4.8 | 8.4 | 1 | 2717 | 434 |
| Rudol | 10 | −31.6 | −6.7 | 1.8 | 3637 | 360 |
| IsoPar V | 10 | −26.9 | −4.8 | 1.5 | 3462 | 373 |
| VHVI-8 | 10 | −35.5 | −4.8 | 1.53 | 3141 | 221 |

TABLE 21a

Tensile modulus and yield properties for plasticized ICP-2 propylene impact copolymer

| Plasticizer type | Plasticizer content (wt %) | Young's Modulus (kpsi) | Yield Stress (psi) | Yield Strain (%) | Energy to Yield (ft-lbf) |
|---|---|---|---|---|---|
| — | 0 | 99.2 | 3766 | 10.7 | 13.3 |
| Rudol | 10 | 54.9 | 2985 | 23.0 | 23.9 |
| ParaLux 6001R | 10 | 57.5 | 3022 | 21.8 | 22.9 |
| SHF-101 | 10 | 61.3 | 3076 | 22.2 | 23.9 |
| Exxsol D130 | 10 | 43.9 | 2950 | 25.2 | 25.7 |
| EHC 110 | 10 | 60.1 | 3096 | 22.4 | 24.1 |
| TPC 137 | 10 | 54.0 | 2959 | 23.0 | 23.8 |

TABLE 21b

Tensile break properties for plasticized ICP-2 propylene impact copolymer

| Plasticizer type | Plasticizer content (wt %) | Break stress (psi) | Break Strain (%) | Energy to Break (ft-lbf) |
|---|---|---|---|---|
| — | 0 | 2221 | 394 | 38.8 |
| Rudol | 10 | 3430 | 763 | 76.0 |
| ParaLux 6001R | 10 | 3236 | 777 | 77.6 |
| SHF-101 | 10 | 3572 | 774 | 78.9 |
| Exxsol D130 | 10 | 4020 | 1063 | 117.2 |
| EHC 110 | 10 | 3474 | 681 | 68.2 |
| TPC 137 | 10 | 3124 | 776 | 76.3 |

TABLE 21c

Flexure and Notched Izod impact properties for plasticized ICP-2 propylene impact copolymer

| Plasticizer type | Plasticizer content (wt %) | 1% Secant Modulus (kpsi) | 2% Secant Modulus (kpsi) | −18° C. NI impact resistance (ft-lb/in) |
|---|---|---|---|---|
| — | 0 | 144.1 | 129.7 | 1.1 |
| Rudol | 10 | 83.8 | 73.8 | 1.3 |
| ParaLux 6001R | 10 | 86.8 | 76.7 | 1.3 |
| SHF-101 | 10 | 96.1 | 82.6 | 1.3 |
| Exxsol D130 | 10 | 82.9 | 72.4 | 1.7 |
| EHC 110 | 10 | 92.6 | 80.1 | 1.3 |
| TPC 137 | 10 | 88.8 | 77.9 | 1.5 |

TABLE 21d

Rheological properties for plasticized ICP-2 propylene impact copolymer

| Plasticizer type | Plasticizer content (wt %) | η$_0$ (Pa · s) | λ (s) | n | MFR (g/10 min) |
|---|---|---|---|---|---|
| — | 0 | 4218 | 0.182 | 0.368 | 8.164 |
| Rudol | 10 | 2663 | 0.142 | 0.370 | 22.26 |
| ParaLux 6001R | 10 | | | | 30.95 |
| SHF-101 | 10 | | | | |
| Exxsol D130 | 10 | 2765 | 0.152 | 0.375 | |
| EHC 110 | 10 | 2745 | 0.144 | 0.367 | 18.89 |
| TPC 137 | 10 | 2438 | 0.110 | 0.359 | 27.11 |

TABLE 21e

DSC properties for plasticized ICP-2 propylene impact copolymer

| Plasticizer type | Plasticizer content (wt %) | T$_m$ at onset, first heating (° C.) | T$_m$ at peak, first heating (° C.) | ΔH$_f$, first heating (J/g) | T$_c$ at onset (° C.) | T$_c$ at peak (° C.) | T$_m$ at onset, second heating (° C.) | T$_m$ at peak, second heating (° C.) | ΔH$_f$, second heating (J/g) |
|---|---|---|---|---|---|---|---|---|---|
| — | 0 | | 166.6 | 76.9 | 114.8 | 111.3 | | 163.2 | 85.6 |
| Rudol | 10 | 149.4 | 163.4 | 72.8 | 114.7 | 108.1 | 151.3 | 158.7 | 76.7 |
| ParaLux 6001R | 10 | 149.2 | 165.1 | 73.1 | 113.2 | 106.1 | 150.4 | 163.6 | 74.6 |
| SHF-101 | 10 | | | | | | | | |
| Exxsol D130 | 10 | | | | | | | | |
| EHC 110 | 10 | 149.0 | 165.2 | 72.4 | 115.8 | 107 | 151.5 | 163.9 | 76.5 |
| TPC 137 | 10 | 149.5 | 166.0 | 72.0 | 116.2 | 106.5 | 152.3 | 164.2 | 76.4 |

TABLE 21f

DMTA properties for plasticized ICP-2 propylene impact copolymer

| Plasticizer type | Plasticizer content (wt %) | Lower $T_g$ at onset (° C.) | Lower $T_g$ at peak (° C.) | Lower Peak Area | Upper $T_g$ at onset (° C.) | Upper $T_g$ at peak (° C.) | Upper Peak Area | E' before $T_g$ (MPa) | E' at 25° C. (MPa) |
|---|---|---|---|---|---|---|---|---|---|
| — | 0 | −56.4 | −50.2 | 0.06 | −24.5 | 2.9 | 0.20 | 2269 | 557 |
| Rudol | 10 | −63.5 | −53.0 | 0.08 | −41.5 | −7.7 | 0.50 | 2854 | 514 |
| ParaLux 6001R | 10 | −57.9 | −50.8 | 0.07 | −39.2 | −7.2 | 0.43 | 3425 | 689 |
| SHF-101 | 10 | | | | | | | | |
| Exxsol D130 | 10 | −71.6 | −59.8 | 0.19 | −34.2 | −10.5 | 0.25 | 3515 | 558 |
| EHC 110 | 10 | −60.0 | −50.6 | 0.07 | −37.0 | −9.0 | 0.43 | 3116 | 589 |
| TPC 137 | 10 | −71.4 | −59.7 | 0.11 | −43.4 | −13.0 | 0.40 | 3065 | 579 |

TABLE 22a

Tensile modulus and yield properties for plasticized ICP-3 propylene impact copolymer

| Plasticizer type | Plasticizer content (wt %) | Young's Modulus (kpsi) | Yield Stress (psi) | Yield Strain (%) | Energy to Yield (ft-lbf) |
|---|---|---|---|---|---|
| — | 0 | 123.5 | 4151 | 8.5 | 11.1 |
| ParaLux 6001R | 10 | 68.2 | 3199 | 22.3 | 25.5 |
| SuperSyn 2150 | 10 | 76.4 | 3319 | 17.0 | 19.6 |
| Norpar 15 | 10 | 62.2 | 3236 | 24.5 | 27.7 |
| GTL6/MBS | 10 | 61.6 | 3207 | 26.1 | 29.7 |
| Lucant HC-10 | 10 | 65.4 | 3153 | 24.8 | 27.8 |

TABLE 22b

Tensile break properties for plasticized ICP-3 propylene impact copolymer

| Plasticizer type | Plasticizer content (wt %) | Break stress (psi) | Break Strain (%) | Energy to Break (ft-lbf) |
|---|---|---|---|---|
| — | 0 | 2894 | 88 | 10.3 |
| ParaLux 6001R | 10 | 2578 | 614 | 60.3 |
| SuperSyn 2150 | 10 | 2903 | 588 | 59.2 |
| Norpar 15 | 10 | 3049 | 584 | 58.1 |
| GTL6/MBS | 10 | 3079 | 558 | 56.0 |
| Lucant HC-10 | 10 | 3043 | 567 | 55.8 |

TABLE 22c

Flexure and Notched Izod impact properties for plasticized ICP-3 propylene impact copolymer

| Plasticizer type | Plasticizer content (wt %) | 1% Secant Modulus (kpsi) | 2% Secant Modulus (kpsi) | −18° C. NI impact resistance (ft-lb/in) |
|---|---|---|---|---|
| — | 0 | 193.3 | 168.7 | 1.1 |
| ParaLux 6001R | 10 | 100.5 | 87.7 | 1.5 |
| SuperSyn 2150 | 10 | 120.3 | 102.2 | 1.3 |
| Norpar 15 | 10 | 101.5 | 87.9 | 2.3 |
| GTL6/MBS | 10 | 103.2 | 87.9 | 1.8 |
| Lucant HC-10 | 10 | 102.5 | 87.7 | 1.6 |

TABLE 22d

Rheological properties for plasticized ICP-3 propylene impact copolymer

| Plasticizer type | Plasticizer content (wt %) | $\eta_0$ (Pa·s) | $\lambda$ (s) | n | MFR (g/10 min) |
|---|---|---|---|---|---|
| — | 0 | 4301 | 0.190 | 0.367 | 9.22 |
| ParaLux 6001R | 10 | 2455 | 0.129 | 0.354 | 18.77 |
| SuperSyn 2150 | 10 | | | | |
| Norpar 15 | 10 | 3151 | 0.161 | 0.378 | |
| GTL6/MBS | 10 | | | | |
| Lucant HC-10 | 10 | 2452 | 0.128 | 0.361 | |

TABLE 22e

DSC properties for plasticized ICP-3 propylene impact copolymer

| Plasticizer type | Plasticizer content (wt %) | $T_m$ at onset, first heating (° C.) | $T_m$ at peak, first heating (° C.) | $\Delta H_f$, first heating (J/g) | $T_c$ at onset (° C.) | $T_c$ at peak (° C.) | $T_m$ at onset, second heating (° C.) | $T_m$ at peak, second heating (° C.) | $\Delta H_f$, second heating (J/g) |
|---|---|---|---|---|---|---|---|---|---|
| — | 0 | | 166.5 | 80.2 | 131.0 | 127.3 | | 167.3 | 77.0 |
| ParaLux 6001R | 10 | 150.5 | 165.0 | 75.8 | 118.3 | 114.4 | 154.1 | 164.1 | 76.6 |

TABLE 22e-continued

DSC properties for plasticized ICP-3 propylene impact copolymer

| Plasticizer type | Plasticizer content (wt %) | $T_m$ at onset, first heating (°C.) | $T_m$ at peak, first heating (°C.) | $\Delta H_f$, first heating (J/g) | $T_c$ at onset (°C.) | $T_c$ at peak (°C.) | $T_m$ at onset, second heating (°C.) | $T_m$ at peak, second heating (°C.) | $\Delta H_f$, second heating (J/g) |
|---|---|---|---|---|---|---|---|---|---|
| SuperSyn 2150 | 10 | 153.2 | 166.0 | 76.9 | 122.1 | 84.4 | 156.1 | 165.5 | 80.7 |
| Norpar 15 | 10 | | | | | | | | |
| GTL6/MBS | 10 | | | | | | | | |
| Lucant HC-10 | 10 | | | | | | | | |

TABLE 22f

DMTA properties for plasticized ICP-3 propylene impact copolymer

| Plasticizer type | Plasticizer content (wt %) | Lower $T_g$ at onset (°C.) | Lower $T_g$ at peak (°C.) | Lower Peak Area | Upper $T_g$ at onset (°C.) | Upper $T_g$ at peak (°C.) | Upper Peak Area | E' before T (MPa) | E' at 25° C. (MPa) |
|---|---|---|---|---|---|---|---|---|---|
| — | 0 | −57.9 | −50.0 | | −13.2 | 4.1 | | 3369 | 768.4 |
| ParaLux 6001R | 10 | −59.3 | −52.4 | 0.09 | −35.2 | −4.6 | 0.42 | 3037 | 661.4 |
| SuperSyn 2150 | 10 | −58.5 | −49.9 | 0.06 | −35.3 | −3.0 | 0.14 | 3297 | 716.3 |
| Norpar 15 | 10 | −59.2 | −52.2 | 0.03 | −38.8 | −11.2 | 0.36 | 3545 | 591.0 |
| GTL6/MBS | 10 | | | | | | | | |
| Lucant HC-10 | 10 | −66.4 | −58.3 | 0.10 | −42.8 | −9.1 | 0.40 | 3168 | 661.0 |

TABLE 23a

Tensile modulus and yield properties for plasticized TPO propylene-based thermoplastic olefin

| Plasticizer type | Plasticizer content (wt %) | Young's Modulus (kpsi) | Yield Stress (psi) | Yield Strain (%) | Energy to Yield (ft-lbf) |
|---|---|---|---|---|---|
| — | 0 | 68.7 | 3187 | 14.0 | 15.1 |
| Rudol | 10 | 38.1 | 2240 | 26.5 | 21.1 |
| SHF-101 | 10 | 38.8 | 2189 | 25.2 | 19.9 |
| IsoPar V | 10 | 37.6 | 2304 | 26.5 | 21.4 |
| GTL14/HBS | 10 | 39.6 | 2232 | 28.4 | 23.1 |

TABLE 23b

Tensile break properties for plasticized TPO propylene-based thermoplastic olefin

| Plasticizer type | Plasticizer content (wt %) | Break stress (psi) | Break Strain (%) | Energy to Break (ft-lbf) |
|---|---|---|---|---|
| — | 0 | 5154 | 1051 | 116.0 |
| Rudol | 10 | 5165 | 1334 | 151.9 |
| SHF-101 | 10 | 4780 | 1218 | 129.2 |
| IsoPar V | 10 | 5021 | 1276 | 141.2 |
| GTL14/HBS | 10 | 5148 | 1342 | 154.6 |

TABLE 23c

Flexure and Notched Izod impact properties for plasticized TPO propylene-based thermoplastic olefin

| Plasticizer type | Plasticizer content (wt %) | 1% Secant Modulus (kpsi) | 2% Secant Modulus (kpsi) | −18° C. NI impact resistance (ft-lb/in) |
|---|---|---|---|---|
| — | 0 | 116.0 | 105.8 | 1.0 |
| Rudol | 10 | 62.9 | 56.2 | 0.9 |
| SHF-101 | 10 | 66.2 | 58.7 | 1.0 |
| IsoPar V | 10 | 61.5 | 55.1 | 1.1 |
| GTL14/HBS | 10 | 68.5 | 60.2 | 1.0 |

TABLE 23d

Rheological properties for plasticized TPO propylene-based thermoplastic olefin

| Plasticizer type | Plasticizer content (wt %) | $\eta_0$ (Pa·s) | $\lambda$ (s) | n | MFR (g/10 min) |
|---|---|---|---|---|---|
| — | 0 | 1675 | 0.014 | 0.207 | |
| Rudol | 10 | | | | |
| SHF-101 | 10 | | | | |
| IsoPar V | 10 | | | | |
| GTL14/HBS | 10 | | | | |

TABLE 23e

DSC properties for plasticized TPO propylene-based thermoplastic olefin

| Plasticizer type | Plasticizer content (wt %) | $T_m$ at onset, first heating (° C.) | $T_m$ at peak, first heating (° C.) | $\Delta H_f$, first heating (J/g) | $T_c$ at onset (° C.) | $T_c$ at peak (° C.) | $T_m$ at onset, second heating (° C.) | $T_m$ at peak, second heating (° C.) | $\Delta H_f$, second heating (J/g) |
|---|---|---|---|---|---|---|---|---|---|
| — | 0 | 138.2 | 151.8 | 58.4 | 109.8 | 103.7 | 142.5 | 150.1 | 64.0 |
| Rudol | 10 | | | | | | | | |
| SHF-101 | 10 | | | | | | | | |
| IsoPar V | 10 | | | | | | | | |
| GTL14/HBS | 10 | | | | | | | | |

TABLE 23f

DMTA properties for plasticized TPO propylene-based thermoplastic olefin

| Plasticizer type | Plasticizer content (wt %) | Lower $T_g$ at onset (° C.) | Lower $T_g$ at peak (° C.) | Lower Peak Area | Upper $T_g$ at onset (° C.) | Upper $T_g$ at peak (° C.) | Upper Peak Area | E' before $T_g$ (MPa) | E' at 25° C. (MPa) |
|---|---|---|---|---|---|---|---|---|---|
| — | 0 | −60.6 | −45.1 | 0.06 | −8.7 | 6.0 | 0.15 | 2867 | 782 |
| Rudol | 10 | −68.1 | −55.6 | 0.10 | −34.2 | −3.9 | 0.51 | 3169 | 425 |
| SHF-101 | 10 | −65.0 | 51.7 | 0.07 | −34.3 | −7.0 | 0.30 | 3472 | 601 |
| IsoPar V | 10 | −77.2 | −57.8 | 0.14 | −34.7 | −6.9 | 0.42 | 3657 | 609 |
| GTL14/HBS | 10 | | | | | | | | |

TABLE 24a

Tensile modulus and yield properties for plasticized PB 1-butene homopolymer

| Plasticizer type | Plasticizer content (wt %) | Young's Modulus (kpsi) | Yield Stress (psi) | Yield Strain (%) |
|---|---|---|---|---|
| — | 0 | 55.0 | * | * |
| Rudol | 10 | 25.8 | * | * |
| Norpar 15 | 10 | 26.3 | * | * |
| VISOM 6 | 10 | 23.7 | * | * |
| C-9900 | 10 | 26.8 | * | * |

* No yield before failure.

TABLE 24b

Tensile break properties for plasticized PB 1-butene homopolymer

| Plasticizer type | Plasticizer content (wt %) | Break stress (psi) | Break Strain (%) | Energy to Break (ft-lbf) |
|---|---|---|---|---|
| — | 0 | 5200 | 38 | 5.0 |
| Rudol | 10 | 3289 | 31 | 2.4 |
| Norpar 15 | 10 | 3349 | 31 | 2.5 |
| VISOM 6 | 10 | 3238 | 31 | 2.3 |
| C-9900 | 10 | 3139 | 25 | 1.8 |

TABLE 24c

Flexure and Notched Izod impact properties for plasticized PB 1-butene homopolymer

| Plasticizer type | Plasticizer content (wt %) | 1% Secant Modulus (kpsi) | 2% Secant Modulus (kpsi) | −18° C. RNI* impact resistance (ft-lb/in) |
|---|---|---|---|---|
| — | 0 | 79.7 | 74.0 | 17.7 |
| Rudol | 10 | 37.0 | 35.2 | 18.1** |
| Norpar 15 | 10 | 43.0 | 40.7 | 22.2** |
| VISOM 6 | 10 | 36.6 | 35.2 | 19.2** |
| C-9900 | 10 | 36.5 | 35.2 | 20.7** |

*Results were obtained using the Reversed Notched Izod testing protocol (ASTM D256E).

**Some NI failures were incomplete breaks.

TABLE 25a

Resin properties of plasticized mPP-2 propylene homopolymer

| | wt % PAO | Tm peak (° C.) | Tm onset (° C.) | ΔHm (J/g) | Tc peak (° C.) | Tc onset (° C.) | ΔHc (J/g) | Tg peak (° C.) |
|---|---|---|---|---|---|---|---|---|
| Control | 0 | 152.8 | 142.2 | 109.6 | 123.8 | 127.2 | 106.0 | 3.5 |
| SHF61 | 3 | 151.8 | 142.5 | 105.9 | 123.6 | 127.1 | 104.3 | |
| SHF61 | 5 | 151.5 | 142.3 | 102.8 | 122.6 | 126.1 | 100.9 | |
| SHF61 | 10 | 149.7 | 140.9 | 100.4 | 120.8 | 124.4 | 95.6 | |
| SHF101 | 3 | 151.9 | 142.8 | 104.1 | 123.5 | 127.0 | 103.1 | −0.4 |
| SHF101 | 5 | 151.5 | 142.6 | 102.2 | 123.0 | 126.6 | 100.4 | −2.3 |
| SHF101 | 10 | 150.3 | 140.9 | 99.5 | 120.8 | 124.3 | 100.3 | −6.4 |
| SHF401 | 3 | 152.2 | 142.7 | 104.3 | 123.5 | 126.9 | 106.3 | |
| SHF401 | 5 | 151.7 | 142.1 | 102.6 | 122.8 | 126.4 | 100.8 | |
| SHF401 | 10 | 151.0 | 142.2 | 97.8 | 121.8 | 125.5 | 98.8 | |
| SuperSyn 2150 | 3 | 152.2 | 142.2 | 103.1 | 123.3 | 126.7 | 105.2 | |
| SuperSyn 2150 | 5 | 151.9 | 143.0 | 101.3 | 123 | 126.5 | 99.2 | |
| SuperSyn 2150 | 10 | 151.4 | 142.1 | 96.0 | 121.8 | 125.3 | 98.7 | |

TABLE 25b

Molded part properties of plasticized mPP-2 propylene homopolymer

| | wt % PAO | MFR | Tensile strength (kpsi) | Elongation to yield (%) | Flex 1% secant (kpsi) | HDT (° C.) | Gardner RT (in-lbs) | NI RT (ft-lb/in) | RNI −18° C. (ft-lb/in) |
|---|---|---|---|---|---|---|---|---|---|
| Control | 0 | 16.6 | 5.20 | 8.6 | 230 | 107.8 | 22 | 1.02 | 2.45 |
| SHF61 | 3 | 19.7 | 4.86 | 12.4 | 187 | 107.5 | 194 | 1.27 | 2.63 |
| SHF61 | 5 | 22.5 | 4.40 | 15.0 | 161 | 99.8 | 189 | 0.80 | 6.04 |
| SHF61 | 10 | 28.1 | 3.89 | 16.6 | 133 | 98.9 | 206 | 0.92 | 11.30 |
| SHF101 | 3 | 19.5 | 4.73 | 12.8 | 188 | 104.1 | 167 | 0.68 | 2.75 |
| SHF101 | 5 | 20.9 | 4.46 | 13.9 | 174 | 105.7 | 209 | 0.72 | 3.19 |
| SHF101 | 10 | 26.7 | 3.85 | 16.5 | 140 | 95.7 | 251 | 0.91 | 8.99 |
| SHF401 | 3 | 19.3 | 4.68 | 11.7 | 199 | 104.7 | 157 | 0.57 | 2.27 |
| SHF401 | 5 | 21.4 | 4.39 | 12.7 | 182 | 100.6 | 186 | 0.62 | 2.84 |
| SHF401 | 10 | 26.8 | 3.96 | 14.9 | 153 | 96.9 | 192 | 0.83 | 5.62 |
| SuperSyn 2150 | 3 | 19.2 | 4.78 | 10.5 | 205 | 101.4 | 153 | 0.49 | 2.63 |
| SuperSyn 2150 | 5 | 21.6 | 4.53 | 12.1 | 190 | 104.3 | 182 | 0.64 | 2.78 |
| SuperSyn 2150 | 10 | 23.4 | 3.99 | 13.4 | 157 | 92.8 | 214 | 0.70 | 6.48 |

TABLE 26

Molded part properties of plasticized propylene random copolymers

| | RCP-3 | | RCP-4 | | |
|---|---|---|---|---|---|
| Properties | no NFP (control) | 25 wt % Exact® 3035 | no NFP (control) | 5 wt % Isopar V | 5 wt % SHF-101 |
| Tensile strength @ yield (psi) | 4.7 | 3.2 | 4.2 | 4.0 | 4.0 |
| Elongation @ yield (%) | 12 | 16.7 | 13.4 | 16.7 | 17.2 |
| Flex modulus 1% secant (kpsi) | 167 | 102 | 146 | 108 | 116 |
| HDT @ 66 psi (° C.) | 84 | 70 | 78 | 73 | 72 |
| Gardner impact @ 23° C. (in-lbs) | 273 | 210 | 242 | 226 | 226 |
| Notched Izod impact @ 23° C. (ft-lbs/in) | 1.1 | 10.3 | 1.4 | 4.5 | 3.8 |
| Haze (%) | — | — | 9.9 | 8.6 | 10.2 |

RCP-3 contains 800 ppm CaSt, 800 ppm Ultanox626A, 500 ppm Tinuvin 622, 2500 ppm Millad 3940
RCP-4 contains 400 ppm CaSt, 400 ppm Irganox 3114, 400 ppm Ultanox626A, 1500 ppm Millad 3940, 800 ppm Atmer 129
Exact® 3035 is a metallocene ethylene-butene copolymer (3.5 MI, 0.90 g/cm3 density)

TABLE 27

Comparison of permanence of NFP in RCP-2 propylene random copolymer.

| | | % weight loss over time period | | | | |
|---|---|---|---|---|---|---|
| Blend composition | plasticizer KV at 100° C. | 24 hr | 48 hr | 139 hr | 167 hr | 311 hr |
| PP | — | 0.3 | 0.3 | 0.3 | 0.3 | 0.3 |
| PP + 10% SHF-21 | 2 | 7.7 | 8.1 | 8.1 | 8.0 | 8.0 |
| PP + 10% SHF-41 | 4 | 0.2 | 0.7 | 1.1 | 1.3 | 2.0 |
| PP + 10% SHF-61 | 6 | 0.2 | 0.4 | 0.6 | 0.6 | 0.9 |
| PP + 10% SHF-82 | 8 | 0.1 | 0.2 | 0.3 | 0.3 | 0.5 |
| PP + 10% SHF-101 | 10 | −0.1 | 0.2 | 0.2 | 0.1 | 0.3 |
| PP + 10% Rudol | 5 | — | — | — | — | 5.4 |

TABLE 28

NFP content in polypropylene/NFP blends.

| Polymer | NFP | Blend Method | Dry blend composition (wt % NFP) | extraction method (wt % NFP) | CRYSTAF method (wt % NFP) |
|---|---|---|---|---|---|
| Achieve™ 1654 | SHF-101 | Extruder | 3 | 2.6 | 2.2 ± 0.1[a] |
| | | | 5 | 4.5 | 4.2 ± 0.1[a] |
| | | | 10 | 7.4 | 7.6 ± 0.1[a] |
| | | | 20 | 15.4 | 15.2 ± 0.5[a] |
| PP 3155 | SuperSyn 2150 | Extruder | 3 | 2.5[b] | 3.5 |
| | | | 6 | 5.5[b] | 6.5 |
| PP 1024 | SHF-101 | Brabender | 5 | — | 5.9 |
| | | | 10 | — | 10.3 |
| | | | 20 | — | 21.1 |
| PP 1024 | Isopar V | Brabender | 5 | — | 3.9 |
| | | | 10 | — | 8.3 |
| PP 7033N | SuperSyn 2150 | Brabender | 10 | 9.9 | — |
| | Norpar 15 | Brabender | 10 | 6.5 | — |
| | GTL6/MBS | Brabender | 10 | 9.4 | 10.1 |

[a] Average and standard deviation reported for results from triplicate CRYSTAF runs.
[b] 12 hour reflux.

TABLE 29

Softness of 25 gsm spunbond fabrics made of plasticized mPP-1

| | none | Isopar V | SHF-101 | SHF-403 | SuperSyn 2150 |
|---|---|---|---|---|---|
| Concentration of fluid (%) | 0 | 4 | 4 | 4 | 4 |
| Fabric Properties | | | | | |
| Peak Load (lbs) MD/TD | 9.4/4.8 | 8.0/4.4 | 7.8/4.1 | 8.3/4.1 | 7.5/3.9 |
| Elongation @ Break (%) MD/TD | 76/77 | 65/76 | 58/67 | 72/73 | 64/73 |
| Elmendorf Tear (g/basis weight) TD | 17 | 19 | 15 | 18 | 20 |
| Total Hand (grams) | 31 | 32 | 24 | 21 | 15 |

TABLE 30

Softness of 34 gsm spunbond fabrics made of plasticized znPP-2

|  | Neat | SHF-101 | SHF-101 | SHF-403 | SHF-1003 |
|---|---|---|---|---|---|
| Concentration of fluid (%) | 0 | 3 | 5 | 5 | 5 |
| Softness Total Hand (grams) | | | | | |
| 0.2 gram/hole/minute | 42.5 | 31.0 | 24.7 | 24.4 | 28.8 |
| 0.3 gram/hole/minute | 49.8 | 33.4 | 28.9 | 28.5 | 29.6 |
| 0.4 gram/hole/minute | 41.4 | 32.9 | 27.4 | 28.7 | 32.0 |

TABLE 31

Softness of 34 gsm spunbond fabrics made of plasticized mPP-1

|  | Neat | SHF-101 | SHF-101 | SHF-1003 |
|---|---|---|---|---|
| Concentration of fluid (%) | 0 | 3 | 5 | 5 |
| Softness Total Hand (grams) | | | | |
| 0.2 gram/hole/minute | 58.2 | 39.9 | 32.7 | 34.6 |
| 0.3 gram/hole/minute | 49.4 | 42.7 | 38.8 | 36.7 |
| 0.4 gram/hole/minute | 53.2 | 38.4 | 30.3 | 34.3 |

TABLE 32

Fluid concentration before and after fabrication of 34 gsm spunbond fabrics made of plasticized znPP-2

|  | SHF-101 | SHF-403 | SHF-1003 |
|---|---|---|---|
| Concentration of fluid (wt %) | 5 | 5 | 5 |
| Pellet | 4.6 | 4.7 | 5.5 |
| Fabric * | 4.2 | 4.5 | 5.5 |
| Fluid Retention (%)** | 91 | 96 | 100 |

* Fabrication condition: 20 grams/m², 0.2 grams per hole per minute
**Fluid Retention = 100 − (Concentration$_{pellet}$ − Concentration$_{fabric}$)*100/Concentration$_{pellet}$

We claim:

1. A fiber comprising a plasticized polyolefin composition comprising one or more polyolefins and one of more non-functionalized plasticizers where the non-functionalized plasticizer comprises $C_{20}$ to $C_{1500}$ paraffins having a Kinematic viscosity of 10 cSt or more at 100° C., a specific gravity of from 0.700 to 0.860, and a viscosity index of 120 or more.

2. The fiber of claim 1, where the non-functionalized plasticizer comprises 0.1 weight % or less of functional groups selected from hydroxide, aryls and substituted aryls, halogens, alkoxys, carboxylates, esters, carbon unsaturation, acrylates, oxygen, nitrogen, and carboxyl, based upon the weight of the NFP.

3. The fiber of claim 2 where the non-functionalized plasticizer has a glass transition temperature (Tg) that cannot be determined or if it can be determined then the Tg is less than 30° C.

4. The fiber of claim 2 where the non-functionalized plasticizer has a distillation range having a difference between the upper temperature and the lower temperature of 20° C. or less.

5. The fiber of claim 2 where the non-functionalized plasticizer has an initial boiling point greater than 110° C.

6. The fiber of claim 2 where the non-functionalized plasticizer has a pour point of −15° C. or less.

7. The fiber of claim 2 where the non-functionalized plasticizer has a specific gravity of less than 0.85.

8. The fiber of claim 2 where the non-functionalized plasticizer has a specific gravity from 0.70 to 0.85.

9. The fiber of claim 2 where the non-functionalized plasticizer has a final boiling point of from 115° C. to 500° C.

10. The fiber of claim 2 where the non-functionalized plasticizer has a weight average molecular weight between 2,000 and 100 g/mol.

11. The fiber of claim 2 where the non-functionalized plasticizer has a flash point of −30 to 350° C.

12. The fiber of claim 2 where the non-functionalized plasticizer has a dielectric constant at 20° C. of less than 3.0.

13. The fiber of claim 2 where the non-functionalized plasticizer has a density of from 0.70 to 0.83 g/cm³.

14. The fiber of claim 2 where the non-functionalized plasticizer has a viscosity of from 0.5 to 20 cSt at 25° C.

15. The fiber of claim 2 where the non-functionalized plasticizer has a carbon number of from 6 to 150.

16. The fiber of claim 2 where the non-functionalized plasticizer has a carbon number of from 7 to 100.

17. The fiber of claim 2 where the non-functionalized plasticizer has a carbon number of from 10 to 30.

18. The fiber of claim 2 where the non-functionalized plasticizer has a carbon number of from 12 to 25.

19. The fiber of claim 2 where the plasticized composition has a single glass transition temperature that is below that of the polyolefin itself.

20. The fiber of claim 2 where the $T_g$ of the plasticized composition is at least 4° C. lower than that of the neat polyolefin.

21. The fiber of claim 2 where in that the $T_g$ of the plasticized composition is at least 10° C. lower than that of the neat polyolefin.

22. The fiber of claim 2 where the $T_g$ of the plasticized composition is at least 15° C. lower than that of the neat polyolefin.

23. The fiber of claim 2 where the peak melting temperature of the neat polyolefin is within 1 to 4° C. of the plasticized polyolefin.

24. The fiber of claim 2 where the crystallization temperature of the neat polyolefin is within 1 to 4° C. of the plasticized polyolefin.

25. The fiber of claim 1, where the polyolefin comprises polypropylene or polybutene.

26. The fiber of claim 25 where the polyolefin comprises isotactic polypropylene.

27. The fiber of claim 25 where the polyolefin comprises syndiotactic polypropylene.

28. The fiber of claim 25 where the polyolefin comprises highly isotactic polypropylene.

29. The fiber of claim 25 where the polyolefin comprises a random copolymer of propylene and up to 5 weight % of ethylene.

30. The fiber of claim 25 where the polyolefin comprises an impact copolymer.

31. The fiber of claim 25 where the polyolefin further comprises an elastomer.

32. The fiber of claim 25 where the polyolefin further comprises a plastomer.

33. The fiber of claim 25 where the polyolefin has an Mw of 30,000 to 1,000,000 g/mol.

34. The fiber of claim 25 where the polyolefin has an Mw/Mn of 1.6 to 10.

35. The fiber of claim 25 where the polyolefin has a melting point (second melt) of 30 to 185° C.

36. The fiber of claim 25 where the polyolefin has a crystallinity of 5 to 80%.

37. The fiber of claim 25 where the polyolefin has a heat of fusion between 20 to 150 J/g.

38. The fiber of claim 25 where the polyolefin has a Gardner impact strength, tested on 0.125 inch disk at 23° C. of 20 in-lb to 1000 in-lb.

39. The fiber of claim 25 where the polyolefin has a 1% secant flexural modulus of from 100 MPa to 2300 MPa.

40. The fiber of claim 25 where the polyolefin has a melt flow rate from 0.3 to 500 dg/min.

41. The fiber of claim 25 where the polyolefin comprises a copolymer of propylene and from 0.5 to 30 weight % of one or more comonomers selected from the group consisting of ethylene, butene, pentene, hexene, heptene, octene, nonene, decene, dodecene, 4-methyl-pentene-1,3-methyl pentene-1,5-ethyl-1-nonene, and 3,5,5-trimethyl-hexene-1.

42. The fiber of claim 25 wherein the polyolefin comprises propylene, from 0 to 5 weight % of a diene, and from 2 wt % to 25 wt % ethylene, based on the total weight of the polymer and has a narrow compositional distribution; a melting point (Tm) of from 25° C. to 120° C.; a heat of fusion of from 50 J/g to 3 J/g; an Mw/Mn of from 1.5 to 5; and a melt index (MI) of less than 20 dg/min.

43. The fiber of claim 25 where the polyolefin has a tacticity index of 4 to 12.

44. The fiber of claim 25 where the polyolefin is present at 50 to 99.99 weight %, based upon the weight of the polyolefin and the non-functionalized plasticizer.

45. The fiber of claim 25 where non-functionalized plasticizer is present at 0.5 to 35 weight %, based upon the weight of the polyolefin and the non-functionalized plasticizer.

46. The fiber of claim 25 where non-functionalized plasticizer is present at 1 to 15 weight %, based upon the weight of the polyolefin and the non-functionalized plasticizer.

47. The fiber of claim 25 wherein the polyolefin is a propylene impact copolymer or blend comprising from 40% to 95% by weight of a Component A and from 5% to 60% by weight of a Component B based on the total weight of copolymer; wherein Component A comprises propylene homopolymer or copolymer, the copolymer comprising 10% or less by weight ethylene, butene, hexene or octene comonomer; and wherein Component B comprises propylene copolymer, wherein the copolymer comprises from 5% to 70% by weight ethylene, butene, hexene and/or octene comonomer, and from 95% to 30% by weight propylene.

48. The fiber of claim 47 wherein the refractive index of Component A and the refractive index of Component B are within 10% of each other, and, optionally the refractive index of the non-functionalized plasticizer is within 20% of Component A, Component B or both.

49. The fiber of claim 25 wherein polyethylene having a weight average molecular weight of from 500 to 10,000 is substantially absent and or wherein phthalates, adipates, trimellitate esters, and polyesters are substantially absent.

50. An article comprising the fiber of claim 25.

51. The article of claim 50 where the article is packaging material.

52. The article of claim 50 where the article is a package.

53. The article of claim 50 where the article is a nonwoven web.

54. The article of claim 50 where the article is a fabric.

55. The fiber of claim 25 where the fiber is spunbonded.

56. The fiber of claim 25 where the fiber is meltblown.

57. The article of claim 50 where the article is a yarn.

58. The fiber of claim 25 where the fiber is a staple fiber.

59. The article of claim 50 where the article is a surgical gown or drape.

60. The article of claim 50 where the article is clothing.

61. The fiber of claim 25 where the fiber is formed into an article selected from the group consisting of: yarns, woven fabrics, nonwoven fabrics, hook and loop fasteners, fabrics, garments, clothing, medical garments, surgical gowns, surgical drapes, diapers, training pants, sanitary napkins, panty liners, incontinent wear, bed pads, bags, packaging material, packages, swimwear, body fluid impermeable backsheets, body fluid impermeable layers, body fluid permeable layers, body fluid permeable covers, absorbents, tissues, nonwoven composites, liners, cloth linings, scrubbing pads, face masks, respirators, air filters, vacuum bags, oil and chemical spill sorbents, thermal insulation, first aid dressings, medical wraps, fiberfill, outerwear, bed quilt stuffing, furniture padding, filter media, scrubbing pads, wipe materials, hosiery, automotive seats, upholstered furniture, carpets, carpet backing, filter media, disposable wipes, diaper coverstock, gardening fabric, geomembranes, geotextiles, sacks, housewrap, vapor barriers, breathable clothing, envelops, tamper evident fabrics, protective packaging, and coasters.

62. The fiber of claim 25 wherein the fiber is formed into an article selected from the group consisting of: fabrics, garments, clothing, medical garments, surgical gowns, surgical drapes, diapers, training pants, sanitary napkins, panty liners, incontinent wear, bed pads, bags, packaging material, packages, swimwear, body fluid impermeable backsheets, body fluid impermeable layers, body fluid permeable layers, body fluid permeable covers, absorbents, tissues, nonwoven composites, liners, cloth linings, scrubbing pads, face masks, respirators, air filters, vacuum bags, oil and chemical spill sorbents, thermal insulation, first aid dressings, medical wraps, fiberfill, outerwear, bed quilt stuffing, furniture padding, filter media, scrubbing pads, wipe materials, hosiery, automotive seats, upholstered furniture, carpets, carpet backing, filter media, disposable wipes, diaper coverstock, gardening fabric, geomembranes, geotextiles, sacks, housewrap, vapor barriers, breathable clothing, envelops, tamper evident fabrics, protective packaging, and coasters.

63. A fiber comprising polyolefin and a non-functionalized plasticizer where the non-functionalized plasticizer has a specific gravity of from 0.700 to 0.860 and a viscosity index of 120 or more.

64. A fiber comprising polyolefin and a non-functionalized plasticizer where the non-functionalized plasticizer has a viscosity index of 120 or more and a pour point of −10° C. or less.

65. The fiber of claim 63 where the non-functionalized plasticizer has a viscosity index of 130 or more.

66. The fiber of claim 63 where the non-functionalized plasticizer has a viscosity index of 140 or more.

67. The fiber of claim 26 wherein elastomers are substantially absent from the plasticized polyolefin composition.

68. The fiber of claim 1 wherein elastomers are substantially absent from the plasticized polyolefin composition.

* * * * *